US009856319B2

(12) United States Patent
Ghayur et al.

(10) Patent No.: US 9,856,319 B2
(45) Date of Patent: Jan. 2, 2018

(54) MONOVALENT BINDING PROTEINS

(71) Applicant: AbbVie, Inc., Worcester, MA (US)

(72) Inventors: Tariq Ghayur, Holliston, MA (US); Jijie Gu, Shrewsbury, MA (US)

(73) Assignee: ABBVIE INC., North Chicago, IL (US)

( * ) Notice: Subject to any disclaimer, the term of this patent is extended or adjusted under 35 U.S.C. 154(b) by 651 days.

(21) Appl. No.: 14/141,503

(22) Filed: Dec. 27, 2013

(65) Prior Publication Data

US 2014/0221622 A1    Aug. 7, 2014

Related U.S. Application Data

(60) Provisional application No. 61/755,288, filed on Jan. 22, 2013, provisional application No. 61/746,615, filed on Dec. 28, 2012.

(51) Int. Cl.
C07K 16/00 (2006.01)
C07K 16/28 (2006.01)
C07K 16/32 (2006.01)
C07K 16/46 (2006.01)

(52) U.S. Cl.
CPC ...... C07K 16/2809 (2013.01); C07K 16/2863 (2013.01); C07K 16/2878 (2013.01); C07K 16/32 (2013.01); C07K 16/468 (2013.01); C07K 2317/35 (2013.01); C07K 2317/55 (2013.01); C07K 2317/565 (2013.01); C07K 2317/73 (2013.01); C07K 2317/74 (2013.01); C07K 2317/75 (2013.01); C07K 2317/76 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,006,309 A | 4/1991 | Khalil et al. | |
| 5,063,081 A | 11/1991 | Cozzette et al. | |
| 5,089,424 A | 2/1992 | Khalil et al. | |
| 5,169,939 A | 12/1992 | Gefter et al. | |
| 5,294,404 A | 3/1994 | Grandone et al. | |
| 5,624,821 A | 4/1997 | Winter et al. | |
| 5,648,260 A | 7/1997 | Winter et al. | |
| 5,968,509 A | 10/1999 | Gorman et al. | |
| 6,914,128 B1 | 7/2005 | Salfeld et al. | |
| 7,262,028 B2 | 8/2007 | Van Berkel et al. | |
| 7,419,821 B2 | 9/2008 | Davis et al. | |
| 7,429,486 B2 | 9/2008 | Van Berkel et al. | |
| 7,612,181 B2 | 11/2009 | Wu et al. | |
| 7,682,833 B2 | 3/2010 | Miller et al. | |
| 8,258,268 B2 | 9/2012 | Wu et al. | |
| 2004/0018577 A1 | 1/2004 | Campbell et al. | |
| 2005/0042664 A1 | 2/2005 | Wu et al. | |
| 2005/0063289 A1 | 3/2005 | Tomiyama et al. | |
| 2006/0160164 A1 | 7/2006 | Miller et al. | |
| 2007/0092520 A1 | 4/2007 | Dennis et al. | |
| 2009/0004192 A1* | 1/2009 | Pedersen | A61K 39/39558 424/136.1 |
| 2009/0239259 A1 | 9/2009 | Hsieh | |
| 2009/0311253 A1 | 12/2009 | Ghayur et al. | |
| 2011/0263827 A1 | 10/2011 | Ghayur et al. | |
| 2012/0237442 A1 | 9/2012 | Rossi et al. | |
| 2013/0108546 A1* | 5/2013 | Saldanha | C07K 16/18 424/1.49 |
| 2014/0213771 A1 | 7/2014 | Ghayur | |
| 2014/0213772 A1 | 7/2014 | Ghayur | |
| 2014/0219913 A1 | 8/2014 | Ghayur | |
| 2014/0221621 A1 | 8/2014 | Benatuil | |
| 2014/0221622 A1 | 8/2014 | Ghayur | |
| 2014/0234885 A1 | 8/2014 | Chumsae | |
| 2014/0235476 A1 | 8/2014 | Gu | |
| 2014/0242077 A1 | 8/2014 | Choi | |
| 2014/0243228 A1 | 8/2014 | Benatuil | |

FOREIGN PATENT DOCUMENTS

| | | |
|---|---|---|
| EP | 0131424 B1 | 9/1989 |
| WO | 1997029131 A1 | 8/1997 |
| WO | 2002002773 A2 | 1/2002 |
| WO | 2005063289 A1 | 7/2005 |
| WO | 2005063816 A2 | 7/2005 |
| WO | 2007/048037 A2 | 4/2007 |
| WO | 2007059782 A1 | 5/2007 |
| WO | 2012088302 A2 | 6/2012 |
| WO | 2012135345 A1 | 10/2012 |
| WO | PCT/US13/77908 | 12/2013 |
| WO | PCT/US13/77912 | 12/2013 |

(Continued)

OTHER PUBLICATIONS

Adams et al. 'Development of a Chimeric Anti-CD40 Monoclonal Antibody That Synergizes with LEA29Y to Prolong Islet Allograft Survival'. The Journal of Immunology. 2005. vol. 174, pp. 542-550.
Malmborg Hager et al. 'Affinity and Epitope Profiling of Mouse Anti-CD40 Monoclonal Antibodies'. Scandinavian Journal of Immunology. 2003, vol. 57, No. 6, pp. 517-523.
Hunig et al. 'CD28 superagonists: Mode of action and therapeutic potential' Immunology Letters. 2005, vol. 100, No. 1, pp. 21-28.
Cobbold et al. 'Therapy with monoclonal antibodies by elimination of T-cell subsets in vivo'. Nature. 1984, vol. 308, pp. 460-462.
Glennie et al. 'Univalent antibodies kill tumour cells in vitro and in vivo'. Nature. 1982, vol. 295, pp. 712-714.
Nielsen et al. 'Human T cells resistant to complement lysis by bivalent antibody can be efficiently lysed by dimers of monovalent antibody'. Blood. 2002, vol. 100, No. 12, pp. 4067-4073.

(Continued)

Primary Examiner — Brad Duffy
(74) Attorney, Agent, or Firm — Lathrop Gage LLP; James H. Velema, Esq.

(57) ABSTRACT

Engineered monovalent binding proteins that bind to one or more ligands (such as an antigen) via one binding domain are provided, along with methods of making and uses in the prevention, diagnosis, and/or treatment of disease.

7 Claims, 6 Drawing Sheets

(56) References Cited

FOREIGN PATENT DOCUMENTS

| WO | PCT/US13/77933 | 12/2013 |
|---|---|---|
| WO | PCT/US14/12362 | 1/2014 |
| WO | PCT/US14/12776 | 1/2014 |
| WO | WO 2014/106001 | 7/2014 |
| WO | WO 2014/106004 | 7/2014 |
| WO | WO 2014/106015 | 7/2014 |
| WO | WO 2014/116596 | 7/2014 |
| WO | WO 2014/116846 | 7/2014 |
| WO | PCT/US15/39110 | 7/2015 |
| WO | WO 2016/004389 | 1/2016 |

OTHER PUBLICATIONS

Stevenson et al. 'A chimeric antibody with dual Fc regions (bisFabFc) prepared by manipulations at the IgG hinge' Anti-cancer Drug Design. 1989, vol. 3, No. 4, pp. 219-230.

Routledge et al. 'The effect of aglycosylation on the immunogenicity of a humanized therapeutic CD3 monoclonal antibody'. Transplantation. 1995, vol. 60, No. 8, pp. 847-853.

Clark et al. 'The improved lytic function and in vivo efficacy of monovalent monoclonal CD3 antibodies'. European Journal of Immunology. 1989, vol. 19, No. 2, pp. 381-388.

Bolt et al. 'The generation of a humanized, non-mitogenic CD3 monoclonal antibody which retains in vitro immunosuppressive properties'. European Journal of Immunology. 1993, vol. 23, No. 2, pp. 403-411.

Routledge et al. 'A humanized monovalent CD3 antibody which can activate homologous complement'. European Journal of Immunology. 1991, vol. 21, No. 11, pp. 2717-2725.

Staerz et al. 'Hybrid Antibodies can Target Sites for attack by T Cells'. Letters to Nature. 1985, vol. 314, pp. 628-631.

Dennis et al. 'Albumin Binding as a General Strategy for Improving the Pharmacokinetics of Proteins'. The Journal of Biological Chemistry. 2002, vol. 277, No. 38, pp. 35035-35043.

Atwell et al. 'Stable Heterodimers from Remodeling the domain Interface of a Homodimer using a Phage Display Library'. Journal of Molecular Biology. 1997, vol. 270, pp. 26-35.

Durocher et al. 'High-level and high-throughput recombinant protein production by transient transfection of suspension-growing human 293-EBNA1 cells'. Nucleic Acids Research. 2002. vol. 30, No. 2, pp. E9.

Mizushima et al. 'pEF-BOS, A POwerful Mammalian Expression Vector'. Nucleic Acids Research. 1990, vol. 18, No. 17, pp. 5322-.

Marks et al. 'By-passing Immunization: Building High Affinity Human Antibodies by Chain Shuffling'. Biotechnology. 1992, vol. 10, pp. 779-783.

Barbas et al. 'In vitro Evolution of a Neutralizing Human Antibody to Human Immunodeficiency Virus type 1 to Enhance Affinity and Broaden Strain Cross-Reactivity'. PNAS. 1994, vol. 91, pp. 3809-3813.

Schier et al. 'Identification of functional and structural amino-acid residues by parsimonious mutagenesis'. Gene. 1996, vol. 169, pp. 147-155.

Yelton et al. 'Affinity Maturation of the BR96 Anti-Carcinoma Antibody by Codon-Based Mutagenesis'. Journal of Immunology. 1995, vol. 155, pp. 1994-2004.

Jackson et al. 'In vitro Antibody Maturation: Improvement of a High Affinity, Neutralizing Antibody Against IL-1β'. Journal of Immunology. 1995, vol. 154, No. 7, pp. 3310-3319.

Hawkins et al. 'Selection of Phage Antibodies by Binding Affinity Mimicking Affinity Maturation'. Journal of Molecular Biology. 1992, vol. 226, pp. 889-896.

Giege et al. Crystallization of Nucleic Acids and Proteins, A Practical Approach, 2nd Ed. pp. 1-16. Oxford University Press, New York, New York, (1999).

Holliger et al. "Diabodies": Small Bivalent and Bispecific Antibody Fragments'. PNAS. 1993, vol. 90, pp. 6444-6448.

Poljak et al. 'Production and Structure of Antibodies'. Structure. 1994, vol. 2, pp. 1121-1123.

Kabat et al. 'Attempts to Locate Complementarity-Determining Residues in the Variable Positions of Light and Heavy Chains'. Ann NY Acad Sci. 1971, vol. 190, pp. 382-391.

Chothia et al. 'Canonical Structures for the Hypervariable Regions of Immunoglobulins'. Journal of Molecular Biology. 1987, vol. 196, pp. 901-917.

Padlan et al. 'Identification of Specificity-Determining Residues in Antibodies'. FASEB J. 1995, vol. 9, pp. 133-139.

MacCallum et al. 'Antibody-antigen Interactions: Contact Analysis and Binding Site Topography'. Journal of Molecular Biology. 1996, vol. 262, pp. 732-745.

Jonsson et al. 'Introducing a Biosensor Based Technology for Real-time Biospecific Interaction Analysis'. Ann. Biol. Clin. 1993, vol. 51, pp. 19-26.

Kyte et al. 'A Simple Method for Displaying the Hydropathic Character of a Protein'. Journal of Molecular Biology. 1982, vol. 157, pp. 105-132.

Burke et al. 'Zotarolimus (ABT-578) eluting stents'. Advanced Drug Delivery Reviews. 2006, vol. 58, pp. 437-446.

Hildebrand et al. 'Surface Coatings for Biological Activation and Functionalization of Medical Devices'. Surface & Coatings Technology. 2006, vol. 200, pp. 6318-6324.

Wu et al. 'Drug/Device Combinations for Local Drug Therapies and Infection Prophylaxis'. Biomaterials. 2006, vol. 27, pp. 2450-2467.

Marques et al. 'Mediation of the Cytokine Network in the Implantations of Orthopedic Devices'. Chapter 21 in Biodegradable Systems in Tissue Engineering and Regenerative Medicine. pp. 377-397. (2005).

Coffman et al. 'Nonhuman Primate Models of Asthma'. The Journal of Experimental Medicine. 2005. vol. 201, No. 12, pp. 1875-1879.

Lloyd et al. 'Mouse Models of Allergic Airway Disease'. Advances in Immunology. 2001, vol. 77, pp. 263-295.

Boyce et al. 'No Audible Wheezing: Nuggets and Conundrums from Mouse Asthma Models'. The Journal of Experimental Medicine. 2005, vol. 201, No. 12, pp. 1869-1873.

Snibson et al. 'Airway Remodelling and Inflammation in Sheep Lungs After Chronic Airway Challenge with House Dust Mite'. Clinical & Experimental Allergy Reviews. 2005, vol. 35, No. 2, pp. 146-152.

Luster et al. 'Use of animal studies in risk assessment for immunotoxicology'. Toxicology. 1994, vol. 92, pp. 229-243.

Descotes. 'Immunotoxicology of Immunomodulators'. Developments in Biological Standardization. 1992, vol. 77, pp. 99-102.

Hart et al. 'Preclinical efficacy and safety of mepolizumab (SB-240563), a humanized monoclonal antibody to IL-5, in cynomolgus monkeys'. Journal of Allergy and Clinical Immunology. 2001, vol. 108, No. 2, pp. 250-257.

Witowski et al. 'Interleukin-17: a mediator of inflammatory responses'. Cellular and Molecular Life Sciences. 2004, vol. 61, pp. 567-579.

Brand. 'Rodent Models of Rheumatoid Arthritis'. Comparative Medicine. 2005, vol. 55, No. 2, pp. 114-122.

Morimoto et al. 'The increased interleukin-13 in patients with systemic lupus erythematosus: relations to other Th1-, Th2-related cytokines and clinical findings'. Autoimmunity. 2001. vol. 34, No. 1, pp. 19-25.

Wong et al. 'Hyperproduction of IL-23 and IL-17 in patients with systemic lupus erythematosus: Implications for Th17-mediated inflammation in auto-immunity'. Clinical Immunology. 2008. vol. 127, No. 3, pp. 385-393.

Steinman et al. 'Anti-neutrophil cytoplasmic autoantibodies and leukocyte—endothelial interactions: a sticky connection'. Trends in Immunology. 2005, vol. 26, No. 11, pp. 561-564.

Lublin et al. 'Relapsing experimental allergic encephalomyelitis an autoimmune model of multiple sclerosis'. Springer Seminars in Immunopathology. 1985. vol. 8, No. 3, pp. 197-208.

Genain et al. 'Creation of a model for multiple sclerosis in Callithrix jacchus marmosets'. Journal of Molecular Medicine. 1997, vol. 75, No. 3, pp. 187-197.

Tuohy et al. 'Spontaneous Regression of Primary Autoreactivity During Chronic Progression of Experimental Autoimmune Encephalomyelitis and Multiple Sclerosis'. Journal of Experimental Medicine. 1999, vol. 189, No. 7, pp. 1033-1042.

(56) References Cited

OTHER PUBLICATIONS

Owens et al. 'The immunology of multiple sclerosis and its animal model, experimental allergic encephalomyelitis'. Neurologic clinics. 1995, vol. 13, No. 1, pp. 51-73.
T'hart et al. 'Suppression of Ongoing Disease in a Nonhuman Primate Model of Multiple Sclerosis by a Human-Anti-Human IL-12p40 Antibody'. The Journal of Immunology. 2005, vol. 175, No. 7, pp. 4761-4768.
Flierl et al. 'Adverse Functions of IL-17A in Experimental Sepsis'. The FASEB Journal. 2008, vol. 22, pp. 2198-2205.
Coloma et al. 'Transport Across the Primate Blood-Brain Barrier of a Genetically Engineered Chimeric Monoclonal Antibody to the Human Insulin Receptor'. Pharmaceutical Research. 2000, vol. 17, No. 3, pp. 266-274.
Boado et al. 'Fusion Antibody for Alzheimer's Disease with Bidirectional Transport Across the Blood-Brain Barrier and Aβ Fibril Disaggregation'. Bioconjugate Chem. 2007, vol. 18, pp. 447-455.
Von Mehren et al. 'Monoclonal Antibody Therapy for Cancer'. Annu. Rev. Med. 2003. vol. 53, pp. 343-369.
Kolls et al. 'Interleukin-17: An Emerging Role in Lung Inflammation'. American Journal of Respiratory Cell and Molecular biology. 2003, vol. 28, pp. 9-11.
Terabe et al. 'Role of IL-13 in regulation of anti-tumor immunity and tumor growth'. Cancer Immunology, Immunotherapy. 2004, vol. 53, No. 2, pp. 79-85.
Goldspiel et al. 'Clinical Frontiers: Human Gene Therapy'. Clinical Pharmacy. 1993, vol. 12, pp. 488-505.
Wu and Wu. 'Delivery systems for Gene Therapy'. Biotherapy. 1991, vol. 3, pp. 87-95.
Tolstoshev et al. 'Gene Therapy, Concepts, Current Trials and Future Directions'. Annual Reviews in Pharmcology and Toxicology. 1993, vol. 32, pp. 573-593.
Mulligan. 'The Basic Science of Gene Therapy'. Science. 1993, vol. 260, pp. 926-932.
Morgan et al. 'Human Gene Therapy'. Annual Reviews in Biochemistry. 1993. vol. 62, pp. 191-217.
Nakamura et al. 'Molecular Cloning and Expression of Human Hepatocyte Growth Factor'. Nature. 1989, vol. 342, No. 6248, pp. 440-443.
Lokker et al. 'Structure-function analysis of hepatocyte growth factor: identification of variants that lack mitogenic activity yet retain high affinity receptor binding'. The EMBO Journal. 1992, vol. 11, No. 7, pp. 2503-2510.
Naka et al. 'Activation of hepatocyte growth factor by proteolytic conversion of a single chain form to a heterodimer'. Journal of Biological Chemistry. 1992, vol. 267, No. 28, pp. 20114-20119.
Peruzzi et al. 'Targeting the c-Met signaling pathway in cancer'. Clinical Cancer Research. vol. 12, No. 12, pp. 3657-3660.
Prat et al. 'Agonistic monoclonal antibodies against the Met receptor dissect the biological responses to HGF'. Journal of Cell Science. vol. 111, pp. 237-247.
Ohashi et al. 'Sustained survival of human hepatocytes in mice: A model for in vivo infection with human hepatitis B and hepatitis delta viruses'. Nature Medicine. 2000, vol. 6, pp. 327-331.
Guy et al. 'Organization of proximal signal initiation at the TCR: CD3 complex'. Immunological Reviews. 2009. vol. 232, No. 1, pp. 7-21.
Chatenoud. 'CD3-specific antibody-induced active tolerance: from bench to bedside'. Nature Reviews Immunology. vol. 3, No. 2, pp. 123-132.
Tibben et al. 'Cytokine Release in an Ovarian Carcinoma Patient Following Intravenous Administration of Bispecific Antibody OC/TR F (ab') 2'. Journal of the National Cancer Institute. 1993, vol. 85, No. 12, pp. 1003-1004.
Plevy et al. 'A Phase I Study of Visilizumab, a Humanized Anti-CD3 Monoclonal Antibody, in Severe Steroid-Refractory Ulcerative Colitis'. Gastroenterology. 2007, vol. 133, pp. 1414-1422.
Carpenter et al. 'Non-Fc Receptor-Binding Humanized Anti-CD3 Antibodies Induce Apoptosis of Activated Human T Cells'. The Journal of Immunology. 2000, vol. 165, No. 11, pp. 6205-6213.
Zlabinger et al. 'Cytokine release and dynamics of leukocyte populations after CD3/TCR monoclonal antibody treatment'. Journal of Clinical Immunology. 1992, vol. 12, No. 3, pp. 170-177.
Bugelski et al. 'Monoclonal antibody-induced cytokine-release syndrome'. Expert Review of Clinical Immunology. 2009, vol. 5, No. 5, pp. 499-521.
Wilde et al. 'Muromonab CD3'. Drugs. 1996, vol. 51, No. 5, pp. 865-894.
Onrust et al. 'Rituximab'. Drugs. 1999, vol. 58, No. 1, pp. 79-88.
Pound et al. 'Minimal cross-linking and epitope requirements for CD40-dependent suppression of apoptosis contrast with those for promotion of the cell cycle and homotypic adhesions in human B cells'. International Immunology. 1999, vol. 11, No. 1, pp. 11-20.
Beun et al. 'T-cell based cancer immunotherapy: direct or redirected tumor-cell recognition?' Immunology Today. 1994, vol. 15, pp. 11-15.
Perez et al. 'Specific targeting of cytotoxic T cells by anti-T3 linked to anti-target cell antibody'. Nature. 1985, vol. 316, pp. 354-356.
Demanet et al. 'Treatment of murine B cell lymphoma with bispecific monoclonal antibodies (anti-idiotype x anti-CD3)'. Journal of Immunology. 1991, vol. 147, pp. 1091-1097.
Bargou et al. 'Tumor regression in cancer patients by very low doses of a T cell-engaging antibody'. Science. 2008, vol. 321, No. 5981, pp. 974-977.
Rusch et al. 'Overexpression of the epidermal growth factor receptor and its ligand transforming growth factor alpha is frequent in resectable non-small cell lung cancer but does not predict tumor progression'. Clinical Cancer Research. 1997, vol. 3, pp. 515-522.
Pirker et al. 'Cetuximab plus chemotherapy in patients with advanced non-small-cell lung cancer (FLEX): an open-label randomised phase III trial'. Lancet. 2009, vol. 373, No. 9674, pp. 1525-1531.
Khambata-Ford et al. 'Analysis of Potential Predictive Markers of Cetuximab Benefit in BMS099, a Phase III Study of Cetuximab and First-Line Taxane/Carboplatin in Advanced Non-Small-Cell Lung Cancer'. Journal of Clinical Oncology. 2010, vol. 28, No. 6, pp. 918-927.
Zhu et al. 'Dynamic and label-free monitoring of natural killer cell cytotoxic activity using electronic cell sensor arrays'. Journal of Immunological Methods. 2006, vol. 309, pp. 25-33.
Birchmeier et al. 'Met, metastasis, motility and more'. Nature Reviews Molecular Cell Biology. 2003, vol. 4, No. 12, pp. 915-925.
Abidoye et al. 'Review of clinic trials: agents targeting c-Met'. Reviews on Recent Clinical Trials. 2007, vol. 2, No. 2, pp. 143-147.
Liu et al. 'Targeting the c-MET signaling pathway for cancer therapy'. Expert. Opin. Invest. Drugs. 2008, vol. 17, pp. 997-1011.
Grewal et al. 'CD40 and CD154 in cell-mediated immunity'. Annual Reviews in Immunology. 1998, vol. 16, No. 1, pp. 11-135.
Mach et al. 'Reduction of atherosclerosis in mice by inhibition of CD40 signalling' Letters to Nature. 1998, vol. 394, pp. 200-203.
Biancone. 'CD40-CD154 interaction in experimental and human disease'. International Journal of Molecular Medicine. 1999, vol. 3, No. 4, pp. 343-396.
Turner et al. 'Anti-CD40 Antibody Induces Antitumor and Antimetastatic Effects: The Role of NK Cells'. Journal of Immunology. 2001, vol. 166, No. 1, pp. 89-94.
Luqman et al. 'The antileukemia activity of a human anti-CD40 antagonist antibody, HCD122, on human chronic lymphocytic leukemia cells'. Blood. 2008, vol. 112, No. 3, pp. 711-720.
Beatty et al. 'CD40 Agonists Alter Tumor Stroma and Show Efficacy Against Pancreatic Carcinoma in Mice and Humans'. Science. 2011, vol. 331, No. 6024, pp. 1612-1616.
U.S. Appl. No. 14/141,502, filed Dec. 27, 2013, Tariq Ghayur.
U.S. Appl. No. 14/141,498, filed Dec. 27, 2013, Lorenzo Benatuil.
U.S. Appl. No. 14/141,500, filed Dec. 27, 2013, Lorenzo Benatuil.
U.S. Appl. No. 14/141,501, filed Dec. 27, 2013, Jijie Gu.
U.S. Appl. No. 14/161,552, filed Jan. 22, 2014, Chris Chumsae.
U.S. Appl. No. 14/162,716, filed Jan. 23, 2014, Chee-Ho Choi.
U.S. Appl. No. 14/141,503, filed Dec. 27, 2013, Tariq Ghayur.
U.S. Appl. No. 14/141,504, filed Dec. 27, 2013, Tariq Ghayur.
U.S. Appl. No. 14/141,499, filed Dec. 27, 2013, Tariq Ghayur.
Caravella et al. (2010) "Design of next-generation protein therapeutics," Curr. Opin. Chem. Biol. 14(4):520-528.

(56) References Cited

OTHER PUBLICATIONS

Gunasekaran et al. (2010) "Enhancing antibody Fc heterodimer formation through electrostatic steering effects: applications to bispecific molecules and monovalent IgG," Journal of Biological Chemistry. 285(25):19637-19646.
Holliger et al. (2005) "Engineered antibody fragments and the rise of single domains," Nat. Biotechnol. 23(9)1126-1136.
Hornig et al. (Jan. 1, 2012) "Production of Bispecific Antibodies: Diabodies and Tandem scFv," Ch. 40 In; Anitbody Engineering: Methods and Protocols. pp. 713-727.
Hudson et al. (2003) "Engineered Antibodies," Nat. Med. 9(1):129-134.
Klein et al. (Aug. 27, 2012) "Progress in overcoming the chain association issue in bispecific heterodimeric IgG antibodies," MAbs. 4:653-663.
Kontermann et al. (Mar. 2012) "Dual targeting strategies with bispecific antibodies," MAbs. 4(2):182-197.
Mack et al. (1995) "A small bispecific antibody construct expressed as a functional single-chain molecule with high tumor cell cytotoxicity," Proceedings of the National Academy of Sciences. 92(15):7021-7025.
Nagorsen et al. (Dec. 1, 2012) "Blinatumomab: A historical perspective," Pharmacology and Therapeutics. 136(3):334-342.
PRESTA (2008) "Molecular engineering and design of therapeutic antibodies," Curr. Opin. Immunol. 20(4):460-470.
Schaefer et al. (2011) "Immunoglobulin domain crossover as a generic approach for the production of bispecific IgG antibodies," Proceedings of the National Academy of Sciences. 108(27):11187-11192.
Wolf et al. (2005) "BiTEs: bispecific antibody constructs with unique anti-tumor activity," Drug Discovery Today. 10(18):1237-1244.
International Preliminary Report on Patentability corresponding to International Patent Application No. PCT/US2013/077933, dated Jun. 30, 2015.
International Search Report with Written Opinion corresponding to International Patent Application No. PCT/US2013/077933, dated Aug. 1, 2014.

* cited by examiner

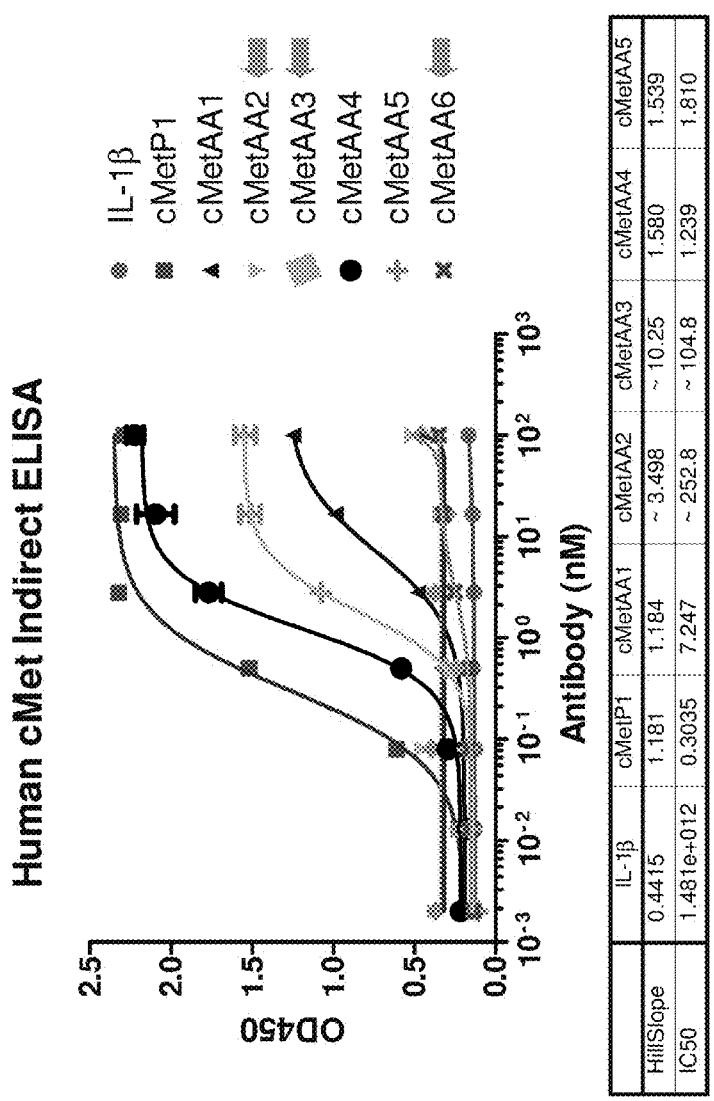
Fig. 1 MBody: Monovalent-targeting Immunoglobulin Inactivation of Antigen-binding by VH CDR3 Alanine Scanning

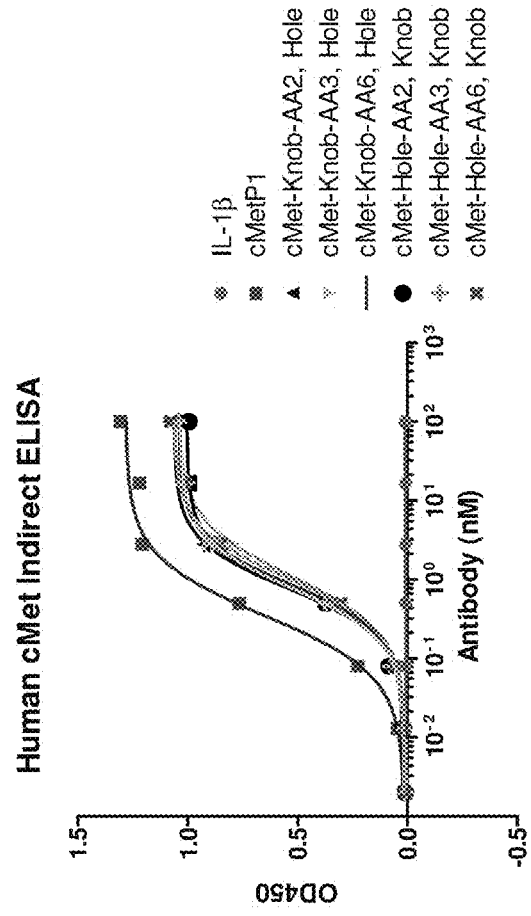
Fig. 2 Binding of cMet MBodies to Antigen

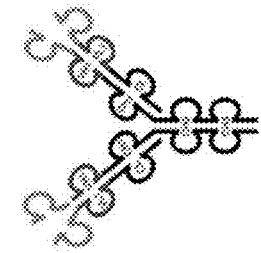
Fig. 3: Multi-Specific Full Length Antibody & HalfBody

Fig. 4  cMet ½ Body functions as an antagonist
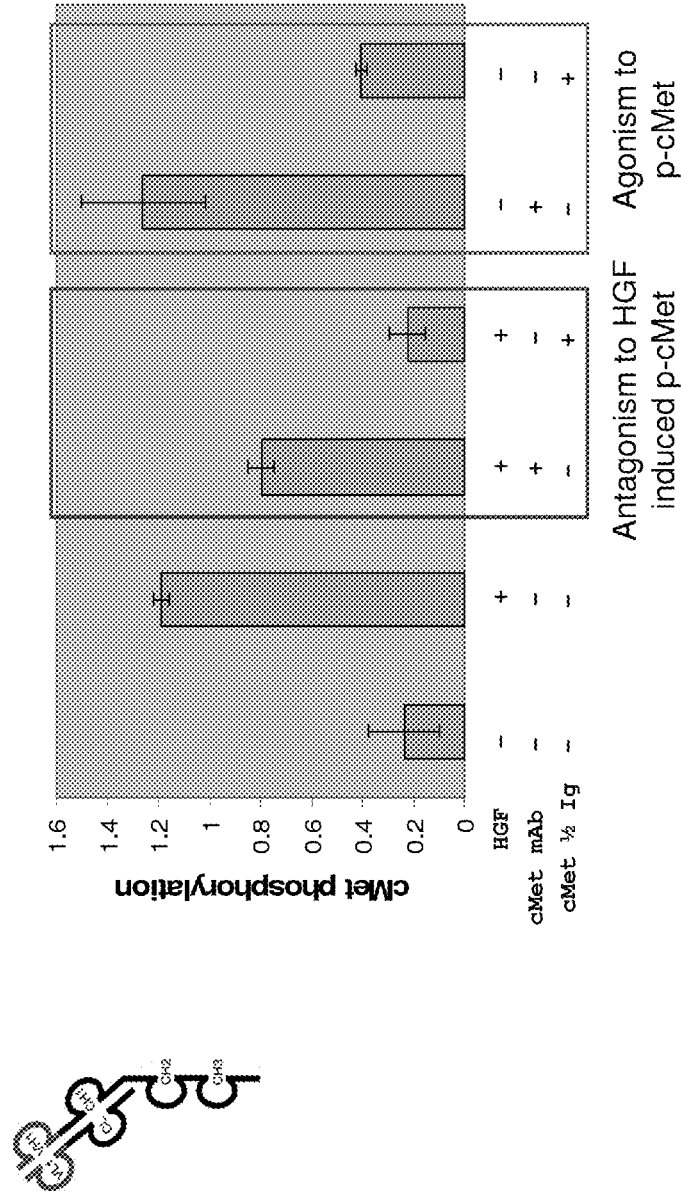

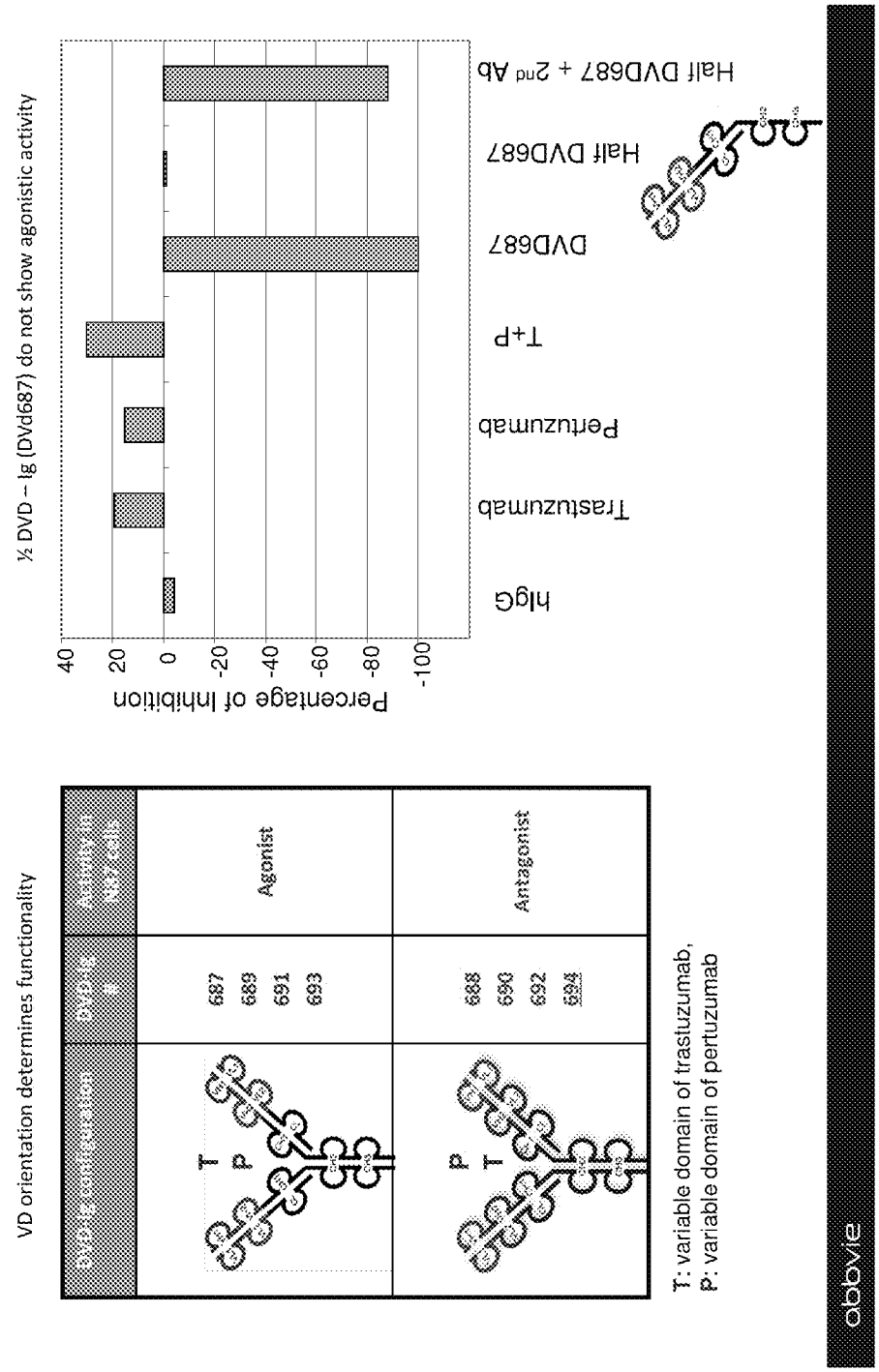
Fig. 5 ERBB2/ERBB2 DVD-Ig:
VD orientation and valency determines function

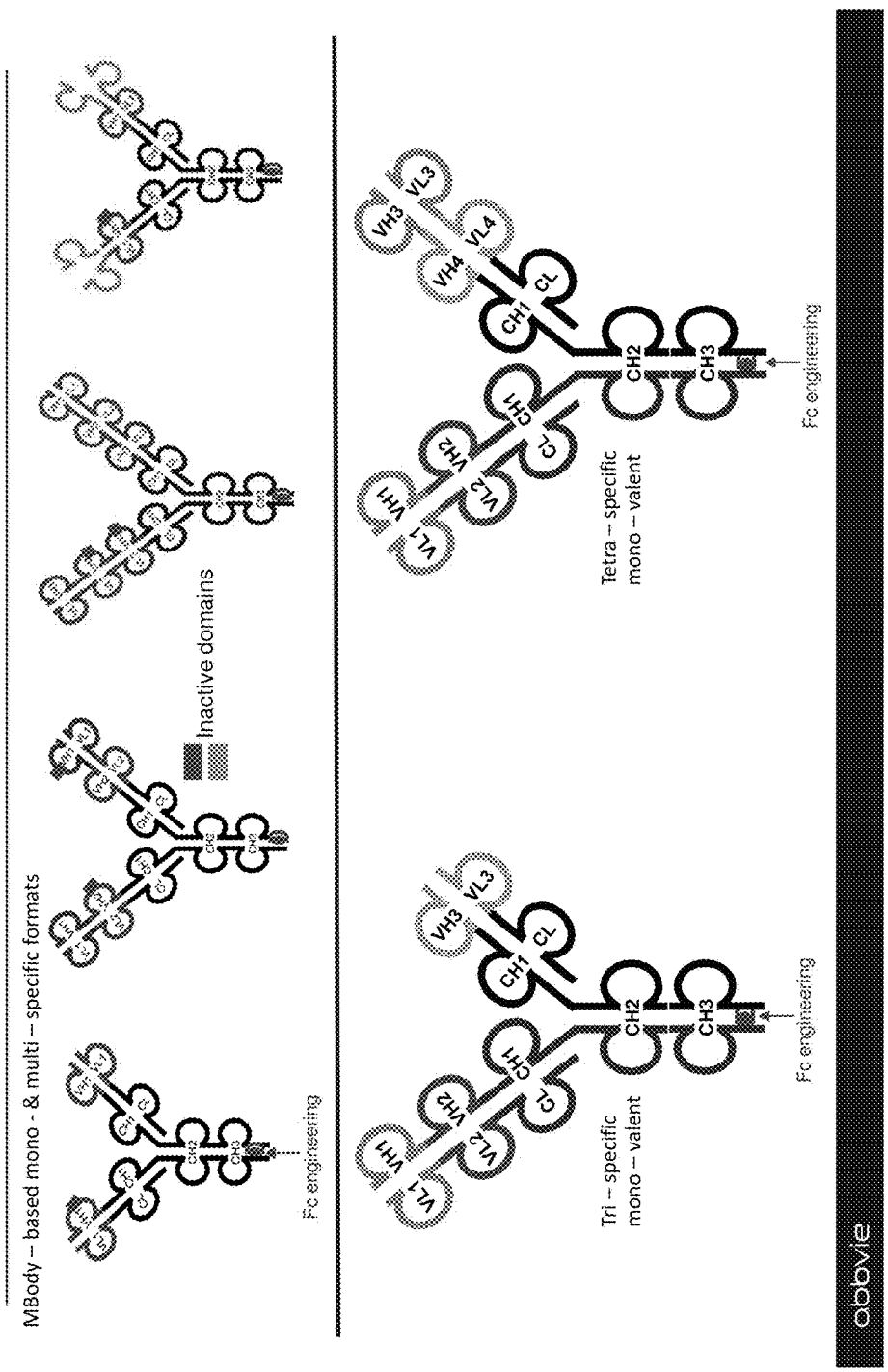

SEQUENCE LISTING

<160> NUMBER OF SEQ ID NOS: 103

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
caggtccaac tgcagcagtc tggggcctgag ctggtgaggc ctggggcttc agtgaagatg      60
tcctgcaggg cttcgggcta taccttcacc agctactggt tgcactgggt taaacagagg     120
cctggacaag gccttgagtg gattggcatg attgatcctt ccaatagtga cactaggttt     180
aatccgaact tcaaggacaa ggccacattg aatgtagaca gatcttccaa cacagcctac     240
atgctgctca gcagcctgac atctgctgac tctgcagtct attactgtgc cacatatggt     300
agctacgttt cccctctgga ctactgggg caaggaacct cagtcaccgt ctcctca         357
```

<210> SEQ ID NO 2
<211> LENGTH: 342
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 2

```
gactttatga tgtcacagtc tccatcctcc ctaactgtgt cagttggaga gaaggttact      60
gtgagctgca agtccagtca gtcccttta tatactagca gtcagaagaa ctacttggcc     120
tggtaccagc agaaaccagg tcagtctcct aaactgctga tttactgggc atccactagg     180
gaatctgggg tccctgatcg cttcacaggc agtggatctg gacagatttt cactctcacc     240
atcaccagtg tgaaggctga cgacctggca gtttattact gtcagcaata ttatgcctat     300
ccgtggacgt tcggtggagg caccaagttg gagctcaaac gg                       342
```

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 3

```
Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ser Tyr Val Ser Pro Leu Asp Tyr Trp Gly Gln Gly
            100                 105                 110

Thr Ser Val Thr Val Ser Ser
        115
```

<210> SEQ ID NO 4
<211> LENGTH: 114
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 4

Asp Phe Met Met Ser Gln Ser Pro Ser Ser Leu Thr Val Ser Val Gly
1               5                   10                  15

Glu Lys Val Thr Val Ser Cys Lys Ser Ser Gln Ser Leu Leu Tyr Thr
            20                  25                  30

Ser Ser Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65              70                  75                  80

Ile Thr Ser Val Lys Ala Asp Asp Leu Ala Val Tyr Tyr Cys Gln Gln
                85                  90                  95

Tyr Tyr Ala Tyr Pro Trp Thr Phe Gly Gly Gly Thr Lys Leu Glu Leu
            100                 105                 110

Lys Arg

<210> SEQ ID NO 5
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65              70                  75                  80

Met Leu Leu Ser Ser Leu Thr Ser Ala Asp Ser Ala Val Tyr Tyr Cys
                85                  90                  95

Ala Thr Tyr Gly Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

```
Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 6
<211> LENGTH: 220
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

```
Asp Phe Met Met Ser Gln Ser Pro Ser Ser Leu Thr Val Ser Val Gly
1               5                   10                  15

Glu Lys Val Thr Val Ser Cys Lys Ser Ser Gln Ser Leu Leu Tyr Thr
                20                  25                  30

Ser Ser Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Thr Ser Val Lys Ala Asp Asp Leu Ala Val Tyr Tyr Cys Gln Gln
                85                  90                  95

Tyr Tyr Ala Tyr Pro Trp Thr Phe Gly Gly Gly Thr Lys Leu Glu Leu
                100                 105                 110
```

```
Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
            85                  90                  95

Ala Ala Tyr Gly Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 8
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Ala Ala Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 9
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60
```

```
Lys Asp Lys Ala Thr Leu Asn Val Asp Arg Ser Ser Asn Thr Ala Tyr
 65                  70                  75                  80

Met Leu Leu Ser Ser Leu Thr Ser Ala Asp Ser Ala Val Tyr Tyr Cys
                 85                  90                  95

Ala Thr Tyr Gly Ala Ala Val Ser Pro Leu Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 10
<211> LENGTH: 449
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ser Tyr Ala Ala Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 12
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Pro Glu Leu Val Arg Pro Gly Ala
1               5                   10                  15
Ser Val Lys Met Ser Cys Arg Ala Ser Gly Tyr Thr Phe Thr Ser Tyr
            20                  25                  30
Trp Leu His Trp Val Lys Gln Arg Pro Gly Gln Gly Leu Glu Trp Ile
        35                  40                  45
Gly Met Ile Asp Pro Ser Asn Ser Asp Thr Arg Phe Asn Pro Asn Phe
50                  55                  60
Lys Asp Lys Ala Thr Leu Asn Val Asp Arg Ser Ser Asn Thr Ala Tyr
65                  70                  75                  80
Met Leu Leu Ser Ser Leu Thr Ser Ala Asp Ser Ala Val Tyr Tyr Cys
                85                  90                  95
Ala Thr Tyr Gly Ser Tyr Val Ser Pro Leu Ala Ala Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 13
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
            85                  90                  95

```
Ala Thr Ala Ala Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

-continued

```
Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Ala Ala Ser Tyr Val Ser Pro Leu Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
```

```
                        420                 425                 430
Ala Leu His Asn His Tyr Thr Gln Lys Ser Leu Ser Leu Ser Pro Gly
            435                 440                 445
Lys

<210> SEQ ID NO 15
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
                20                  25                  30

Trp Leu His Trp Val Lys Gln Arg Pro Gly Gln Gly Leu Glu Trp Ile
            35                  40                  45

Gly Met Ile Asp Pro Ser Asn Ser Asp Thr Arg Phe Asn Pro Asn Phe
        50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ala Ala Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                      325                 330                 335
Thr Ile Ser Lys Ala Lys Gly Gln Pro Arg Glu Pro Gln Val Tyr Thr
                  340                 345                 350

Leu Pro Pro Ser Arg Glu Glu Met Thr Lys Asn Gln Val Ser Leu Trp
              355                 360                 365

Cys Leu Val Lys Gly Phe Tyr Pro Ser Asp Ile Ala Val Glu Trp Glu
          370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 16
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ala Ala Val Ser Pro Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
            225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Ser
                355                 360                 365

Cys Ala Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 17
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
                20                  25                  30

Trp Leu His Trp Val Lys Gln Arg Pro Gly Gln Gly Leu Glu Trp Ile
                35                  40                  45

Gly Met Ile Asp Pro Ser Asn Ser Asp Thr Arg Phe Asn Pro Asn Phe
50                  55                  60

Lys Asp Lys Ala Thr Leu Asn Val Asp Arg Ser Ser Asn Thr Ala Tyr
65                  70                  75                  80

Met Leu Leu Ser Ser Leu Thr Ser Ala Asp Ser Ala Val Tyr Tyr Cys
                85                  90                  95

Ala Thr Tyr Gly Ser Tyr Val Ser Pro Leu Ala Ala Trp Gly Gln Gly
                100                 105                 110

Thr Ser Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Trp
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 18
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
                20                  25                  30

Trp Leu His Trp Val Lys Gln Arg Pro Gly Gln Gly Leu Glu Trp Ile
```

```
                35                  40                  45
Gly Met Ile Asp Pro Ser Asn Ser Asp Thr Arg Phe Asn Pro Asn Phe
 50                  55                  60

Lys Asp Lys Ala Thr Leu Asn Val Asp Arg Ser Ser Asn Thr Ala Tyr
 65                  70                  75                  80

Met Leu Leu Ser Ser Leu Thr Ser Ala Asp Ser Ala Val Tyr Tyr Cys
                 85                  90                  95

Ala Thr Tyr Gly Ser Tyr Val Ser Pro Leu Ala Ala Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 19
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caagtccagc tgcagcagtc cggcgctgag ctggcccgac ccggcgctag cgtgaagatg        60
tcatgcaagg ccagcggtta tacatttacc aggtacacta tgcattgggt gaaacagaga       120
cctggacagg gcctcgagtg gatcgggtac ataaatccct cacgcggcta tacaaactac       180
aatcagaagt tcaaggacaa ggcaacactc actactgaca agagctcatc aaccgcctat       240
atgcagttgt cttcactgac ctccgaggac tctgcagtgt actactgcgc gcggtactac       300
gacgaccact actgcctcga ctactggggg cagggtacca ctctgaccgt gtcctcc         357

<210> SEQ ID NO 20
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caaattgttc tcacccagtc tccagcaatc atgtctgcat ctccagggga gaaggtcacc        60
atgacctgca gtgccagctc aagtgtaagt tacatgaact ggtaccagca gaagtcaggc       120
acctccccca aaagatggat ttatgacaca tccaaactgg cttctggagt ccctgctcac       180
ttcaggggca gtgggtctgg gacctcttac tctctcacaa tcagcggcat ggaggctgaa       240
gatgctgcca cttattactg ccagcagtgg agtagtaacc cattcacgtt cggctcgggg       300
acaaagttgg aaataaaccg g                                                 321

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 23
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser

```
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 24
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Val Leu Thr Gln Ser Pro Ala Ile Met Ser Ala Ser Pro Gly
1               5                   10                  15
Glu Lys Val Thr Met Thr Cys Ser Ala Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Leu Ala Ser Gly Val Pro Ala His Phe Arg Gly Ser
        50                  55                  60
Gly Ser Gly Thr Ser Tyr Ser Leu Thr Ile Ser Gly Met Glu Ala Glu
65                  70                  75                  80
Asp Ala Ala Thr Tyr Tyr Cys Gln Gln Trp Ser Ser Asn Pro Phe Thr
```

```
                85                  90                  95
Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 25
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Ala Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 26
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Ala Ala His Tyr Cys Leu Asp Tyr Trp Gly Gln Gly
        100                 105                 110

Thr Thr Leu Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 27
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

```
Thr Met His Trp Val Lys Gln Arg Pro Gly Gln Gly Leu Glu Trp Ile
         35                   40                  45

Gly Tyr Ile Asn Pro Ser Arg Gly Tyr Thr Asn Tyr Asn Gln Lys Phe
 50                   55                  60

Lys Asp Lys Ala Thr Leu Thr Thr Asp Lys Ser Ser Ser Thr Ala Tyr
 65                   70                  75                  80

Met Gln Leu Ser Ser Leu Thr Ser Glu Asp Ser Ala Val Tyr Tyr Cys
                 85                  90                  95

Ala Arg Tyr Tyr Asp Asp Ala Ala Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 28
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ala Ala Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 29
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Ala Ala Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                    260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 30
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Ala Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Trp
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 31
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
```

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 32
<211> LENGTH: 449
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 32

```
Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Ala Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 33
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 34
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggttcagc tcaaacagag cgggcccggg ctggtacagc cctcccagtc tcttagtatc      60
acatgcacag tcagcgggtt cagcctcacc aactatgggg ttcactgggt gcgccagtca     120
cctggaaagg gcttggagtg gctgggcgtc atttggtccg gaggcaacac cgactacaac     180
acacccttca ctagccggct gagcattaac aaagacaata gcaagtccca agtgttcttt     240
aagatgaata gcctccaatc taacgacaca gcgatttact attgcgcccg ggccctgacc     300
tactatgact atgaatttgc ctactggggg caaggaactc tggtaactgt atccgctgca     360
agcacgaagg ggcctagcgt tttcccactg gctccccaag tccagctgca gcagtccggc     420
gctgagctgg cccgacccgg cgctagcgtg aagatgtcat gcaaggccag cggttataca     480
tttaccaggt acactatgca ttgggtgaaa cagagacctg gacagggcct cgagtggatc     540
gggtacataa atccctcacg cggctataca aactacaatc agaagttcaa ggacaaggcg     600
acactcacta ctgacaagag ctcatcaacc gcctatatgc agttgtcttc actgaccctc     660
gaggactctg cagtgtacta ctgcgcgcgg tactacgacg accactactg cctcgactac     720
tgggggcagg gtaccactct gaccgtgtcc tcc                                  753

<210> SEQ ID NO 35
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatatccttc tgacacaaag tcctgtaatc ctttccgtta gcccgggtga gagggtctct      60
```

-continued

```
ttcagctgta gagcgtccca gtccatcggt accaacatcc actggtatca gcagcggacc    120
aatggtagcc cacgacttct catcaagtac gcaagtgaat caattagtgg aatcccttcc    180
cggttttctg gatcaggctc tggtacggac ttcacgctga gcatcaactc tgtcgaatcc    240
gaggatatcg ctgactacta ctgccagcaa ataataatt ggccaacgac atttggcgcc     300
gggactaagc ttgaactgaa acggaccgtg gcagccccta gtgtgttcat ctttccaccc    360
cagattgttc tgacccagag cccggctata atgagtgcct ctccaggtga aaggtcacc     420 atgacatgtc gagcctcttc ctccgttcct tacatgaact ggtatcaaca gaagtccgga    480
acttccccta acggtggat ttatgatact agcaaagttg ccagcggtgt gccatatcgc     540
tttagcggga gcggtagcgg gaccagttat agtttgacca tcagcagcat ggaagcagag    600
gatgcggcca cttattattg ccaacaatgg tccagcaacc ctttgacttt cggtagtggc    660
actaagcttg agatcaatcg c                                              681
```

<210> SEQ ID NO 36
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Gln Val Gln Leu Gln Gln Ser Gly Ala Glu Leu Ala
    130                 135                 140

Arg Pro Gly Ala Ser Val Lys Met Ser Cys Lys Ala Ser Gly Tyr Thr
145                 150                 155                 160

Phe Thr Arg Tyr Thr Met His Trp Val Lys Gln Arg Pro Gly Gln Gly
                165                 170                 175

Leu Glu Trp Ile Gly Tyr Ile Asn Pro Ser Arg Gly Tyr Thr Asn Tyr
            180                 185                 190

Asn Gln Lys Phe Lys Asp Lys Ala Thr Leu Thr Thr Asp Lys Ser Ser
        195                 200                 205

Ser Thr Ala Tyr Met Gln Leu Ser Ser Leu Thr Ser Glu Asp Ser Ala
    210                 215                 220

Val Tyr Tyr Cys Ala Arg Tyr Tyr Asp Asp His Tyr Cys Leu Asp Tyr
225                 230                 235                 240
```

```
Trp Gly Gln Gly Thr Thr Leu Thr Val Ser Ser
            245                 250
```

<210> SEQ ID NO 37
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Gln Ile Val Leu Thr Gln Ser Pro
        115                 120                 125

Ala Ile Met Ser Ala Ser Pro Gly Glu Lys Val Thr Met Thr Cys Arg
130                 135                 140

Ala Ser Ser Ser Val Ser Tyr Met Asn Trp Tyr Gln Gln Lys Ser Gly
145                 150                 155                 160

Thr Ser Pro Lys Arg Trp Ile Tyr Asp Thr Ser Lys Val Ala Ser Gly
                165                 170                 175

Val Pro Tyr Arg Phe Ser Gly Ser Gly Ser Gly Thr Ser Tyr Ser Leu
            180                 185                 190

Thr Ile Ser Ser Met Glu Ala Glu Asp Ala Ala Thr Tyr Tyr Cys Gln
        195                 200                 205

Gln Trp Ser Ser Asn Pro Leu Thr Phe Gly Ser Gly Thr Lys Leu Glu
210                 215                 220

Ile Asn Arg
225
```

<210> SEQ ID NO 38
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

-continued

```
Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Gln Val Gln Leu Gln Gln Ser Gly Ala Glu Leu Ala
130                 135                 140

Arg Pro Gly Ala Ser Val Lys Met Ser Cys Lys Ala Ser Gly Tyr Thr
145                 150                 155                 160

Phe Thr Arg Tyr Thr Met His Trp Val Lys Gln Arg Pro Gly Gln Gly
                165                 170                 175

Leu Glu Trp Ile Gly Tyr Ile Asn Pro Ser Arg Gly Tyr Thr Asn Tyr
            180                 185                 190

Asn Gln Lys Phe Lys Asp Lys Ala Thr Leu Thr Thr Asp Lys Ser Ser
        195                 200                 205

Ser Thr Ala Tyr Met Gln Leu Ser Ser Leu Thr Ser Glu Asp Ser Ala
    210                 215                 220

Val Tyr Tyr Cys Ala Arg Tyr Tyr Asp Asp His Tyr Cys Leu Asp Tyr
225                 230                 235                 240

Trp Gly Gln Gly Thr Thr Leu Thr Val Ser Ser Ala Ser Thr Lys Gly
                245                 250                 255

Pro Ser Val Phe Pro Leu Ala Pro Ser Ser Lys Ser Thr Ser Gly Gly
            260                 265                 270

Thr Ala Ala Leu Gly Cys Leu Val Lys Asp Tyr Phe Pro Glu Pro Val
        275                 280                 285

Thr Val Ser Trp Asn Ser Gly Ala Leu Thr Ser Gly Val His Thr Phe
    290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Lys Val Glu Pro Lys
            340                 345                 350

Ser Cys Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
```

```
                465                 470                 475                 480
Gln Val Tyr Thr Leu Pro Pro Ser Arg Glu Glu Met Thr Lys Asn Gln
                    485                 490                 495

Val Ser Leu Thr Cys Leu Val Lys Gly Phe Tyr Pro Ser Asp Ile Ala
                500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
            580

<210> SEQ ID NO 39
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Gln Ile Val Leu Thr Gln Ser Pro
        115                 120                 125

Ala Ile Met Ser Ala Ser Pro Gly Glu Lys Val Thr Met Thr Cys Arg
    130                 135                 140

Ala Ser Ser Ser Val Ser Tyr Met Asn Trp Tyr Gln Gln Lys Ser Gly
145                 150                 155                 160

Thr Ser Pro Lys Arg Trp Ile Tyr Asp Thr Ser Lys Val Ala Ser Gly
                165                 170                 175

Val Pro Tyr Arg Phe Ser Gly Ser Gly Ser Gly Thr Ser Tyr Ser Leu
            180                 185                 190

Thr Ile Ser Ser Met Glu Ala Glu Asp Ala Ala Thr Tyr Tyr Cys Gln
        195                 200                 205

Gln Trp Ser Ser Asn Pro Leu Thr Phe Gly Ser Gly Thr Lys Leu Glu
    210                 215                 220

Ile Asn Arg Thr Val Ala Ala Pro Ser Val Phe Ile Phe Pro Pro Ser
225                 230                 235                 240
```

```
Asp Glu Gln Leu Lys Ser Gly Thr Ala Ser Val Val Cys Leu Leu Asn
            245                 250                 255

Asn Phe Tyr Pro Arg Glu Ala Lys Val Gln Trp Lys Val Asp Asn Ala
        260                 265                 270

Leu Gln Ser Gly Asn Ser Gln Glu Ser Val Thr Glu Gln Asp Ser Lys
    275                 280                 285

Asp Ser Thr Tyr Ser Leu Ser Ser Thr Leu Thr Leu Ser Lys Ala Asp
290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 40
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Gln Val Gln Leu Gln Gln Ser Gly Ala Glu Leu Ala
    130                 135                 140

Arg Pro Gly Ala Ser Val Lys Met Ser Cys Lys Ala Ser Gly Tyr Thr
145                 150                 155                 160

Phe Thr Arg Tyr Thr Met His Trp Val Lys Gln Arg Pro Gly Gln Gly
                165                 170                 175

Leu Glu Trp Ile Gly Tyr Ile Asn Pro Ser Arg Gly Tyr Thr Asn Tyr
            180                 185                 190

Asn Gln Lys Phe Lys Asp Lys Ala Thr Leu Thr Thr Asp Lys Ser Ser
        195                 200                 205

Ser Thr Ala Tyr Met Gln Leu Ser Ser Leu Thr Ser Glu Asp Ser Ala
    210                 215                 220

Val Tyr Tyr Cys Ala Arg Ala Asp Asp His Tyr Cys Leu Asp Tyr
225                 230                 235                 240

Trp Gly Gln Gly Thr Thr Leu Thr Val Ser Ser Ala Ser Thr Lys Gly
                245                 250                 255

Pro Ser Val Phe Pro Leu Ala Pro Ser Ser Lys Ser Thr Ser Gly Gly
            260                 265                 270
```

```
Thr Ala Ala Leu Gly Cys Leu Val Lys Asp Tyr Phe Pro Glu Pro Val
            275                 280                 285

Thr Val Ser Trp Asn Ser Gly Ala Leu Thr Ser Gly Val His Thr Phe
        290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Lys Val Glu Pro Lys
            340                 345                 350

Ser Cys Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Glu Glu Met Thr Lys Asn Gln
                485                 490                 495

Val Ser Leu Trp Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Lys Leu
    530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
            580

<210> SEQ ID NO 41
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
```

-continued

```
                35                  40                  45
Gly Val Ile Trp Ser Gly Gly Asn Thr Asp Tyr Asn Thr Pro Phe Thr
 50                  55                  60
Ser Arg Leu Ser Ile Asn Lys Asp Asn Ser Lys Ser Gln Val Phe Phe
 65                  70                  75                  80
Lys Met Asn Ser Leu Gln Ser Asn Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
                115                 120                 125
Pro Leu Ala Pro Gln Val Gln Leu Gln Gln Ser Gly Ala Glu Leu Ala
130                 135                 140
Arg Pro Gly Ala Ser Val Lys Met Ser Cys Lys Ala Ser Gly Tyr Thr
145                 150                 155                 160
Phe Thr Arg Tyr Thr Met His Trp Val Lys Gln Arg Pro Gly Gln Gly
                165                 170                 175
Leu Glu Trp Ile Gly Tyr Ile Asn Pro Ser Arg Gly Tyr Thr Asn Tyr
                180                 185                 190
Asn Gln Lys Phe Lys Asp Lys Ala Thr Leu Thr Thr Asp Lys Ser Ser
                195                 200                 205
Ser Thr Ala Tyr Met Gln Leu Ser Ser Leu Thr Ser Glu Asp Ser Ala
                210                 215                 220
Val Tyr Tyr Cys Ala Arg Tyr Tyr Asp Asp His Tyr Cys Leu Asp Tyr
225                 230                 235                 240
Trp Gly Gln Gly Thr Thr Leu Thr Val Ser Ser Ala Ser Thr Lys Gly
                245                 250                 255
Pro Ser Val Phe Pro Leu Ala Pro Ser Ser Lys Ser Thr Ser Gly Gly
                260                 265                 270
Thr Ala Ala Leu Gly Cys Leu Val Lys Asp Tyr Phe Pro Glu Pro Val
                275                 280                 285
Thr Val Ser Trp Asn Ser Gly Ala Leu Thr Ser Gly Val His Thr Phe
                290                 295                 300
Pro Ala Val Leu Gln Ser Ser Gly Leu Tyr Ser Leu Ser Ser Val Val
305                 310                 315                 320
Thr Val Pro Ser Ser Ser Leu Gly Thr Gln Thr Tyr Ile Cys Asn Val
                325                 330                 335
Asn His Lys Pro Ser Asn Thr Lys Val Asp Lys Lys Val Glu Pro Lys
                340                 345                 350
Ser Cys Asp Lys Thr His Thr Cys Pro Pro Cys Pro Ala Pro Glu Leu
                355                 360                 365
Leu Gly Gly Pro Ser Val Phe Leu Phe Pro Pro Lys Pro Lys Asp Thr
                370                 375                 380
Leu Met Ile Ser Arg Thr Pro Glu Val Thr Cys Val Val Val Asp Val
385                 390                 395                 400
Ser His Glu Asp Pro Glu Val Lys Phe Asn Trp Tyr Val Asp Gly Val
                405                 410                 415
Glu Val His Asn Ala Lys Thr Lys Pro Arg Glu Glu Gln Tyr Asn Ser
                420                 425                 430
Thr Tyr Arg Val Val Ser Val Leu Thr Val Leu His Gln Asp Trp Leu
                435                 440                 445
Asn Gly Lys Glu Tyr Lys Cys Lys Val Ser Asn Lys Ala Leu Pro Ala
                450                 455                 460
```

```
Pro Ile Glu Lys Thr Ile Ser Lys Ala Lys Gly Gln Pro Arg Glu Pro
465                 470                 475                 480

Gln Val Tyr Thr Leu Pro Pro Ser Arg Glu Glu Met Thr Lys Asn Gln
                485                 490                 495

Val Ser Leu Ser Cys Ala Val Lys Gly Phe Tyr Pro Ser Asp Ile Ala
            500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Val Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
            565                 570                 575

Leu Ser Pro Gly Lys
            580

<210> SEQ ID NO 42
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Gln Val Gln Leu Gln Gln Ser Gly Ala Glu Leu Ala
    130                 135                 140

Arg Pro Gly Ala Ser Val Lys Met Ser Cys Lys Ala Ser Gly Tyr Thr
145                 150                 155                 160

Phe Thr Arg Tyr Thr Met His Trp Val Lys Gln Arg Pro Gly Gln Gly
                165                 170                 175

Leu Glu Trp Ile Gly Tyr Ile Asn Pro Ser Arg Gly Tyr Thr Asn Tyr
            180                 185                 190

Asn Gln Lys Phe Lys Asp Lys Ala Thr Leu Thr Thr Asp Lys Ser Ser
            195                 200                 205

Ser Thr Ala Tyr Met Gln Leu Ser Ser Leu Thr Ser Glu Asp Ser Ala
        210                 215                 220

Val Tyr Tyr Cys Ala Arg Ala Ala Asp Asp His Tyr Cys Leu Asp Tyr
```

```
                225                 230                 235                 240
Trp Gly Gln Gly Thr Thr Leu Thr Val Ser Ser Ala Ser Thr Lys Gly
                245                 250                 255

Pro Ser Val Phe Pro Leu Ala Pro Ser Ser Lys Ser Thr Ser Gly Gly
                260                 265                 270

Thr Ala Ala Leu Gly Cys Leu Val Lys Asp Tyr Phe Pro Glu Pro Val
                275                 280                 285

Thr Val Ser Trp Asn Ser Gly Ala Leu Thr Ser Gly Val His Thr Phe
                290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Val Glu Pro Lys
                340                 345                 350

Ser Cys Asp Lys Thr His Thr Cys Pro Pro Cys Pro Ala Pro Glu Leu
                355                 360                 365

Leu Gly Gly Pro Ser Val Phe Leu Phe Pro Pro Lys Pro Lys Asp Thr
                370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
                420                 425                 430

Thr Tyr Arg Val Val Ser Val Leu Thr Val Leu His Gln Asp Trp Leu
                435                 440                 445

Asn Gly Lys Glu Tyr Lys Cys Lys Val Ser Asn Lys Ala Leu Pro Ala
                450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Glu Glu Met Thr Lys Asn Gln
                485                 490                 495

Val Ser Leu Ser Cys Ala Val Lys Gly Phe Tyr Pro Ser Asp Ile Ala
                500                 505                 510

Val Glu Trp Glu Ser Asn Gly Gln Pro Glu Asn Asn Tyr Lys Thr Thr
                515                 520                 525

Pro Pro Val Leu Asp Ser Asp Gly Ser Phe Phe Leu Val Ser Lys Leu
                530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
                580

<210> SEQ ID NO 43
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43
```

-continued

```
Gln Val Gln Leu Lys Gln Ser Gly Pro Gly Leu Val Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Gln Val Gln Leu Gln Gln Ser Gly Ala Glu Leu Ala
        130                 135                 140

Arg Pro Gly Ala Ser Val Lys Met Ser Cys Lys Ala Ser Gly Tyr Thr
145                 150                 155                 160

Phe Thr Arg Tyr Thr Met His Trp Val Lys Gln Arg Pro Gly Gln Gly
                165                 170                 175

Leu Glu Trp Ile Gly Tyr Ile Asn Pro Ser Arg Gly Tyr Thr Asn Tyr
            180                 185                 190

Asn Gln Lys Phe Lys Asp Lys Ala Thr Leu Thr Thr Asp Lys Ser Ser
        195                 200                 205

Ser Thr Ala Tyr Met Gln Leu Ser Ser Leu Thr Ser Glu Asp Ser Ala
    210                 215                 220

Val Tyr Tyr Cys Ala Arg Tyr Tyr Asp Asp His Tyr Cys Leu Asp Tyr
225                 230                 235                 240

Trp Gly Gln Gly Thr Thr Leu Thr Val Ser Ser Ala Ser Thr Lys Gly
                245                 250                 255

Pro Ser Val Phe Pro Leu Ala Pro Ser Ser Lys Ser Thr Ser Gly Gly
            260                 265                 270

Thr Ala Ala Leu Gly Cys Leu Val Lys Asp Tyr Phe Pro Glu Pro Val
        275                 280                 285

Thr Val Ser Trp Asn Ser Gly Ala Leu Thr Ser Gly Val His Thr Phe
    290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Lys Val Glu Pro Lys
            340                 345                 350

Ser Cys Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
```

```
                420             425             430
Thr Tyr Arg Val Val Ser Val Leu Thr Val Leu His Gln Asp Trp Leu
        435             440             445

Asn Gly Lys Glu Tyr Lys Cys Lys Val Ser Asn Lys Ala Leu Pro Ala
    450             455             460

Pro Ile Glu Lys Thr Ile Ser Lys Ala Lys Gly Gln Pro Arg Glu Pro
465             470             475             480

Gln Val Tyr Thr Leu Pro Pro Ser Arg Glu Glu Met Thr Lys Asn Gln
            485             490             495

Val Ser Leu Trp Cys Leu Val Lys Gly Phe Tyr Pro Ser Asp Ile Ala
                500             505             510

Val Glu Trp Glu Ser Asn Gly Gln Pro Glu Asn Asn Tyr Lys Thr Thr
            515             520             525

Pro Pro Val Leu Asp Ser Asp Gly Ser Phe Phe Leu Tyr Ser Lys Leu
        530             535             540

Thr Val Asp Lys Ser Arg Trp Gln Gln Gly Asn Val Phe Ser Cys Ser
545             550             555             560

Val Met His Glu Ala Leu His Asn His Tyr Thr Gln Lys Ser Leu Ser
            565             570             575

Leu Ser Pro Gly Lys
        580

<210> SEQ ID NO 44
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caagtccagc tggtgcagag cggggcggag gtcaaaaagc cggggggcaag cgtcaaggtg       60 agctgtaaag ctagtggtta caccttacc gggtattaca tgcattgggt gcggcaggcg       120
cccggccaag ggctcgaatg gatgggttgg ataaacccag attccggcgg aacaaactat      180
gcgcagaaat tccagggcag agtcaccatg accaggata cctctatctc tacggcttac       240
atggagttga accgcctgcg cagcgatgac acagctgtct actattgcgc gagggatcag      300
ccactgggct actgcaccaa tggcgtgtgc agctatttcg actactgggg tcagggaacc      360
ctcgtgaccg tttcctcc                                                    378

<210> SEQ ID NO 45
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gatatccaga tgacccagtc acccagcagc gtctctgcct ccgttggcga ccgcgtcacg       60
attacgtgca gggctagtca ggggatttat tcctggctcg cctggtacca acagaaacct      120
ggcaaagctc ctaacttgct catatatact gctagcactc tgcaatcagg tgtgccgagt      180
cgattttccg ggagcggttc cggcaccgat tttaccctga caatctcatc ccttcagccc      240
gaagattttg ccacctacta ctgccagcag gctaacatct ccctctcac cttcggtggg       300 ggaaccaaag tagaaatcaa gagg                                             324
```

<210> SEQ ID NO 46
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg
            100                 105

<210> SEQ ID NO 48
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Gly Tyr
             20                  25                  30
Tyr Met His Trp Val Arg Gln Ala Pro Gly Gln Gly Leu Glu Trp Met
         35                  40                  45
Gly Trp Ile Asn Pro Asp Ser Gly Gly Thr Asn Tyr Ala Gln Lys Phe
     50                  55                  60
Gln Gly Arg Val Thr Met Thr Arg Asp Thr Ser Ile Ser Thr Ala Tyr
 65                  70                  75                  80
Met Glu Leu Asn Arg Leu Arg Ser Asp Asp Thr Ala Val Tyr Tyr Cys
                 85                  90                  95
Ala Arg Asp Gln Pro Leu Gly Tyr Cys Thr Asn Gly Val Cys Ser Tyr
             100                 105                 110
Phe Asp Tyr Trp Gly Gln Gly Thr Leu Val Thr Val Ser Ser Ala Ser
         115                 120                 125
Thr Lys Gly Pro Ser Val Phe Pro Leu Ala Pro Ser Ser Lys Ser Thr
     130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                 165                 170                 175
His Thr Phe Pro Ala Val Leu Gln Ser Ser Gly Leu Tyr Ser Leu Ser
             180                 185                 190
Ser Val Val Thr Val Pro Ser Ser Ser Leu Gly Thr Gln Thr Tyr Ile
         195                 200                 205
Cys Asn Val Asn His Lys Pro Ser Asn Thr Lys Val Asp Lys Lys Val
     210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                 245                 250                 255
Lys Asp Thr Leu Met Ile Ser Arg Thr Pro Glu Val Thr Cys Val Val
             260                 265                 270
Val Asp Val Ser His Glu Asp Pro Glu Val Lys Phe Asn Trp Tyr Val
         275                 280                 285
Asp Gly Val Glu Val His Asn Ala Lys Thr Lys Pro Arg Glu Glu Gln
     290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                 325                 330                 335
Leu Pro Ala Pro Ile Glu Lys Thr Ile Ser Lys Ala Lys Gly Gln Pro
             340                 345                 350
Arg Glu Pro Gln Val Tyr Thr Leu Pro Pro Ser Arg Glu Glu Met Thr
         355                 360                 365
Lys Asn Gln Val Ser Leu Thr Cys Leu Val Lys Gly Phe Tyr Pro Ser
     370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                 405                 410                 415
Ser Lys Leu Thr Val Asp Lys Ser Arg Trp Gln Gln Gly Asn Val Phe
```

<210> SEQ ID NO 49
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 50
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
```

(preceding continued content:)

```
                420                 425                 430
Ser Cys Ser Val Met His Glu Ala Leu His Asn His Tyr Thr Gln Lys
        435                 440                 445

Ser Leu Ser Leu Ser Pro Gly Lys
    450                 455
```

-continued

```
                35                  40                  45
Gly Trp Ile Asn Pro Asp Ser Gly Gly Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Asn Arg Leu Arg Ser Asp Asp Thr Ala Val Tyr Tyr Cys
                 85                  90                  95
Ala Arg Asp Gln Pro Ala Gly Ala Cys Thr Ala Gly Ala Cys Ser Tyr
                100                 105                 110
Phe Asp Tyr Trp Gly Gln Gly Thr Leu Val Thr Val Ser Ser Ala Ser
                115                 120                 125
Thr Lys Gly Pro Ser Val Phe Pro Leu Ala Pro Ser Ser Lys Ser Thr
130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
                180                 185                 190
Ser Val Val Thr Val Pro Ser Ser Ser Leu Gly Thr Gln Thr Tyr Ile
                195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
                260                 265                 270
Val Asp Val Ser His Glu Asp Pro Glu Val Lys Phe Asn Trp Tyr Val
                275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
                340                 345                 350
Arg Glu Pro Gln Val Tyr Thr Leu Pro Pro Ser Arg Glu Glu Met Thr
                355                 360                 365
Lys Asn Gln Val Ser Leu Thr Cys Leu Val Lys Gly Phe Tyr Pro Ser
                370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
                435                 440                 445
Ser Leu Ser Leu Ser Pro Gly Lys
                450                 455
```

<210> SEQ ID NO 51
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Ala Cys Thr Ala Gly Ala Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
```

```
                355                 360                 365
Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455

<210> SEQ ID NO 52
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Ala Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255
```

-continued

```
Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 53
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Ala Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160
```

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 54
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe

```
            50                  55                  60
Gln Gly Arg Val Thr Met Thr Arg Asp Thr Ser Ile Ser Thr Ala Tyr
 65                  70                  75                  80
Met Glu Leu Asn Arg Leu Arg Ser Asp Thr Ala Val Tyr Tyr Cys
                 85                  90                  95
Ala Arg Asp Gln Pro Leu Gly Tyr Cys Thr Ala Gly Val Cys Ser Tyr
                100                 105                 110
Phe Asp Tyr Trp Gly Gln Gly Thr Leu Val Thr Val Ser Ser Ala Ser
                115                 120                 125
Thr Lys Gly Pro Ser Val Phe Pro Leu Ala Pro Ser Ser Lys Ser Thr
                130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
                180                 185                 190
Ser Val Val Thr Val Pro Ser Ser Ser Leu Gly Thr Gln Thr Tyr Ile
                195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
                260                 265                 270
Val Asp Val Ser His Glu Asp Pro Glu Val Lys Phe Asn Trp Tyr Val
                275                 280                 285
Asp Gly Val Glu Val His Asn Ala Lys Thr Lys Pro Arg Glu Glu Gln
                290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
                340                 345                 350
Arg Glu Pro Gln Val Tyr Thr Leu Pro Pro Ser Arg Glu Glu Met Thr
                355                 360                 365
Lys Asn Gln Val Ser Leu Thr Cys Leu Val Lys Gly Phe Tyr Pro Ser
                370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
                435                 440                 445
Ser Leu Ser Leu Ser Pro Gly Lys
                450                 455

<210> SEQ ID NO 55
```

<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Thr Ala Val Tyr Tyr Cys
                85                  90                  95

Ala Arg Asp Gln Pro Leu Gly Ala Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
```

```
                 370                 375                 380
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 56
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Ala Gly Ala Cys Thr Ala Gly Ala Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270
```

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Trp Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
            450                 455

<210> SEQ ID NO 57
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

```
His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Ser Cys Ala Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 58
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
```

65                  70                  75                  80
Met Glu Leu Asn Arg Leu Arg Ser Asp Asp Thr Ala Val Tyr Tyr Cys
                    85                  90                  95

Ala Arg Asp Gln Pro Ala Gly Ala Cys Thr Ala Gly Ala Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 59
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr

```
                385                 390                 395                 400
Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 60
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Asp Met Arg Val Pro Ala Gln Leu Leu Gly Leu Leu Leu Leu Trp
1               5                   10                  15

Phe Pro Gly Ser Arg Cys
            20

<210> SEQ ID NO 61
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg

<210> SEQ ID NO 62
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Ser Gly Gly
1               5

<210> SEQ ID NO 64
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190
```

```
Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
    210                 215                 220

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Glu Phe Gly Leu Ser Trp Leu Phe Leu Val Ala Ile Leu Lys Gly
1               5                   10                  15

Val Gln Cys

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115

<210> SEQ ID NO 67
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Lys Thr His Thr
1               5

<210> SEQ ID NO 69
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Cys Pro Pro Cys Pro Ala Pro Glu Leu Leu Gly Gly Pro Ser Val Phe
1               5                  10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 70
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg
            100                 105

<210> SEQ ID NO 71
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 72
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Gln Ile Val Leu Thr Gln Ser Pro Ala Ile Met Ser Ala Ser Pro
        115                 120                 125

Gly Glu Lys Val Thr Met Thr Cys Arg Ala Ser Ser Ser Val Ser Tyr
    130                 135                 140

Met Asn Trp Tyr Gln Gln Lys Ser Gly Thr Ser Pro Lys Arg Trp Ile
145                 150                 155                 160

Tyr Asp Thr Ser Lys Val Ala Ser Gly Val Pro Tyr Arg Phe Ser Gly
                165                 170                 175

Ser Gly Ser Gly Thr Ser Tyr Ser Leu Thr Ile Ser Ser Met Glu Ala
            180                 185                 190

Glu Asp Ala Ala Thr Tyr Tyr Cys Gln Gln Trp Ser Ser Asn Pro Leu
        195                 200                 205

Thr Phe Gly Ser Gly Thr Lys Leu Glu Ile Asn Arg
    210                 215                 220

<210> SEQ ID NO 73
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Gln Val
        115                 120                 125

Gln Leu Gln Gln Ser Gly Ala Glu Leu Ala Arg Pro Gly Ala Ser Val
    130                 135                 140

Lys Met Ser Cys Lys Ala Ser Gly Tyr Thr Phe Thr Arg Tyr Thr Met
145                 150                 155                 160

```
His Trp Val Lys Gln Arg Pro Gly Gln Gly Leu Glu Trp Ile Gly Tyr
            165                 170                 175

Ile Asn Pro Ser Arg Gly Tyr Thr Asn Tyr Asn Gln Lys Phe Lys Asp
            180                 185                 190

Lys Ala Thr Leu Thr Thr Asp Lys Ser Ser Thr Ala Tyr Met Gln
            195                 200                 205

Leu Ser Ser Leu Thr Ser Glu Asp Ser Ala Val Tyr Tyr Cys Ala Arg
            210                 215                 220

Tyr Tyr Asp Asp His Tyr Cys Leu Asp Tyr Trp Gly Gln Gly Thr Thr
225                 230                 235                 240

Leu Thr Val Ser Ser
            245

<210> SEQ ID NO 74
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
            35                  40                  45

Tyr His Gly Thr Asn Leu Asp Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Thr Val Ala Ala Pro
            100                 105                 110

Ser Val Phe Ile Phe Pro Pro Asp Ala Gln Val Thr Gln Ser Pro Ser
            115                 120                 125

Ser Leu Ser Ala Ser Val Gly Asp Arg Val Thr Ile Thr Cys Arg Ser
    130                 135                 140

Ser Thr Gly Ala Val Thr Thr Ser Asn Tyr Ala Asn Trp Val Gln Glu
145                 150                 155                 160

Lys Pro Gly Lys Leu Phe Lys Gly Leu Ile Gly Gly Thr Asn Lys Arg
                165                 170                 175

Ala Pro Gly Val Pro Ser Arg Phe Ser Gly Ser Gly Ser Gly Thr Asp
            180                 185                 190

Ala Thr Leu Thr Ile Ser Ser Leu Gln Pro Glu Asp Phe Ala Thr Tyr
            195                 200                 205

Phe Cys Ala Leu Trp Tyr Ser Asn Leu Trp Val Phe Gly Gly Gly Thr
    210                 215                 220

Lys Val Glu Ile Lys Arg
225                 230

<210> SEQ ID NO 75
<211> LENGTH: 247
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 75

Gln Val Gln Leu Gln Glu Ser Gly Pro Gly Leu Val Lys Pro Ser Gln
1               5                   10                  15
Thr Leu Ser Leu Thr Cys Thr Val Ser Gly Tyr Ser Ile Ser Ser Asp
            20                  25                  30
Phe Ala Trp Asn Trp Ile Arg Gln Pro Pro Gly Lys Gly Leu Glu Trp
        35                  40                  45
Met Gly Tyr Ile Ser Tyr Ser Gly Asn Thr Arg Tyr Gln Pro Ser Leu
    50                  55                  60
Lys Ser Arg Ile Thr Ile Ser Arg Asp Thr Ser Lys Asn Gln Phe Phe
65                  70                  75                  80
Leu Lys Leu Asn Ser Val Thr Ala Ala Asp Thr Ala Thr Tyr Tyr Cys
                85                  90                  95
Val Thr Ala Gly Arg Gly Phe Pro Tyr Trp Gly Gln Gly Thr Leu Val
            100                 105                 110
Thr Val Ser Ser Ala Ser Thr Lys Gly Pro Glu Val Gln Leu Val Glu
        115                 120                 125
Ser Gly Gly Gly Leu Val Gln Pro Gly Gly Ser Leu Arg Leu Ser Cys
    130                 135                 140
Ala Ala Ser Gly Phe Thr Phe Ser Thr Tyr Ala Met Asn Trp Val Arg
145                 150                 155                 160
Gln Ala Pro Gly Lys Gly Leu Glu Trp Val Gly Arg Ile Arg Ser Lys
                165                 170                 175
Tyr Asn Asn Tyr Ala Thr Tyr Tyr Ala Asp Ser Val Lys Asp Arg Phe
            180                 185                 190
Thr Ile Ser Arg Asp Asp Ser Lys Asn Thr Ala Tyr Leu Gln Met Asn
        195                 200                 205
Ser Leu Arg Ala Glu Asp Thr Ala Val Tyr Tyr Cys Thr Arg His Gly
    210                 215                 220
Asn Phe Gly Asn Ser Tyr Val Ser Trp Phe Ala Tyr Trp Gly Gln Gly
225                 230                 235                 240
Thr Leu Val Thr Val Ser Ser
                245

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Ser Thr Lys Gly Pro Ser Val Phe Pro Leu Ala Pro
1               5                   10

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

```
Ala Ser Thr Lys Gly Pro
1               5

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Val Ala Ala Pro Ser Val Phe Ile Phe Pro Pro
1               5                   10

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Val Ala Ala Pro
1               5

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Lys Thr Thr Pro Lys Leu Glu Glu Gly Glu Phe Ser Glu Ala Arg
1               5                   10                  15

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Lys Thr Thr Pro Lys Leu Glu Glu Gly Glu Phe Ser Glu Ala Arg
1               5                   10                  15
Val

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Lys Thr Thr Pro Lys Leu Gly Gly
1               5

<210> SEQ ID NO 83
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Ala Lys Thr Thr Pro Lys Leu Gly Gly
1               5                   10

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Ala Lys Thr Thr Pro
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ala Asp Ala Ala Pro
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Asp Ala Ala Pro Thr Val Ser
1               5

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Asp Ala Ala Ala Ala Gly Gly Pro Gly Ser
1               5                   10

<210> SEQ ID NO 88
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ala Asp Ala Ala Ala Ala Gly Gly Gly Gly Ser Gly Gly Gly Gly
```

```
                1               5                   10                  15
Ser Gly Gly Gly Gly Ser Gly Gly Gly Ser
                20                  25

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Ala Lys Thr Thr Pro Lys Leu Glu Glu Gly Glu Phe Ser Glu Ala
1               5                   10                  15

Arg Val

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Asp Ala Ala Pro
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Asp Ala Ala Pro Thr Val Ser Ile Phe Pro Pro
1               5                   10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Pro Lys Ala Ala Pro
1               5

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Pro Lys Ala Ala Pro Ser Val Thr Leu Phe Pro Pro
1               5                   10

<210> SEQ ID NO 94
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Lys Thr Thr Pro Pro
1               5

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Lys Thr Thr Pro Pro Ser Val Thr Pro Leu Ala Pro
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Lys Thr Thr Ala Pro
1               5

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Lys Thr Thr Ala Pro Ser Val Tyr Pro Leu Ala Pro
1               5                   10

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Gly Ser Gly Gly Gly Ser Gly Gly Gly Gly Ser
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

Gly Glu Asn Lys Val Glu Tyr Ala Pro Ala Leu Met Ala Leu Ser
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Pro Ala Lys Glu Leu Thr Pro Leu Lys Glu Ala Lys Val Ser
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly His Glu Ala Ala Ala Val Met Gln Val Gln Tyr Pro Ala Ser
1               5                   10                  15

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Gly Ser
1               5

MONOVALENT BINDING PROTEINS

RELATED APPLICATIONS

This application claims priority to U.S. Provisional Patent Applications U.S. Ser. No. 61/746,615, filed Dec. 28, 2012 and U.S. Ser. No. 61/755,288, filed Jan. 22, 2013, both entitled "Monovalent Binding Proteins". The contents of the aforementioned applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 24, 2014, is named 553458 (BBI-391)_SL.txt and is 215,256 bytes in size.

FIELD OF THE INVENTION

This disclosure relates to monovalent binding proteins. More particularly, modified antibodies that bind to each of their target antigen via one binding domain is disclosed.

BACKGROUND

Target-binding proteins that possess preferable pharmacodynamic and pharmcokinetic features have attracted more and more attention in the development of biologic therapeutics. Substantial amount of efforts has been dedicated to the optimization of the amino acid sequences of immunoglobulin (e.g., antibody amino acid sequences) in order to obtain immunoglobulins have superior therapeutic effects. These modified immunoglobulins may have different structures and properties from those found in naturally existing immunoglobulins. These modified structures and properties may lead to the superior therapeutic effects achieved by these immunoglobulins.

An immunoglobulin is an ideal platform for drug development because of its various desirable intrinsic properties. For instance, immunoglobulins typically have great target specificity, superior biostability and bioavailability, less toxicity, and sufficient target binding affinity to maximize therapeutic effects. However, neutralizing certain targets such as cell-surface receptors with regular bivalent immunoglobulins has been challenging due to potential unexpected consequences induced by specific molecular mechanism in signal transduction. For example, a large number of CD40 antibodies stimulate, rather than inhibit, B cell proliferation (Adams A B et al J Immunol 2005, 174: 542-550. Malmborg Hager A C et al. Scand J Immunol 2003, 517: 517-523). Targeting CD28 on T cell surface with antibody JJ316 and 5.11 elicited a super-agonistic effect presumably by crosslinking neighboring CD28 homodimers to form large scale lattice structure (Hunig T et al, Immunol Letters 2005, 100: 21-28).

Monovalent antibodies do not typically exhibit the "crosslinking" effect as achieved by multivalent antibodies. Nevertheless, monovalent antibodies have not been regarded as desirable therapeutics because certain inherent features in their structure/architecture may limit their application. For example, a monovalent antibody in Fab form has been shown to have inferior pharmacodynamics (e.g., it is unstable in vivo and rapidly clear following administration). Furthermore, as compared with their multivalent counterparts, monovalent immunoglobulins generally have lower apparent binding affinity due to the absence of avidity binding effects.

In recent years, full length immunoglobulin form has been the immunoglobulin of choice for many immuno-therapeutics, which is likely due to its biostability in vivo. Monovalent immunoglobulin may be acceptable where biostability is not as critical a factor for therapeutic efficacy as bioavailability. For example, due in part to superior tissue penetration as compared to full length antibodies, monovalent Fab antibodies may be better vehicles for delivery of heterologous molecules such as toxins to target cells or tissues. See, e.g., U.S. Pat. No. 5,169,939, incorporated herein by reference. Other examples where monovalent antibodies are being developed as therapeutics include settings where monovalency is critical for obtaining a therapeutic effect. For instance, monovalency may be preferred when bivalency of an antibody may induce a target cell to undergo antigenic modulation. Examples of such antibodies are described in Cobbold and Waldmann (1984) Nature 308: 460-462; EP Patent No. 0131424; Glennie and Stevenson (1982) Nature 295:712-714; Nielsen and Routledge (2002) Blood 100:4067-4073; Stevenson et al. (1989) Anticancer Drug Des. 3(4):219-230; Routledge et al. (1995) Transplant. 605347-853; Clark et al. (1989) Eur. J. Immunol. 19:381-388; Bolt et al. (1993) Eur. J. Immunol. 23:403-411; Routledge et al. (1991) Eur. J. Immunol. 21:2717-2725; Staerz et al. (1985) Nature 314:628-631; and U.S. Pat. No. 5,968,509.

Notably, these monovalent antibody fragments contain functional dimeric Fc sequences, which are included because their effector functions (e.g., complement-mediated lysis of T cells) are needed for therapeutic function. The art has not recognized a need or utility for including an Fc region in monovalent antibodies that are used and/or developed as therapeutics. The reluctance to include an Fc region in monovalent antibodies where the Fc region is not necessary for therapeutic function is underscored by the practical difficulties of obtaining such antibodies. Existing antibody production technology does not provide an efficient method for obtaining large quantities of sufficiently purified heterodimers comprising a single antigen binding component (i.e., monovalency) and an Fc region.

Several approaches have been tested to increase the in vivo stability of immunoglobulin fragments. For example, a Fab fragment may be attached to stability moieties such as polyethylene glycol or other stabilizing molecules such as heterologous peptides. See, e.g., Dennis et al. (2002) J. Biol. Chem. 277:35035-35043; PCT Publication No. WO/01145746, each incorporated herein by reference. An anti c-Met monovalent molecule MetMAb with a Fab-Fc/Fc structure is in clinical trial for non-small cell lung cancer. See PCT Publication No. WO2005063816, incorporated herein by reference. An Fc fragment has been connected to C-terminus of light chain, then coupled with full a heavy chain to achieve monovalent binding to antigen. See PCT Publication No. WO20070105199, incorporated herein by reference. Monovalent binding may also be achieved by replacing IgG1 backbone with IgG4 one. See PCT Publication No. WO2007059782, incorporated herein by reference. The latter showed very weak CH3-mediated dimerization.

U.S. Pat. Nos. 8,258,268 and 7,612,181 provide a novel family of binding proteins capable of binding two or more antigens with high affinity, called the dual variable domain binding protein (DVD binding protein) or Dual Variable Domain Immunoglobulin (DVD-Ig™) construct.

Described here for the first time is a functional class of monovalent binding proteins. More specifically, a class of monovalent antibodies (also referred to as "Mbody" or "monobody") is disclosed wherein one binding arm has been rendered non-functional. In another aspect, monobody having a Fab fragment (also referred to as "Fab-body") is disclosed wherein an Fc region is engineered to be attached to the Fab fragment.

SUMMARY

This disclosure provides monovalent binding proteins capable of binding proteins, such as antigens. More particularly, a class of antibodies is disclosed wherein one binding arm has been rendered non-functional. In one aspect, the antibodies of the present disclosure possess only one functional arm capable of binding a ligand. In another aspect, the one functional arm may have one or more binding domains for binding to different ligands. The ligand may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and combinations thereof.

In one embodiment, a binding protein containing four polypeptide chains is disclosed, wherein at least one (e.g., one or two) of the four polypeptide chains comprise VDH-(X1)n-C—(X2)n. In one aspect, VDH is a heavy chain variable domain, X1 is a linker with the proviso that it is not CH1, C is a heavy chain constant domain, X2 is an Fc region, and n is 0 or 1. At least one of the other two (e.g., one or two) of the four polypeptide chains comprise VDL-(X3)n-C—(X4)n, wherein VDL is a light chain variable domain, X3 is a linker with the proviso that it is not CH1, C is a light chain constant domain, X4 does not comprise an Fc region, and n is 0 or 1. In another aspect, at least one of the four polypeptide chains comprises a mutation located in a variable domain, wherein the mutation inhibits the targeted binding between the specific antigen and the mutant binding domain.

The Fc regions of the two polypeptide chains that have a formula of VDH-(X1)n-C—(X2)n may each contain a mutation, wherein the mutations on the two Fc regions enhance heterodimerization of the two polypeptide chains. In one aspect, knobs-into-holes mutations may be introduced into these Fc regions to achieve heterodimerization of the Fc regions. See Atwell et al. J. Mol. Biol. 1997, 270: 26-35.

In another embodiment, one of the four polypeptide chains has a sequence identical to a polypeptide chain selected from the group consisting of SEQ ID Nos. 13-18.

In another embodiment, a binding protein comprising four polypeptide chains is disclosed wherein, two of the four polypeptide chains comprise VDH1-(X1)n-VDH2-C—(X2)n, wherein VDH1 is a first heavy chain variable domain, VDH2 is a second heavy chain variable domain, C is a heavy chain constant domain, X1 is a linker with the proviso that it is not CH1, X2 is an Fc region, and n is 0 or 1. In another aspect, two of the four polypeptide chains comprise VDL1-(X3)n-VDL2-C—(X4)n, wherein VDL1 is a first light chain variable domain, VDL2 is a second light chain variable domain, C is a light chain constant domain, X3 is a linker with the proviso that it is not CH1, X4 does not comprise an Fc region and n is 0 or 1. In certain embodiments, the VDL1 and VDH1 domains form an antigen binding domain for a first target antigen and the VDL2 and VDH2 domains for a second antigen binding domain for a second target antigen. In another aspect, at least one of the four polypeptide chains comprises a mutation, said mutation being located in the first variable domain or the second variable domain, wherein said mutation inhibits the targeted binding between the specific antigen and the mutant binding domain. The mutation may be located on the first heavy chain variable domain (VDH1) or the second heavy chain variable domain (VDH2). Alternatively, the mutation may be located on the first light chain variable domain (VDL1) or the second light chain variable domain (VDL2). Although single, or dual variable domain formula are used here for purpose of illustration, the binding proteins of this disclosure may contain one, two (DVD), three (TVD), or more variable domains.

In another embodiment, at least one of the four polypeptide chains comprises two mutations, one mutation being located in the first variable domain (e.g., VDL1 or VDH1) and the other mutation being located in the second variable domain (e.g., VDL2 or VDH2) or the polypeptide chain, wherein the two mutations inhibit the targeted binding between the two mutant binding domains and their respective specific antigens.

In another embodiment, the Fc region of the two polypeptide chains having a formula of VDH1-(X1)n-VDH2-C—(X2)n each comprises a mutation, wherein the mutations on the two Fc regions enhance heterodimerization of the two polypeptide chains. By way of example, to generate cMet monovalent antibodies, knobs-into-holes mutations may be introduced into HC construct to achieve heterodimerization of HCs. See Atwell et al. J. Mol. Biol. 1997, 270: 26-35.

In another embodiment, a binding protein comprising a first polypeptide chain and a second polypeptide chain is disclosed, wherein the first polypeptide chain comprises VDH-(X1)n-X2-(X3)m-Y1, and the VDH is a heavy chain variable domain, X1 is a linker with the proviso that X1 is not CH1, X2 is CH1, X3 is a linker, Y1 is a CH2-CH3 or CH3 or part of CH3, n is 0 or 1, and m is 0 or 1. The second polypeptide may contain VDL-(X4)n-X5-(X6)m-Y2, wherein VDL is a light chain variable domain, X4 is a linker with the proviso that X4 is not CH1, X5 is CL1, X6 is a linker, Y2 is a CH2-CH3 or CH3 or part of CH3, n is 0 or 1, and m is 0 or 1. In aspect, Y1 and Y2 may each comprises a mutation, wherein the mutations on Y1 and Y2 enhance the interaction between Y1 and Y2. By way of example, knobs-into-holes mutations may be introduced into HC construct to achieve heterodimerization of HCs. See Atwell et al. J. Mol. Biol. 1997, 270: 26-35.

By way of example and as one embodiment, VDH is SEQ ID No. 25, and VDL is SEQ ID No. 20. In another embodiment, X2 is SEQ ID No. 26, and X5 is SEQ ID No. 21. In another embodiment, X3 is SEQ ID No. 27, and X6 is SEQ ID No. 22. In another aspect, Y1 is SEQ ID No. 28, and Y2 is SEQ ID No. 23. In another aspect, the first polypeptide chain may further comprise a signal peptide of SEQ ID No. 24. In another aspect, the second polypeptide chain further comprises a signal peptide of SEQ ID No. 19.

A binding protein is also disclosed which comprises a first polypeptide chain and a second polypeptide chain, wherein the first polypeptide chain comprises VDH1-(X1)n-VDH2-X2-(X3)m-Y1. In one aspect, VDH1 is a first heavy chain variable domain, X1 is a linker with the proviso that X1 is not CH1, VDH2 is a second heavy chain variable domain, X2 is CH1, X3 is a linker, Y1 is a CH2-CH3 or CH3 or part of CH3, n is 0 or 1, m is 0 or 1. In one embodiment, the second polypeptide comprises VDL1-(X4)n-VDL2-X5-(X6)m-Y2, wherein VDL1 is a first light chain variable domain, X4 is a linker with the proviso that X4 is not CH1, VDL2 is a second light chain variable domain, X5 is CL1, X6 is a linker, Y2 is a CH2-CH3 or CH3 or part of CH3, n is 0 or 1, and m is 0 or 1. In one aspect, Y1 and Y2 may each contain a mutation, wherein the mutations on Y1 and Y2 together may enhance the interaction between Y1 and Y2.

Examples of such mutations may include but are not limited to the knobs-into-holes mutations as described in Atwell et al. J. Mol. Biol. 1997, 270: 26-35. In one embodiment, Y1 is SEQ ID No. 28, and Y2 is SEQ ID No. 23. In another embodiment, X2 is SEQ ID No. 26, and X5 is SEQ ID No. 21, X3 is SEQ ID No. 27, and X6 is SEQ ID No. 22.

In one embodiment, the binding protein has an on rate constant ($K_{on}$) to one or more targets of at least about $10^2 M^{-1} s^{-1}$; at least about $10^3 M^{-1} s^{-1}$; at least about $10^4 M^{-1} s^{-1}$; at least about $10^5 M^{-1} s^{-1}$; or at least about $10^6 M^{-1} s^{-1}$, as measured by surface plasmon resonance. In an embodiment, the binding protein has an on rate constant ($K_{on}$) to one or more targets from about $10^2 M^{-1} s^{-1}$ to about $10^3 M^{-1} s^{-1}$; from about $10^3 M^{-1} s^{-1}$ to about $10^4 M^{-1} s^{-1}$; from about $10^4 M^{-1} s^{-1}$ to about $10^5 M^{-1} s^{-1}$; or from about $10^5 M^{-1} s^{-1}$ to about $10^6 M^{-1} s^{-1}$, as measured by surface plasmon resonance.

In another embodiment, the binding protein has an off rate constant ($K_{off}$) for one or more targets of at most about $10^{-3} s^{-1}$; at most about $10^{-4} s^{-1}$; at most about $10^{-5} s^{-1}$; or at most about $10^{-6} s^{-1}$, as measured by surface plasmon resonance. In an embodiment, the binding protein has an off rate constant ($K_{off}$) to one or more targets of about $10^{-3} s^{-1}$ to about $10^{-4} s^{-1}$; of about $10^{-4} s^{-1}$ to about $10^{-5} s^{-1}$; or of about $10^{-5} s^{-1}$ to about $10^{-6} s^{-1}$, as measured by surface plasmon resonance.

In another embodiment, the binding protein has a dissociation constant ($K_d$) to one or more targets of at most about $10^{-7} M$; at most about $10^{-8} M$; at most about $10^{-9} M$; at most about $10^{-10} M$; at most about $10^{-11} M$; at most about $10^{-12} M$; or at most $10^{-13} M$. In an embodiment, the binding protein has a dissociation constant ($K_d$) to its targets of about $10^{-7} M$ to about $10^{-8} M$; of about $10^{-8} M$ to about $10^{-9} M$; of about $10^{-9} M$ to about $10^{-10} M$; of about $10^{-10} M$ to about $10^{-11} M$; of about $10^{-11} M$ to about $10^{-12} M$; or of about $10^{-12}$ to M about $10^{-13} M$.

In another embodiment, the binding protein is a conjugate further comprising an agent. In an embodiment, the agent is an immunoadhesion molecule, an imaging agent, a therapeutic agent, or a cytotoxic agent. In an embodiment, the imaging agent is a radiolabel, an enzyme, a fluorescent label, a luminescent label, a bioluminescent label, a magnetic label, or biotin. In another embodiment, the radiolabel is $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$. In yet another embodiment, the therapeutic or cytotoxic agent is an anti-metabolite, an alkylating agent, an antibiotic, a growth factor, a cytokine, an anti-angiogenic agent, an anti-mitotic agent, an anthracycline, toxin, or an apoptotic agent.

In another embodiment, the binding protein is a crystallized binding protein and exists as a crystal. In an embodiment, the crystal is a carrier-free pharmaceutical controlled release crystal. In another embodiment, the crystallized binding protein has a greater half life in vivo than the soluble counterpart of the binding protein. In yet another embodiment, the crystallized binding protein retains biological activity.

In another embodiment, the binding protein described herein is glycosylated. For example, the glycosylation pattern is a human glycosylation pattern.

An isolated nucleic acid encoding any one of the binding proteins disclosed herein is also provided. A further embodiment provides a vector comprising the isolated nucleic acid disclosed herein wherein the vector is pcDNA; pTT (Durocher et al. (2002) Nucleic Acids Res. 30(2); pTT3 (pTT with additional multiple cloning site); pEFBOS, see Mizushima and Nagata (1990) Nucleic Acids Res. 18(17); pBV; pJV; pcDNA3.1 TOPO; pEF6 TOPO; pBOS; pHybE; or pBJ. In an embodiment, the vector is a vector disclosed in US Patent Publication No. 20090239259.

In another aspect, a host cell is transformed with the vector disclosed herein. In an embodiment, the host cell is a prokaryotic cell, for example, *E. coli*. In another embodiment, the host cell is a eukaryotic cell, for example, a protist cell, an animal cell, a plant cell, or a fungal cell. In an embodiment, the host cell is a mammalian cell including, but not limited to, 293E, CHO, COS, NS0, SP2, PER.C6, or a fungal cell, such as *Saccharomyces cerevisiae*, or an insect cell, such as Sf9. In an embodiment, two or more binding proteins, e.g., with different specificities, are produced in a single recombinant host cell. For example, the expression of a mixture of antibodies has been called Oligoclonics™ (Merus B.V., The Netherlands), see U.S. Pat. Nos. 7,262,028 and 7,429,486.

A method of producing a binding protein disclosed herein comprising culturing any one of the host cells disclosed herein in a culture medium under conditions sufficient to produce the binding protein is provided.

One embodiment provides a composition for the release of a binding protein wherein the composition comprises a crystallized binding protein, an ingredient, and at least one polymeric carrier. In an embodiment, the polymeric carrier is poly(acrylic acid), a poly(cyanoacrylate), a poly(amino acid), a poly(anhydride), a poly(depsipeptide), a poly(ester), poly(lactic acid), poly(lactic-co-glycolic acid) or PLGA, poly(b-hydroxybutryate), poly(caprolactone), poly(dioxanone), poly(ethylene glycol), poly((hydroxypropyl)methacrylamide, poly[(organo)phosphazene], a poly(ortho ester), poly(vinyl alcohol), poly(vinylpyrrolidone), a maleic anhydride-alkyl vinyl ether copolymer, a pluronic polyol, albumin, alginate, cellulose, a cellulose derivative, collagen, fibrin, gelatin, hyaluronic acid, an oligosaccharide, a glycaminoglycan, a sulfated polysaccharide, or blends and copolymers thereof. In an embodiment, the ingredient is albumin, sucrose, trehalose, lactitol, gelatin, hydroxypropyl-β-cyclodextrin, methoxypolyethylene glycol, or polyethylene glycol.

Another embodiment provides a method for treating a mammal comprising the step of administering to the mammal an effective amount of a composition disclosed herein.

A pharmaceutical composition comprising a binding protein disclosed herein and a pharmaceutically acceptable carrier is provided. In a further embodiment, the pharmaceutical composition comprises at least one additional therapeutic agent for treating a disorder. For example, the additional agent may be a therapeutic agent, an imaging agent, a cytotoxic agent, an angiogenesis inhibitor (including but not limited to an anti-VEGF antibody or a VEGF-trap), a kinase inhibitor (including but not limited to a KDR and a TIE-2 inhibitor), a co-stimulation molecule blocker (including but not limited to anti-B7.1, anti-B7.2, CTLA4-Ig, anti-CD20), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, and an anti-IL-6/cytokine receptor antibody), methotrexate, cyclosporin, rapamycin, FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

A method for treating a human subject suffering from a disorder in which the target, or targets, capable of being bound by the binding protein disclosed herein is detrimental, comprising administering to the human subject a binding protein disclosed herein such that the activity of the target, or targets, in the human subject is inhibited and one or more symptoms is alleviated or treatment is achieved is provided. The binding proteins provided herein can be used to treat humans suffering from autoimmune diseases such as, for example, those associated with inflammation. In an embodiment, the binding proteins provided herein or antigen-binding portions thereof, are used to treat asthma, allergies, allergic lung disease, allergic rhinitis, atopic dermatitis, chronic obstructive pulmonary disease (COPD), fibrosis, cystic fibrosis (CF), fibrotic lung disease, idiopathic pulmonary fibrosis, liver fibrosis, lupus, hepatitis B-related liver diseases and fibrosis, sepsis, systemic lupus erythematosus (SLE), glomerulonephritis, inflammatory skin diseases, psoriasis, diabetes, insulin dependent diabetes mellitus, infectious diseases caused by HIV, inflammatory bowel disease (IBD), ulcerative colitis (UC), Crohn's disease (CD), rheumatoid arthritis (RA), osteoarthritis (OA), multiple sclerosis (MS), graft-versus-host disease (GVHD), transplant rejection, ischemic heart disease (IHD), celiac disease, contact hypersensitivity, alcoholic liver disease, Behcet's disease, atherosclerotic vascular disease, occular surface inflammatory diseases, or Lyme disease.

In another embodiment, the disorder or condition to be treated comprises the symptoms caused by viral infection in a human which is caused by, for example, HIV, the human rhinovirus, an enterovirus, a coronavirus, a herpes virus, an influenza virus, a parainfluenza virus, a respiratory syncytial virus or an adenovirus.

The binding proteins provided herein can be used to treat neurological disorders. In an embodiment, the binding proteins provided herein, or antigen-binding portions thereof, are used to treat neurodegenerative diseases and conditions involving neuronal regeneration and spinal cord injury.

In an embodiment, diseases that can be treated or diagnosed with the compositions and methods disclosed herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

Another embodiment provides for the use of the binding protein in the treatment of a disease or disorder, wherein said disease or disorder is rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, Addison's disease, sporadic, polyglandular deficiency type I and polyglandular deficiency type II, Schmidt's syndrome, adult (acute) respiratory distress syndrome, alopecia, alopecia greata, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, drug-induced hepatitis, non-alcoholic steatohepatitis, allergy and asthma, group B streptococci (GBS) infection, mental disorders, depression, schizophrenia, Th2 Type and Th1 Type mediated diseases, acute and chronic pain, different forms of pain, cancers, lung cancer, breast cancer, stomach cancer, bladder cancer, colon cancer, pancreatic cancer, ovarian cancer, prostate cancer, rectal cancer, hematopoietic malignancies, leukemia, lymphoma, Abetalipoprotemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic ateriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis A, His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignamt lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, senile dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL telangiectasia, thromboangitis obliterans, thrombocytopenia, toxicity, transplants, trauma/hemorrhage, type III hypersensitivity reactions, type IV hypersensitivity, unstable angina, uremia, urosepsis, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, anaphylaxis, anti-phospholipid antibody syndrome, aplastic anemia, atopic eczema, atopic dermatitis, autoimmune dermatitis, autoimmune disorder associated with streptococcus infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (cis) with risk for multiple sclerosis, childhood onset psychiatric disorder, dacryocystitis, dermatomyositis, diabetic retinopathy, disk herniation, disk prolaps, drug induced immune hemolytic anemia, endometriosis, endophthalmitis, episcleritis, erythema multiforme, erythema multiforme major, gestational pemphigoid, Guillain-Barré syndrome (GBS), Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell histiocytosis, livedo reticularis, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, poliosis, polyarticular JRA, polyendocrine deficiency syndrome, polymyositis, polymyalgia rheumatica (PMR), primary Parkinsonism, prostatitis, pure red cell aplasia, primary adrenal insufficiency, recurrent neuromyelitis optica, restenosis, rheumatic heart disease, sapho (synovitis, acne, pustulosis, hyperostosis, and osteitis), secondary amyloidosis, shock lung, scleritis, sciatica, secondary adrenal insufficiency, silicone associated connective tissue disease, sneddon-wilkinson dermatosis, spondilitis ankylosans, Stevens-Johnson syndrome (SJS), temporal arteritis, toxoplasmic retinitis, toxic epidermal necrolysis, transverse myelitis, TRAPS (tumor necrosis factor receptor, type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, or wound healing.

In an embodiment, the binding proteins, or antigen-binding portions thereof, are used to treat cancer or in the prevention or inhibition of metastases from the tumors described herein either when used alone or in combination with radiotherapy and/or chemotherapeutic agents.

In another aspect, methods of treating a patient suffering from a disorder comprising the step of administering any one of the binding proteins disclosed herein before, concurrently, or after the administration of a second agent, are provided. In an embodiment, the second agent is budenoside, epidermal growth factor, a corticosteroid, cyclosporin, sulfasalazine, an aminosalicylate, 6-mercaptopurine, azathioprine, metronidazole, a lipoxygenase inhibitor, mesalamine, olsalazine, balsalazide, an antioxidant, a thromboxane inhibitor, an IL-1 receptor antagonist, an anti-IL-1β mAbs, an anti-IL-6 or IL-6 receptor mAb, a growth factor, an elastase inhibitor, a pyridinyl-imidazole compound, an antibody or agonist of TNF, LT, IL-1, IL-2, IL-6, IL-7, IL-8, IL-12, IL-13, IL-15, IL-16, IL-18, IL-23, EMAP-II, GM-CSF, FGF, or PDGF, an antibody to CD2, CD3, CD4, CD8, CD-19, CD25, CD28, CD30, CD40, CD45, CD69, CD90 or a ligand thereof, methotrexate, cyclosporin, FK506, rapamycin, mycophenolate mofetil, leflunomide, an NSAID, ibuprofen, prednisolone, a phosphodiesterase inhibitor, an adenosine agonist, an antithrombotic agent, a complement inhibitor, an adrenergic agent, IRAK, NIK, IKK, p38, a MAP kinase inhibitor, an IL-1β converting enzyme inhibitor, a TNFα-converting enzyme inhibitor, a T-cell signalling inhibitor, a metalloproteinase inhibitor, sulfasalazine, azathioprine, a 6-mercaptopurine, an angiotensin converting enzyme inhibitor, a soluble cytokine receptor, a soluble p55 TNF receptor, a soluble p75 TNF receptor, sIL-1RI, sIL-1RII, sIL-6R, an antiinflammatory cytokine, IL-4, IL-10, IL-11, IL-13, or TGFβ. In a particular embodiment, the pharmaceutical compositions disclosed herein are administered to a patient by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

Anti-idiotype antibodies to the binding proteins disclosed herein are also provided. An anti-idiotype antibody includes any protein or peptide-containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or any portion thereof, that can be incorporated into a binding protein provided herein.

A method of determining the presence, amount or concentration of the target antigen, or fragment thereof, in a test sample is provided. The method comprises assaying the test sample for the antigen, or fragment thereof, by an immunoassay. The immunoassay (i) employs at least one binding protein and at least one detectable label and (ii) comprises comparing a signal generated by the detectable label as a direct or indirect indication of the presence, amount or concentration of the antigen, or fragment thereof, in the test sample to a signal generated as a direct or indirect indication of the presence, amount or concentration of the antigen, or fragment thereof, in a control or a calibrator. The calibrator is optionally part of a series of calibrators in which each of the calibrators differs from the other calibrators in the series by the concentration of the antigen, or fragment thereof. The method may comprise (i) contacting the test sample with at least one capture agent, which binds to an epitope on the antigen, or fragment thereof, so as to form a capture agent/antigen, or fragment thereof, complex, (ii) contacting the capture agent/antigen, or fragment thereof, complex with at least one detection agent, which comprises a detectable label and binds to an epitope on the antigen, or fragment thereof, that is not bound by the capture agent, to form a capture agent/antigen, or fragment thereof/detection agent complex, and (iii) determining the presence, amount or concentration of the antigen, or fragment thereof, in the test sample based on the signal generated by the detectable label in the capture agent/antigen, or fragment thereof/detection agent complex formed in (ii), wherein at least one capture agent and/or at least one detection agent is the at least one binding protein.

Alternatively, the method may include (i) contacting the test sample with at least one capture agent, which binds to an epitope on the antigen, or fragment thereof, so as to form a capture agent/antigen, or fragment thereof, complex, and simultaneously or sequentially, in either order, contacting the test sample with detectably labeled antigen, or fragment thereof, which can compete with any antigen, or fragment thereof, in the test sample for binding to the at least one capture agent, wherein any antigen, or fragment thereof, present in the test sample and the detectably labeled antigen compete with each other to form a capture agent/antigen, or fragment thereof, complex and a capture agent/detectably labeled antigen, or fragment thereof, complex, respectively, and (ii) determining the presence, amount or concentration of the antigen, or fragment thereof, in the test sample based on the signal generated by the detectable label in the capture agent/detectably labeled antigen, or fragment thereof, complex formed in (ii), wherein at least one capture agent is the at least one binding protein and wherein the signal generated by the detectable label in the capture agent/detectably labeled antigen, or fragment thereof, complex is inversely proportional to the amount or concentration of antigen, or fragment thereof, in the test sample.

The test sample may be from a patient, in which case the method may further include diagnosing, prognosticating, or assessing the efficacy of therapeutic/prophylactic treatment of the patient. If the method include assessing the efficacy of therapeutic/prophylactic treatment of the patient, the method optionally further comprises modifying the therapeutic/prophylactic treatment of the patient as needed to improve efficacy. The method may be adapted for use in an automated system or a semi-automated system. Accordingly, the methods described herein also can be used to determine whether or not a subject has or is at risk of developing a given disease, disorder or condition. Specifically, such a method may include the steps of: (a) determining the concentration or amount in a test sample from a subject of analyte, or fragment thereof, (e.g., using the methods described herein, or methods known in the art); and (b) comparing the concentration or amount of analyte, or fragment thereof, determined in step (a) with a predetermined level, wherein, if the concentration or amount of analyte determined in step (a) is favorable with respect to a predetermined level, then the subject is determined not to have or be at risk for a given disease, disorder or condition. However, if the concentration or amount of analyte determined in step (a) is unfavorable with respect to the predetermined level, then the subject is determined to have or be at risk for a given disease, disorder or condition.

Additionally, provided herein is method of monitoring the progression of disease in a subject. Optimally the method may include the steps of: (a) determining the concentration or amount in a test sample from a subject of analyte; (b) determining the concentration or amount in a later test sample from the subject of analyte; and (c) comparing the concentration or amount of analyte as determined in step (b) with the concentration or amount of analyte determined in step (a), wherein if the concentration or amount determined in step (b) is unchanged or is unfavorable when compared to the concentration or amount of analyte determined in step (a), then the disease in the subject is determined to have continued, progressed or worsened. By comparison, if the concentration or amount of analyte as determined in step (b) is favorable when compared to the concentration or amount of analyte as determined in step (a), then the disease in the subject is determined to have discontinued, regressed or improved.

Optionally, the method further comprises comparing the concentration or amount of analyte as determined in step (b), for example, with a predetermined level. Further, optionally the method comprises treating the subject with one or more pharmaceutical compositions for a period of time if the comparison shows that the concentration or amount of analyte as determined in step (b), for example, is unfavorably altered with respect to the predetermined level.

BRIEF DESCRIPTION OF THE DRAWINGS

FIG. 1 shows antigen binding affinity of the monovalent antibodies after inactivation of antigen-binding by VH CDR3 Alanine Scanning.

FIG. 2 shows antigen binding affinity of cMet MBodies having knobs-into-holes mutations.

FIG. 3 is a schematic representation of half-Ig constructs containing different numbers and types of variable domains as well as whole molecules of various parental antibodies.

FIG. 4 illustrate the change in functionality of a c-Met half-Ig.

FIG. 5 shows the functionality of the ERBB2/ERBB2 DVD-Ig and the half-Ig from the DVD-Ig.

FIG. 6 is a schematic representation of additional examples of constructs containing different numbers and types of variable domains by adjusting the valency and specificity of the parental antibodies.

DETAILED DESCRIPTION

Monovalent binding proteins are provided. Specifically, the binding proteins may be a modified antibody with one functional arm for binding to target antigens. The binding proteins and pharmaceutical compositions thereof, as well as nucleic acids, recombinant expression vectors and host cells for making such binding proteins are also provided. Methods of using the disclosed binding proteins to detect specific antigens and/or ligands, either in vitro or in vivo, as well as uses in the prevention, and/or treatment diseases and disorders are also provided.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the disclosure may be more readily understood, select terms are defined below.

The term "ligand", as it is well known and commonly used in the art, refers to any substance capable of binding, or of being bound, to another substance. Similarly, the term "antigen", as it is well known and commonly used in the art, refers to any substance to which an antibody may be generated. Although "antigen" is commonly used in reference to an antibody binding substrate, and "ligand" is often used when referring to receptor binding substrates, these terms are not distinguishing, one from the other, and encompass a wide range of overlapping chemical entities. For the avoidance of doubt, antigen and ligand are used interchangeably throughout herein. Antigens/ligands may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and any combination thereof.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The heavy chain variable region (domain) is also designated as VDH in this disclosure. The CH is comprised of three domains, CH1, CH2 and CH3. Each light chain is comprised of a light chain variable region (VL) and a light chain constant region (CL). The CL is comprised of a single CL domain. The light chain variable region (domain) is also designated as VDL in this disclosure. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

An "affinity matured" antibody is an antibody with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. Affinity matured antibodies are produced by procedures known in the art. Marks et al. (1992) BioTechnology 10:779-783 describes affinity maturation by VH and VL domain shuffling. Random mutagenesis of CDR and/or framework residues is described by Barbas et al. (1994) Proc. Nat. Acad. Sci. USA 91:3809-3813; Schier et al. (1995) Gene 169:147-155; Yelton et al. (1995) J. Immunol. 155:1994-2004; Jackson et al. (1995) J. Immunol. 154(7): 3310-9; Hawkins et al. (1992) J. Mol. Biol. 226:889-896 and mutation at selective mutagenesis positions, contact or hypermutation positions with an activity enhancing amino acid residue as described in U.S. Pat. No. 6,914,128.

The term "CDR-grafted antibody" refers to an antibody that comprises heavy and light chain variable region sequences in which the sequences of one or more of the CDR regions of VH and/or VL are replaced with CDR sequences of another antibody. For example, the two antibodies can be from different species, such as antibodies having murine heavy and light chain variable regions in which one or more of the murine CDRs has been replaced with human CDR sequences.

The term "humanized antibody" refers to an antibody from a non-human species that has been altered to be more "human-like", i.e., more similar to human germline sequences. One type of humanized antibody is a CDR-grafted antibody, in which non-human CDR sequences are introduced into human VH and VL sequences to replace the corresponding human CDR sequences. A "humanized antibody" is also an antibody or a variant, derivative, analog or fragment thereof that comprises framework region (FR) sequences having substantially (e.g., at least 80%, at least 85%, at least 90%, at least 95%, at least 98% or at least 99% identity to) the amino acid sequence of a human antibody and at least one CDR having substantially the amino acid sequence of a non-human antibody. A humanized antibody may comprise substantially all of at least one, and typically two, variable domains (Fab, Fab', F(ab')2, FabC, Fv) in which the sequence of all or substantially all of the CDR regions correspond to those of a non-human immunoglobulin (i.e., donor antibody) and the sequence of all or substantially all of the FR regions are those of a human immunoglobulin. The humanized antibody also may include the CH1, hinge, CH2, CH3, and CH4 regions of the heavy chain. In an embodiment, a humanized antibody also comprises at least a portion of a human immunoglobulin Fc region. In some embodiments, a humanized antibody only contains a humanized light chain. In some embodiments, a humanized antibody only contains a humanized heavy chain. In some embodiments, a humanized antibody only contains a humanized variable domain of a light chain and/or humanized variable domain of a heavy chain. In some embodiments, a humanized antibody contains a light chain as well as at least the variable domain of a heavy chain. In some embodiments, a humanized antibody contains a heavy chain as well as at least the variable domain of a light chain.

The terms "dual variable domain (DVD) binding protein" and "dual variable domain immunoglobulin" refer to a binding protein that has at least two variable domains in each of its one or more binding arms (e.g., a pair of HC/LC) (see PCT Publication No. WO 02/02773). Each variable domain is able to bind to an antigen/ligand. In an embodiment, each variable domain binds different antigens/ligands or epitopes. In another embodiment, each variable domain binds the same antigen/ligand or epitope. In another embodiment, a dual variable domain binding protein has two identical antigen/ligand binding arms, with identical specificity and identical VD sequences, and is bivalent for each antigen to which it binds. In an embodiment, the DVD binding proteins may be monospecific, i.e., capable of binding one antigen/ligand or multispecific, i.e., capable of binding two or more antigens/ligands. DVD binding proteins comprising two heavy chain DVD polypeptides and two light chain DVD polypeptides are referred to as a DVD-Ig™. In an embodiment, each half of a four chain DVD binding protein comprises a heavy chain DVD polypeptide, and a light chain DVD polypeptide, and two variable domain binding sites. In an embodiment, each binding site comprises a heavy chain variable domain and a light chain variable domain with a total of 6 CDRs involved in antigen binding per antigen binding site. In a specific embodiment of the present invention, at least one binding site comprises a receptor binding site, capable of binding one or more receptor ligands.

The term "antiidiotypic antibody" refers to an antibody raised against the amino acid sequence of the antigen combining site of another antibody. Antiidiotypic antibodies may be administered to enhance an immune response against an antigen.

The terms "parent antibody", "parent receptor", or more generically, "parent binding protein" refer to a pre-existing, or previously isolated binding protein from which a functional binding domain is utilized in a novel binding protein construct.

The term "biological activity" refers to any one or more biological properties of a molecule (whether present naturally as found in vivo, or provided or enabled by recombinant means). Biological properties include, but are not limited to, binding a receptor or receptor ligand, inducing cell proliferation, inhibiting cell growth, inducing other cytokines, inducing apoptosis, and enzymatic activity.

The term "neutralizing" refers to counteracting the biological activity of an antigen/ligand when a binding protein specifically binds to the antigen/ligand. In an embodiment, the neutralizing binding protein binds to an antigen/ligand (e.g., a cytokine) and reduces its biologically activity by at least about 20%, 40%, 60%, 80%, 85% or more.

"Specificity" refers to the ability of a binding protein to selectively bind an antigen/ligand.

"Affinity" is the strength of the interaction between a binding protein and an antigen/ligand, and is determined by the sequence of the binding domain(s) of the binding protein as well as by the nature of the antigen/ligand, such as its size, shape, and/or charge. Binding proteins may be selected for affinities that provide desired therapeutic end-points while minimizing negative side-effects. Affinity may be measured using methods known to one skilled in the art (US 20090311253).

The term "potency" refers to the ability of a binding protein to achieve a desired effect, and is a measurement of its therapeutic efficacy. Potency may be assessed using methods known to one skilled in the art (US 20090311253).

The term "cross-reactivity" refers to the ability of a binding protein to bind a target other than that against which it was raised. Generally, a binding protein will bind its target tissue(s)/antigen(s) with an appropriately high affinity, but will display an appropriately low affinity for non-target normal tissues. Individual binding proteins are generally selected to meet two criteria. (1) Tissue staining appropriate for the known expression of the antibody target. (2) Similar staining pattern between human and tox species (mouse and cynomolgus monkey) tissues from the same organ. These and other methods of assessing cross-reactivity are known to one skilled in the art (US 20090311253).

The term "biological function" refers the specific in vitro or in vivo actions of a binding protein. Binding proteins may target several classes of antigens/ligands and achieve desired therapeutic outcomes through multiple mechanisms of action. Binding proteins may target soluble proteins, cell surface antigens, as well as extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve distinct functions in a single binding protein molecule. The in vitro assays and in vivo models used to assess biological function are known to one skilled in the art (US 20090311253).

A "stable" binding protein is one in which the binding protein essentially retains its physical stability, chemical stability and/or biological activity upon storage. A multivalent binding protein that is stable in vitro at various temperatures for an extended period of time is desirable. Methods of stabilizing binding proteins and assessing their stability at various temperatures are known to one skilled in the art (US 20090311253).

The term "solubility" refers to the ability of a protein to remain dispersed within an aqueous solution. The solubility of a protein in an aqueous formulation depends upon the proper distribution of hydrophobic and hydrophilic amino acid residues, and therefore, solubility can correlate with the production of correctly folded proteins. A person skilled in the art will be able to detect an increase or decrease in solubility of a binding protein using routine HPLC techniques and methods known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art (US 20090311253).

The term "immunogenicity" means the ability of a substance to induce an immune response. Administration of a therapeutic binding protein may result in a certain incidence of an immune response. Potential elements that might induce immunogenicity in a multivalent format may be analyzed during selection of the parental binding proteins, and steps to reduce such risk can be taken to optimize the parental binding proteins prior to incorporating their sequences into a multivalent binding protein format. Methods of reducing the immunogenicity of antibodies and binding proteins are known to one skilled in the art (e.g., US 20090311253).

The terms "label" and "detectable label" mean a moiety attached to a member of a specific binding pair, such as an antibody or its analyte to render a reaction (e.g., binding) between the members of the specific binding pair, detectable. The labeled member of the specific binding pair is referred to as "detectably labeled." Thus, the term "labeled binding protein" refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. In this regard, the moiety itself may not be detectably labeled but may become detectable upon reaction with yet another moiety.

The term "conjugate" refers to a binding protein, such as an antibody, that is chemically linked to a second chemical moiety, such as a therapeutic or cytotoxic agent. The term "agent" includes a chemical compound, a mixture of chemical compounds, a biological macromolecule, or an extract made from biological materials. In an embodiment, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The terms "crystal" and "crystallized" refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, CRYSTALLIZATION OF NUCLEIC ACIDS AND PROTEINS, A PRACTICAL APPROACH, 2nd ea., pp. 20 1-16, Oxford University Press, New York, N.Y., (1999).

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Other vectors include RNA vectors. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, other forms of expression vectors are also included, such as viral vectors (e.g., replication defective retroviruses, adenoviruses and adeno-associated viruses), which serve equivalent functions. A group of pHybE vectors (U.S. Patent Application Ser. No. 61/021,282) were used for parental binding protein and monovalent binding protein cloning.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include but are not limited to the prokaryotic cell line *E. Coli*; mammalian cell lines CHO, HEK293, COS, NS0, SP2 and PER.C6; the insect cell line Sf9; and the fungal cell *Saccharomyces cerevisiae*.

The term "transfection" encompasses a variety of techniques commonly used for the introduction of exogenous nucleic acid (e.g., DNA) into a host cell, e.g., electroporation, calcium-phosphate precipitation, DEAE-dextran transfection and the like.

The term "cytokine" refers to a protein released by one cell population that acts on another cell population as an intercellular mediator. The term "cytokine" includes proteins from natural sources or from recombinant cell culture and biologically active equivalents of the native sequence cytokines.

The term "biological sample" means a quantity of a substance from a living thing or formerly living thing. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "component" refers to an element of a composition. In relation to a diagnostic kit, for example, a component may be a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample. Thus, a "component" can include a polypeptide or other analyte as above, that is immobilized on a solid support, such as by binding to an anti-analyte (e.g., anti-polypeptide) antibody. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

The term "specific binding partner" is a member of a specific binding pair. A specific binding pair comprises two different molecules that specifically bind to each other through chemical or physical means. Therefore, in addition to antigen and antibody specific binding, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

The term "Fc region" defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (e.g., U.S. Pat. Nos. 5,648,260 and 5,624,821). The Fc region mediates several important effector functions, e.g., cytokine induction, antibody dependent cell mediated cytotoxicity (ADCC), phagocytosis, complement dependent cytotoxicity (CDC), and half-life/clearance rate of antibody and antigen-antibody complexes. In some cases these effector functions are desirable for a therapeutic immunoglobulin but in other cases might be unnecessary or even deleterious, depending on the therapeutic objectives.

The term "antigen-binding portion" of a binding protein means one or more fragments of a binding protein (preferrably., an antibody, or a receptor) that retain the ability to specifically bind to an antigen. The antigen-binding portion of a binding protein can be performed by fragments of a full-length antibody, as well as bispecific, dual specific, or multi-specific formats; specifically binding to two or more different antigens. Examples of binding fragments encompassed within the term "antigen-binding portion" of an binding protein include (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which comprises a single variable domain; and (vi) an isolated complementarity determining region (CDR). Furthermore, although the two domains of the Fv fragment, VL and VH, encoded by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed. In addition, single chain antibodies also include "linear antibodies" comprising a pair of tandem Fv segments (VH-CH1-VH-CH1) which, together with complementary light chain polypeptides, form a pair of antigen binding regions.

The term "monovalent binding protein" refers to a binding protein comprising one antigen (ligand) binding site for each antigen. The term "multivalent binding protein" means a binding protein comprising two or more antigen (ligand) binding sites for the same antigen. In an embodiment, the multivalent binding protein is engineered to have three or more antigen binding sites, and is not a naturally occurring antibody. The term "multispecific binding protein" refers to a binding protein capable of binding two or more related or unrelated targets. In an embodiment, a monovalent binding proteins may be multispecific in that it possess one binding domain for each of the different target antigens.

The term "linker" means an amino acid residue or a polypeptide comprising two or more amino acid residues joined by peptide bonds that are used to link two polypeptides (e.g., two VH or two VL domains). Such linker polypeptides are well known in the art (see, e.g., Holliger et al. (1993) Proc. Natl. Acad. Sci. USA 90:6444-6448; Poljak et al. (1994) Structure 2:1121-1123).

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "CDR" means a complementarity determining region within an immunoglobulin variable region sequence. There are three CDRs in each of the variable regions of the heavy chain and the light chain, which are designated CDR1, CDR2 and CDR3, for each of the heavy and light chain variable regions. The term "CDR set" refers to a group of three CDRs that occur in a single variable region capable of binding the antigen. The exact boundaries of these CDRs have been defined differently according to different systems. The system described by Kabat (Kabat et al. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) J. Mol. Biol. 196:901-917; Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The term "epitope" means a region of an antigen that is bound by a binding protein, e.g., a polypeptide and/or other determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In an embodiment, an epitope comprises the amino acid residues of a region of an antigen (or fragment thereof) known to bind to the complementary site on the specific binding partner. An antigenic fragment can contain more than one epitope. In certain embodiments, a binding protein specifically binds an antigen when it recognizes its target antigen in a complex mixture of proteins and/or macromolecules. Binding proteins "bind to the same epitope" if the antibodies cross-compete (one prevents the binding or modulating effect of the other). In addition, structural definitions of epitopes (overlapping, similar, identical) are informative; and functional definitions encompass structural (binding) and functional (modulation, competition) parameters. Different regions of proteins may perform different functions. For example specific regions of a cytokine interact with its cytokine receptor to bring about receptor activation whereas other regions of the protein may be required for stabilizing the cytokine. To abrogate the negative effects of cytokine signaling, the cytokine may be targeted with a binding protein that binds specifically to the receptor interacting region(s), thereby preventing the binding of its receptor. Alternatively, a binding protein may target the regions responsible for cytokine stabilization, thereby designating the protein for degradation. The methods of visualizing and modeling epitope recognition are known to one skilled in the art (US 20090311253).

"Pharmacokinetics" refers to the process by which a drug is absorbed, distributed, metabolized, and excreted by an organism. To generate a multivalent binding protein molecule with a desired pharmacokinetic profile, parent binding proteins with similarly desired pharmacokinetic profiles are selected. The PK profiles of the selected parental binding proteins can be easily determined in rodents using methods known to one skilled in the art (US 20090311253).

"Bioavailability" refers to the amount of active drug that reaches its target following administration. Bioavailability is function of several of the previously described properties, including stability, solubility, immunogenicity and pharmacokinetics, and can be assessed using methods known to one skilled in the art (US 20090311253).

The term "surface plasmon resonance" means an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J.). For further descriptions, see Jönsson et al. (1993) Ann Biol. Clin. 51:19-26. The term "$K_{on}$" means the on rate constant for association of a binding protein (e.g., an antibody or DVD-Ig) to the antigen to form the, e.g., DVD-Ig/antigen complex. The term "$K_{on}$" also means "association rate constant", or "ka", as is used interchangeably herein. This value indicating the binding rate of a binding protein to its target antigen or the rate of complex formation between a binding protein, e.g., an antibody, and antigen also is shown by the equation below:

$$\text{Antibody (``}Ab\text{'')+Antigen (``}Ag\text{'')} \rightarrow Ab\text{-}Ag$$

The term "$K_{off}$" means the off rate constant for dissociation, or "dissociation rate constant", of a binding protein (e.g., an antibody or DVD-Ig) from the, e.g., DVD-Ig/antigen complex as is known in the art. This value indicates the dissociation rate of a binding protein, e.g., an antibody, from its target antigen or separation of Ab-Ag complex over time into free antibody and antigen as shown by the equation below:

$$Ab + Ag \leftarrow Ab\text{-}Ag$$

The terms "$K_d$" and "equilibrium dissociation constant" means the value obtained in a titration measurement at equilibrium, or by dividing the dissociation rate constant ($K_{off}$) by the association rate constant ($K_{on}$). The association rate constant, the dissociation rate constant and the equilibrium dissociation constant, are used to represent the binding affinity of a binding protein (e.g., an antibody or DVD-Ig) to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

The term "variant" means a polypeptide that differs from a given polypeptide in amino acid sequence by the addition (e.g., insertion), deletion, or conservative substitution of amino acids, but that retains the biological activity of the given polypeptide (e.g., a variant IL-17 antibody can compete with anti-IL-17 antibody for binding to IL-17). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes in a protein can be substituted and the protein still retains protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also includes polypeptide or fragment thereof that has been differentially processed, such as by proteolysis, phosphorylation, or other post-translational modification, yet retains its biological activity or antigen reactivity, e.g., the ability to bind to IL-17. The term "variant" encompasses fragments of a variant unless otherwise defined. A variant may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to the wildtype sequence.

The monovalent binding proteins and methods of making the same are provided. The binding protein can be generated using various techniques. Expression vectors, host cells and methods of generating the binding proteins are provided in this disclosure.

The antigen-binding variable domains of the binding proteins of this invention can be obtained from parent binding proteins, including polyclonal Abs, monoclonal Abs, and or receptors capable of binding antigens of interest. These parent binding proteins may be naturally occurring or may be generated by recombinant technology. The person of ordinary skill in the art is well familiar with many methods for producing antibodies and/or isolated receptors, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques. The binding variable domains of the binding proteins can also be obtained from isolated receptor molecules obtained by extraction procedures known in the art (e.g., using solvents, detergents, and/or affinity purifications), or determined by biophysical methods known in the art (e.g., X-ray crystallography, NMR, interferometry, and/or computer modeling).

An embodiment is provided comprising selecting parent binding proteins with at least one or more properties desired in the binding protein molecule. In an embodiment, the desired property is one or more of those used to characterize antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

Monovalent antibodies may be designed such that one of the antigen binding arms is rendered non-functional. The variable domains can be obtained using recombinant DNA techniques from parent binding proteins generated by any one of the methods described herein. In an embodiment, a variable domain is a murine heavy or light chain variable domain. In another embodiment, a variable domain is a CDR grafted or a humanized variable heavy or light chain domain. In an embodiment, a variable domain is a human heavy or light chain variable domain.

The linker sequence may be a single amino acid or a polypeptide sequence. In an embodiment, the choice of linker sequences is based on crystal structure analysis of several Fab molecules. There is a natural flexible linkage between the variable domain and the CH1/CL constant domain in Fab or antibody molecular structure. This natural linkage may contain approximately 10-12 amino acid residues, contributed by 4-6 residues from the C-terminus of a V domain and 4-6 residues from the N-terminus of a CL/CH1 domain. The binding proteins may be generated using N-terminal 5-6 amino acid residues, or 11-12 amino acid residues, of CL or CH1 as a linker in the light chain and heavy chains, respectively. The N-terminal residues of CL or CH1 domains, particularly the first 5-6 amino acid residues, can adopt a loop conformation without strong secondary structures, and therefore can act as flexible linkers between the two variable domains. The N-terminal residues of CL or CH1 domains are natural extension of the variable domains, as they are part of the Ig sequences, and therefore their use may minimize to a large extent any immunogenicity potentially arising from the linkers and junctions.

Other linker sequences may include any sequence of any length of a CL/CH1 domain but not all residues of a CL/CH1 domain; for example the first 5-12 amino acid residues of a CL/CH1 domain; the light chain linkers can be from Cκ or Cλ; and the heavy chain linkers can be derived from CH1 of any isotype, including Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR); G/S based sequences (e.g., G4S repeats (SEQ ID NO: 103)); hinge region-derived sequences; and other natural sequences from other proteins.

In an embodiment, one or more constant domains are linked to the variable domains using recombinant DNA techniques. In an embodiment, a sequence comprising one or more heavy chain variable domains is linked to a heavy chain constant domain and a sequence comprising one or more light chain variable domains is linked to a light chain constant domain. In an embodiment, the constant domains are human heavy chain constant domains and human light chain constant domains, respectively. In an embodiment, the heavy chain is further linked to an Fc region. The Fc region may be a native sequence Fc region or a variant Fc region.

In another embodiment, the Fc region is a human Fc region. In another embodiment, the Fc region includes Fc region from IgG1, IgG2, IgG3, IgG4, IgA, IgM, IgE, or IgD.

Detailed description of specific binding proteins capable of binding specific targets, and methods of making the same, is provided in the Examples section below.

In one embodiment, at least 50%, at least 75% or at least 90% of the assembled, and immunoglobulin molecules expressed in a host cell are the desired monovalent binding proteins, and therefore possess enhanced commercial utility.

Methods of expressing a monovalent binding protein in a single cell leading to a "primary product" of a "monovalent binding protein", where the "primary product" is more than 50%, more than 75% or more than 90%, of all assembled protein are provided.

Given their ability to bind to one or more ligands without the crosslinking effect, the monovalent antibodies provided herein may be used as an antagonist of the target ligand (or antigen).

In an embodiment, the binding proteins provided herein are capable of neutralizing the activity of their antigen targets both in vitro and in vivo. Accordingly, such binding proteins can be used to inhibit antigen activity, e.g., in a cell culture containing the antigens, in human subjects or in other mammalian subjects having the antigens with which a binding protein provided herein cross-reacts. In another embodiment, a method for reducing antigen activity in a subject suffering from a disease or disorder in which the antigen activity is detrimental is provided. A binding protein provided herein can be administered to a human subject for therapeutic purposes.

The term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc., of the subject). Non-limiting examples of disorders that can be treated with the binding proteins provided herein include those disorders discussed below and in the section pertaining to pharmaceutical compositions comprising the binding proteins.

Additionally, the binding proteins provided herein can be employed for tissue-specific delivery (target a tissue marker and a disease mediator for enhanced local PK thus higher efficacy and/or lower toxicity), including intracellular delivery (targeting an internalizing receptor and an intracellular molecule), delivering to inside brain (targeting transferrin receptor and a CNS disease mediator for crossing the blood-brain barrier). The binding proteins can also serve as a carrier protein to deliver an antigen to a specific location via binding to a non-neutralizing epitope of that antigen and also to increase the half-life of the antigen. Furthermore, the binding proteins can be designed to either be physically linked to medical devices implanted into patients or target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397). Directing appropriate types of cell to the site of medical implant may promote healing and restoring normal tissue function. Alternatively, inhibition of mediators (including but not limited to cytokines), released upon device implantation by a receptor antibody fusion protein coupled to or target to a device is also provided.

Binding protein molecules provided herein are useful as therapeutic molecules to treat various diseases, e.g., wherein the targets that are recognized by the binding proteins are detrimental. Such binding proteins may bind one or more targets involved in a specific disease.

Without limiting the disclosure, further information on certain disease conditions is provided.

1. Human Autoimmune and Inflammatory Response

Various cytokines and chemokines have been implicated in general autoimmune and inflammatory responses, including, for example, asthma, allergies, allergic lung disease, allergic rhinitis, atopic dermatitis, chronic obstructive pulmonary disease (COPD), fibrosis, cystic fibrosis (CF), fibrotic lung disease, idiopathic pulmonary fibrosis, liver fibrosis, lupus, hepatitis B-related liver diseases and fibrosis, sepsis, systemic lupus erythematosus (SLE), glomerulonephritis, inflammatory skin diseases, psoriasis, diabetes, insulin dependent diabetes mellitus, inflammatory bowel disease (IBD), ulcerative colitis (UC), Crohn's disease (CD), rheumatoid arthritis (RA), osteoarthritis (OA), multiple sclerosis (MS), graft-versus-host disease (GVHD), transplant rejection, ischemic heart disease (IHD), celiac disease, contact hypersensitivity, alcoholic liver disease, Behcet's disease, atherosclerotic vascular disease, occular surface inflammatory diseases, or Lyme disease.

The binding proteins provided herein can be used to treat neurological disorders. In an embodiment, the binding proteins provided herein or antigen-binding portions thereof, are used to treat neurodegenerative diseases, and conditions involving neuronal regeneration and spinal cord injury.

2. Asthma

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. Corticosteroids are the most important anti-inflammatory treatment for asthma today, however their mechanism of action is non-specific and safety concerns exist, especially in the juvenile patient population. The development of more specific and targeted therapies is therefore warranted.

Various cytokines have been implicated as having a pivotal role in causing pathological responses associated with asthma. The development of mAb against these cotokines as well as rDVD-Ig™ constructs may prove effective in preventing and/or treating asthma.

Animal models such as an OVA-induced asthma mouse model, where both inflammation and AHR can be assessed, are known in the art and may be used to determine the ability of various binding protein molecules to treat asthma Animal models for studying asthma are disclosed in Coffman, et al. (2005) J. Exp. Med. 201(12):1875-1879; Lloyd et al. (2001) Adv. Immunol. 77: 263-295; Boyce et al. (2005) J. Exp. Med. 201(12):1869-1873; and Snibson et al. (2005) J. Brit. Soc. Allergy Clin. Immunol. 35(2):146-52. In addition to routine safety assessments of these target pairs specific tests for the degree of immunosuppression may be warranted and helpful in selecting the best target pairs (see Luster et al.

(1994) Toxicol. 92(1-3):229-43; Descotes et al. (1992) Dev. Biol. Standard. 77:99-102; Hart et al. (2001) J. Allergy Clin. Immunol. 108(2):250-257).

3. Rheumatoid Arthritis

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines, chemokines, and growth factors are expressed in diseased joints. Recent studies indicate that the involvement of T cells in RA is mediated to a significant extent by certain cytokines. Beneficial effects of blocking these cytokines were also observed various animal models of the disease (for a review see Witowski et al. (2004) Cell. Mol. Life. Sci. 61: 567-579). Whether a binding protein molecule will be useful for the treatment of rheumatoid arthritis can be assessed using pre-clinical animal RA models such as the collagen-induced arthritis mouse model. Other useful models are also well known in the art (see Brand (2005) Comp. Med. 55(2):114-22). Based on the cross-reactivity of the parental antibodies for human and mouse orthologues (e.g., reactivity for human and mouse TNF, human and mouse IL-15, etc.) validation studies in the mouse CIA model may be conducted with "matched surrogate antibody" derived binding protein molecules; briefly, a binding protein based on two (or more) mouse target specific antibodies may be matched to the extent possible to the characteristics of the parental human or humanized antibodies used for human binding protein construction (e.g., similar affinity, similar neutralization potency, similar half-life, etc.).

4. Systemic Lupus Erythematosus (SLE)

The immunopathogenic hallmark of SLE is the polyclonal B cell activation, which leads to hyperglobulinemia, autoantibody production and immune complex formation. Significant increased levels of certain cytokines have been detected in patients with systemic lupus erythematosus (Morimoto et al. (2001) Autoimmunity, 34(1):19-25; Wong et al. (2008) Clin Immunol. 127(3):385-93). Increased cytokine production has been shown in patients with SLE as well as in animals with lupus-like diseases. Animal models have demonstrated that blockade of these cytokines may decrease lupus manifestations (for a review see Nalbandian et al. (2009) 157(2): 209-215). Based on the cross-reactivity of the parental antibodies for human and mouse othologues (e.g., reactivity for human and mouse CD20, human and mouse interferon alpha, etc.) validation studies in a mouse lupus model may be conducted with "matched surrogate antibody" derived binding protein molecules. Briefly, a binding protein based two (or more) mouse target specific antibodies may be matched to the extent possible to the characteristics of the parental human or humanized antibodies used for human binding protein construction (e.g., similar affinity, similar neutralization potency, similar half-life, etc.).

5. Multiple Sclerosis

Multiple sclerosis (MS) is a complex human autoimmune-type disease with a predominantly unknown etiology. Immunologic destruction of myelin basic protein (MBP) throughout the nervous system is the major pathology of multiple sclerosis. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification. In MS, increased expression of certain cytokine has been detected both in brain lesions and in mononuclear cells isolated from blood and cerebrospinal fluid. Cells producing these cytokines are highly enriched in active MS lesions, suggesting that neutralization of this cytokine has the potential of being beneficial (for a review see Witowski et al. (2004) Cell. Mol. Life Sci. 61: 567-579).

Several animal models for assessing the usefulness of the binding proteins to treat MS are known in the art (see Steinman et al. (2005) Trends Immunol. 26(11):565-71; Lublin et al. (1985) Springer Semin Immunopathol. 8(3): 197-208; Genain et al. (1997) J. Mol. Med. 75(3):187-97; Tuohy et al. (1999) J. Exp. Med. 189(7):1033-42; Owens et al. (1995) Neurol. Clin. 13(1):51-73; and Hart et al. (2005) J. Immunol. 175(7):4761-8.) Based on the cross-reactivity of the parental antibodies for human and animal species othologues validation studies in the mouse EAE model may be conducted with "matched surrogate antibody" derived binding protein molecules. Briefly, a binding protein based on two (or more) mouse target specific antibodies may be matched to the extent possible to the characteristics of the parental human or humanized antibodies used for human binding protein construction (e.g., similar affinity, similar neutralization potency, similar half-life, etc.). The same concept applies to animal models in other non-rodent species, where a "matched surrogate antibody" derived binding protein would be selected for the anticipated pharmacology and possibly safety studies. In addition to routine safety assessments of these target pairs specific tests for the degree of immunosuppression may be warranted and helpful in selecting the best target pairs (see Luster et al. (1994) Toxicol. 92(1-3): 229-43; Descotes et al. (1992) Devel. Biol. Standard. 77: 99-102; Jones (2000) IDrugs 3(4):442-6).

6. Sepsis

Overwhelming inflammatory and immune responses are essential features of septic shock and play a central part in the pathogenesis of tissue damage, multiple organ failure, and death induced by sepsis. Cytokines have been shown to be mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity. The levels of certain cytokines and clinical prognosis of sepsis have been shown to be negatively correlated. Neutralization of antibody or rDVD-Ig™ constructs against these cytokines may significantly improve the survival rate of patients with sepsis (see Flierl et al. (2008) FASEB J. 22: 2198-2205).

One embodiment pertains to rDVD-Ig™ constructs capable of binding one or more targets involved in sepsis, such as, for example cytokines. The efficacy of such binding proteins for treating sepsis can be assessed in preclinical animal models known in the art (see Buras et al. (2005) Nat. Rev. Drug Discov. 4(10):854-65 and Calandra et al. (2000) Nat. Med. 6(2):164-70).

7. Neurological Disorders a. Neurodegenerative Diseases

Neurodegenerative diseases are either chronic in which case they are usually age-dependent or acute (e.g., stroke, traumatic brain injury, spinal cord injury, etc.). They are characterized by progressive loss of neuronal functions (e.g., neuronal cell death, axon loss, neuritic dystrophy, demyelination), loss of mobility and loss of memory. These chronic neurodegenerative diseases represent a complex interaction between multiple cell types and mediators. Treatment strategies for such diseases are limited and mostly constitute either blocking inflammatory processes with non-specific anti-inflammatory agents (e.g., corticosteroids, COX inhibitors) or agents to prevent neuron loss and/or synaptic functions. These treatments fail to stop disease progression. Specific therapies targeting more than one disease mediator may provide even better therapeutic efficacy for chronic neurodegenerative diseases than observed with targeting a single disease mechanism (see Deane et al. (2003) Nature Med. 9:907-13; and Masliah et al. (2005) Neuron. 46:857).

The binding protein molecules provided herein can bind one or more targets involved in chronic neurodegenerative diseases such as Alzheimers. The efficacy of binding protein molecules can be validated in pre-clinical animal models such as the transgenic mice that over-express amyloid precursor protein or RAGE and develop Alzheimer's disease-like symptoms. In addition, binding protein molecules can be constructed and tested for efficacy in the animal models and the best therapeutic binding protein can be selected for testing in human patients. Binding protein molecules can also be employed for treatment of other neurodegenerative diseases such as Parkinson's disease.

b. Neuronal Regeneration and Spinal Cord Injury

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g., cytokines and chemokines) that worsen the initial injury and result in significant enlargement of the lesion area, sometimes more than 10-fold. Certain cytokine is a mediator of secondary degeneration, which contributes to neuroinflammation and hinders functional recovery.

The efficacy of binding protein molecules can be validated in pre-clinical animal models of spinal cord injury. In addition, these binding protein molecules can be constructed and tested for efficacy in the animal models and the best therapeutic binding protein can be selected for testing in human patients. In general, antibodies do not cross the blood brain barrier (BBB) in an efficient and relevant manner. However, in certain neurologic diseases, e.g., stroke, traumatic brain injury, multiple sclerosis, etc., the BBB may be compromised and allows for increased penetration of binding proteins and antibodies into the brain. In other neurological conditions, where BBB leakage is not occurring, one may employ the targeting of endogenous transport systems, including carrier-mediated transporters such as glucose and amino acid carriers and receptor-mediated transcytosis-mediating cell structures/receptors at the vascular endothelium of the BBB, thus enabling trans-BBB transport of the binding protein. Structures at the BBB enabling such transport include but are not limited to the insulin receptor, transferrin receptor, LRP and RAGE. In addition, strategies enable the use of binding proteins also as shuttles to transport potential drugs into the CNS including low molecular weight drugs, nanoparticles and nucleic acids (Coloma et al. (2000) Pharm Res. 17(3):266-74; Boado et al. (2007) Bioconjug. Chem. 18(2):447-55).

8. Oncological Disorders

Monoclonal antibody therapy has emerged as an important therapeutic modality for cancer (von Mehren et al. (2003) Annu. Rev. Med. 54:343-69). Certain cytokines have been suggested to support tumor growth, probably by stimulating angiogenesis or by modulating anti-tumor immunity and tumor growth. Studies indicate that some cytokines may be central to the novel immunoregulatory pathway in which NKT cells suppress tumor immunosurveillance. (For a review see Kolls et al. (2003) Am. J. Respir. Cell Mol. Biol. 28: 9-11, and Terabe et al. (2004) Cancer Immunol Immunother. 53(2):79-85.)

In an embodiment, diseases that can be treated or diagnosed with the compositions and methods provided herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

In an embodiment, the antibodies provided herein or antigen-binding portions thereof, are used to treat cancer or in the prevention of metastases from the tumors described herein either when used alone or in combination with radiotherapy and/or other chemotherapeutic agents.

9. Gene Therapy

In a specific embodiment, nucleic acid sequences encoding a binding protein provided herein or another prophylactic or therapeutic agent provided herein are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acids produce their encoded antibody or prophylactic or therapeutic agent provided herein that mediates a prophylactic or therapeutic effect.

Any of the methods for gene therapy available in the art can be used in the methods provided herein. For general reviews of the methods of gene therapy, see Goldspiel et al. (1993) Clin. Pharmacy 12:488-505; Wu and Wu (1991) Biotherapy 3:87-95; Tolstoshev (1993) Ann Rev. Pharmacol. Toxicol. 32:573-596; Mulligan (1993) Science 260:926-932; Morgan and Anderson (1993) Ann Rev. Biochem. 62:191-217; and May (1993) TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US Patent Publication No. US20050042664.

II. Pharmaceutical Compositions

Pharmaceutical compositions comprising one or more binding proteins, either alone or in combination with prophylactic agents, therapeutic agents, and/or pharmaceutically acceptable carriers are provided. The pharmaceutical compositions comprising binding proteins provided herein are for use in, but not limited to, diagnosing, detecting, or monitoring a disorder, in preventing, treating, managing, or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

Methods of administering a prophylactic or therapeutic agent provided herein include, but are not limited to, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms provided herein are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding protein provided herein is 0.1-20 mg/kg, for example, 1-10 mg/kg. It is to be noted that dosage values may vary with the type and severity of the condition to be alleviated. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

III. Combination Therapy

A binding protein provided herein also can also be administered with one or more additional therapeutic agents useful in the treatment of various diseases, the additional agent being selected by the skilled artisan for its intended purpose. For example, the additional agent can be a therapeutic agent art-recognized as being useful to treat the disease or condition being treated by the antibody provided herein. The combination can also include more than one additional agent, e.g., two or three additional agents.

Combination therapy agents include, but are not limited to, antineoplastic agents, radiotherapy, chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), COX-2 inhibitors (e.g., celecoxib), kinase inhibitors, and siRNAs.

Combinations to treat autoimmune and inflammatory diseases are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the binding proteins provided herein. Non-limiting examples of therapeutic agents for rheumatoid arthritis with which an antibody provided herein, or antibody binding portion thereof, can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Binding proteins provided herein, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Combinations of therapeutic agents may interfere at different points in the autoimmune and subsequent inflammatory cascade. Examples include a binding protein disclosed herein and a TNF antagonist like a chimeric, humanized or human TNF antibody, Adalimumab, (PCT Publication No. WO 97/29131), CA2 (Remicade™) CDP 571, a soluble p55 or p75 TNF receptor, or derivative thereof (p75TNFR1gG (Enbrel™) or p55TNFR1gG (Lenercept)), a TNFα converting enzyme (TACE) inhibitor; or an IL-1 inhibitor (an Interleukin-1-converting enzyme inhibitor, IL-IRA, etc.). Other combinations include a binding protein disclosed herein and Interleukin 11. Yet another combination include key players of the autoimmune response which may act parallel to, dependent on or in concert with IL-12 function; especially relevant are IL-18 antagonists including an IL-18 antibody, a soluble IL-18 receptor, or an IL-18 binding protein. It has been shown that IL-12 and IL-18 have overlapping but distinct functions and a combination of antagonists to both may be most effective. Yet another combination is a binding protein disclosed herein and a non-depleting anti-CD4 inhibitor. Yet other combinations include a binding protein disclosed herein and an antagonist of the co-stimulatory pathway CD80 (B7.1) or CD86 (B7.2) including an antibody, a soluble receptor, or an antagonistic ligand.

The binding proteins provided herein may also be combined with an agent, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, a corticosteroid (oral, inhaled and local injection), a beta-2 adrenoreceptor agonist (salbutamol, terbutaline, salmeteral), a xanthine (theophylline, aminophylline), cromoglycate, nedocromil, ketotifen, ipratropium, oxitropium, cyclosporin, FK506, rapamycin, mycophenolate mofetil, leflunomide, an NSAID, for example, ibuprofen, a corticosteroid such as prednisolone, a phosphodiesterase inhibitor, an adensosine agonist, an antithrombotic agent, a complement inhibitor, an adrenergic agent, an agent which interferes with signalling by proinflammatory cytokines such as TNF-α or IL-1 (e.g., IRAK, NIK, IKK, p38 or a MAP kinase inhibitor), an IL-1β converting enzyme inhibitor, a TNFα converting enzyme (TACE) inhibitor, a T-cell signaling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivative thereof (e.g., a soluble p55 or p75 TNF receptor or the derivative p75TNFRIgG (Enbrel™) or p55TNFRIgG (Lenercept), sIL-1RI, sIL-1RII, sIL-6R), an antiinflammatory cytokine (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, or Mesopram. Combinations include methotrexate or leflunomide and in moderate or severe rheumatoid arthritis cases, cyclosporine.

In one embodiment, the binding protein or antigen-binding portion thereof, is administered in combination with one of the following agents for the treatment of rheumatoid arthritis: a small molecule inhibitor of KDR, a small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; or mesopram.

Non-limiting examples of therapeutic agents for inflammatory bowel disease with which a binding protein provided herein can be combined include the following: budenoside; epidermal growth factor; a corticosteroid; cyclosporin, sulfasalazine; aminosalicylates; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1β mAb; an anti-IL-6 mAb; a growth factor; an elastase inhibitor; a pyridinyl-imidazole compound; an antibody to or antagonist of other human cytokines or growth factors, for example, TNF, LT, IL-1, IL-2, IL-6, IL-7, IL-8, IL-15, IL-16, IL-17, IL-18, EMAP-II, GM-CSF, FGF, or PDGF. Antibodies provided herein, or antigen binding portions thereof, can be combined with an antibody to a cell surface molecule such as CD2, CD3, CD4, CD8, CD25, CD28, CD30, CD40, CD45, CD69, CD90 or their ligands. The antibodies provided herein, or antigen binding portions thereof, may also be combined with an agent, such as methotrexate, cyclosporin, FK506, rapamycin, mycophenolate mofetil, leflunomide, an NSAID, for example, ibuprofen, a corticosteroid such as prednisolone, a phosphodiesterase inhibitor, an adenosine agonist, an antithrombotic agent, a complement inhibitor, an adrenergic agent, an agent which interferes with signalling by proinflammatory cytokines such as TNFα or IL-1 (e.g., an IRAK, NIK, IKK, p38 or MAP kinase inhibitor), an IL-1β converting enzyme inhibitor, a TNFα converting enzyme inhibitor, a T-cell signalling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivative thereof (e.g., a soluble p55 or p75 TNF receptor, sIL-1RI, sIL-1RII, sIL-6R) or an antiinflammatory cytokine (e.g., IL-4, IL-10, IL-11, IL-13 or TGFβ) or a bcl-2 inhibitor.

Examples of therapeutic agents for Crohn's disease in which a binding protein can be combined include the following: a TNF antagonist, for example, an anti-TNF antibody, Adalimumab (PCT Publication No. WO 97/29131; HUMIRA), CA2 (REMICADE), CDP 571, a TNFR-Ig construct, (p75TNFRIgG (ENBREL) or a p55TNFRIgG (LENERCEPT)) inhibitor or a PDE4 inhibitor. Antibodies provided herein, or antigen binding portions thereof, can be combined with a corticosteroid, for example, budenoside and dexamethasone. Binding proteins provided herein or antigen binding portions thereof, may also be combined with an agent such as sulfasalazine, 5-aminosalicylic acid and olsalazine, or an agent that interferes with the synthesis or action of a proinflammatory cytokine such as IL-1, for example, an IL-1β converting enzyme inhibitor or IL-1ra. Antibodies provided herein or antigen binding portion thereof may also be used with a T cell signaling inhibitor, for example, a tyrosine kinase inhibitor or an 6-mercaptopurine. Binding proteins provided herein, or antigen binding portions thereof, can be combined with IL-11. Binding proteins provided herein, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab or interferon-gamma Non-limiting examples of therapeutic agents for multiple sclerosis with which binding proteins provided herein can be combined include the following: a corticosteroid; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; an antibody to or antagonist of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, or PDGF. Binding proteins provided herein can be combined with an antibody to a cell surface molecule such as CD2, CD3, CD4, CD8, CD19, CD20, CD25, CD28, CD30, CD40, CD45, CD69, CD80, CD86, CD90 or their ligands. Binding proteins provided herein, may also be combined with an agent, such as methotrexate, cyclosporine, FK506, rapamycin, mycophenolate mofetil, leflunomide, an NSAID, for example, ibuprofen, a corticosteroid such as prednisolone, a phosphodiesterase inhibitor, an adenosine agonist, an antithrombotic agent, a complement inhibitor, an adrenergic agent, an agent which interferes with signalling by a proinflammatory cytokine such as TNFα or IL-1 (e.g., IRAK, NIK, IKK, p38 or a MAP kinase inhibitor), an IL-1β converting enzyme inhibitor, a TACE inhibitor, a T-cell signaling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivatives thereof (e.g., a soluble p55 or p75 TNF receptor, sIL-1RI, sIL-1RII, sIL-6R), an antiinflammatory cytokine (e.g., IL-4, IL-10, IL-13 or TGFβ) or a bcl-2 inhibitor.

Examples of therapeutic agents for multiple sclerosis in which binding proteins provided herein can be combined include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

Non-limiting examples of therapeutic agents for asthma with which binding proteins provided herein can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which binding proteins provided herein can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for psoriasis with which binding proteins provided herein can be combined include the following: small molecule inhibitor of KDR, small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Examples of therapeutic agents for SLE (Lupus) in which binding proteins provided herein can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. Binding proteins provided herein may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Binding proteins provided herein may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Binding proteins provided herein, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies provided herein or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, Adalimumab (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) and bcl-2 inhibitors, because bcl-2 overexpression in transgenic mice has been demonstrated to cause a lupus like phenotype (see Marquina The pharmaceutical compositions provided herein may include a "therapeutically effective amount" or a "prophylactically effective amount" of a binding protein provided herein. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the antibody, or antibody binding portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

IV. Diagnostics

The disclosure herein also provides diagnostic applications including, but not limited to, diagnostic assay methods, diagnostic kits containing one or more binding proteins, and adaptation of the methods and kits for use in automated and/or semi-automated systems. The methods, kits, and adaptations provided may be employed in the detection, monitoring, and/or treatment of a disease or disorder in an individual. This is further elucidated below.

A. Method of Assay

The present disclosure also provides a method for determining the presence, amount or concentration of an analyte, or fragment thereof, in a test sample using at least one binding protein as described herein. Any suitable assay as is known in the art can be used in the method. Examples include, but are not limited to, immunoassays and/or methods employing mass spectrometry.

Immunoassays provided by the present disclosure may include sandwich immunoassays, radioimmunoassay (RIA), enzyme immunoassay (EIA), enzyme-linked immunosorbent assay (ELISA), competitive-inhibition immunoassays, fluorescence polarization immunoassay (FPIA), enzyme multiplied immunoassay technique (EMIT), bioluminescence resonance energy transfer (BRET), and homogenous chemiluminescent assays, among others.

A chemiluminescent microparticle immunoassay, in particular one employing the ARCHITECT® automated analyzer (Abbott Laboratories, Abbott Park, Ill.), is an example of an immunoassay.

Methods employing mass spectrometry are provided by the present disclosure and include, but are not limited to MALDI (matrix-assisted laser desorption/ionization) or by SELDI (surface-enhanced laser desorption/ionization).

Methods for collecting, handling, processing, and analyzing biological test samples using immunoassays and mass spectrometry would be well-known to one skilled in the art, are provided for in the practice of the present disclosure (US 2009-0311253 A1).

B. Kit

A kit for assaying a test sample for the presence, amount or concentration of an analyte, or fragment thereof, in a test sample is also provided. The kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or an anti-analyte binding protein (or a fragment, a variant, or a fragment of a variant thereof), which is optionally immobilized on a solid phase.

Optionally, the kit may comprise a calibrator or control, which may comprise isolated or purified analyte. The kit can comprise at least one component for assaying the test sample for an analyte by immunoassay and/or mass spectrometry.

The kit components, including the analyte, binding protein, and/or anti-analyte binding protein, or fragments thereof, may be optionally labeled using any art-known detectable label. The materials and methods for the creation provided for in the practice of the present disclosure would be known to one skilled in the art (US 2009-0311253 A1).

C. Adaptation of Kit and Method

The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, for example, in U.S. Pat. Nos. 5,089,424 and 5,006,309, and as commercially marketed, for example, by Abbott Laboratories (Abbott Park, Ill.) as ARCHITECT®.

Other platforms available from Abbott Laboratories include, but are not limited to, AxSYM®, IMx® (see, for example, U.S. Pat. No. 5,294,404, PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1: Anti-cMet MBody Molecules

The hepatocyte growth factor (HGF)/cMet pathway has been linked to the cancer progression by driving proliferation, motility, invasion, and angiogenesis (see Nakamura et al. (1989) Nature 342: 440-3; Lokker et al. (1992) EMBO J. 11: 2503-10; Naka et al. (1992) J. Biol. Chem. 267: 20114-9; and Peruzzi et al. (2006) Clin. Cancer Res. 12:3657-60, each incorporated herein by reference). Targeting this pathway may suppress cancer growth and metastasis. However, regular cMet antibodies are intrinsically agonistic, which may be because these antibodies facilitate cMet dimerization on the cell surface (See Prat et al. (1998) J. Cell Science 111: 237-247; and Ohashi et al. (2000) Nature Med. 6: 327-331, each incorporated herein by reference).

Example 1.1: Generation of Heavy Chain (HC) and Light Chain (LC) Constructs for Anti-cMet Ig Mouse hybridoma HB-11895 (5D5.11.6) was purchased from American Type Culture Collection (ATCC, Manassas, Va.). The $V_H$ and $V_L$ cDNA sequences were cloned using methods that were known in the art. The cDNA sequences and translated amino acid sequences are shown in Table 1 and Table 2.

TABLE 1

Anti-cMet Variable Domain cDNA Sequences

| Domain | Sequence Identifier | Cloned cDNA Sequences |
|---|---|---|
| Anti-cMet $V_H$ | SEQ ID NO: 1 | CAGGTCCAACTGCAGCAGTCTGGGCCTGAGCTGGTGA GGCCTGGGGCTTCAGTGAAGATGTCCTGCAGGGCTTC GGGCTATACCTTCACCAGCTACTGGTTGCACTGGGTT AAACAGAGGCCTGGACAAGGCCTTGAGTGGATTGGCA TGATTGATCCTTCCAATAGTGACACTAGGTTTAATCC GAACTTCAAGGACAAGGCCACATTGAATGTAGACAGA TCTTCCAACACAGCCTACATGCTGCTCAGCAGCCTGA CATCTGCTGACTCTGCAGTCTATTACTGTGCCACATA TGGTAGCTACGTTTCCCCTCTGGACTACTGGGGTCAA GGAACCCTCAGTCACCGTCTCCTCA |
| Anti-cMet $V_L$ | SEQ ID NO: 2 | GACTTTATGATGTCACAGTCTCCATCCTCCCTAACTG TGTCAGTTGGAGAGAAGGTTACTGTGAGCTGCAAGTC CAGTCAGTCCCTTTTATATACTAGCAGTCAGAAGAAC TACTTGGCCTGGTACCAGCAGAAACCAGGTCAGTCTC CTAAACTGCTGATTTACTGGGCATCCACTAGGGAATC TGGGGTCCCTGATCGCTTCACAGGCAGTGGATCTGGG ACAGATTTCACTCTCACCATCACCAGTGTGAAGGCTG ACGACCTGGCAGTTTATTACTGTCAGCAATATTATGC CTATCCGTGGACGTTCGGTGGAGGCACCAAGTTGGAG CTCAAACGG |

TABLE 2

Anti-cMet Variable Domain Amino Acid Sequences

| Protein Region | Sequence Identifier | Amino acid sequence |
|---|---|---|
| Anti-cMet $V_H$ | SEQ ID NO: 3 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATYGSYVSPLDYWGQ GTSVTVSS |
| Anti-cMet $V_L$ | SEQ ID NO: 4 | DFMMSQSPSSLTVSVGEKVTVSCKSSQSLLYTSSQKN YLAWYQQKPGQSPKLLIYWASTRESGVPDRFTGSGSG TDFTLTITSVKADDLAVYYCQQYYAYPWTFGGGTKLE LKR |

The light chain and heavy chain cDNA sequences were PCR amplified with platinum PCR SuperMix High Fidelity (Invitrogen, Carlsbad, Calif.). The PCR products were cloned into pHybE-hCk and pHybE-hCg1, z, non-a vectors (Abbott Laboratories), respectively. After preparation, the plasmid sequences were confirmed by the dideoxy chain termination method using an ABI 3730XL Genetic Analyzer (Applied Biosystesm, Foster City, Calif.). The full length light chain and heavy chain sequences are shown in Table 3.

TABLE 3

Full Length Anti-cMet HC And LC Sequences.

| Protein Region | Sequence Identifier | Amino Acid Sequence |
|---|---|---|
| Anti-cMet HC | SEQ ID NO: 5 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATYGSYVSPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |

TABLE 3-continued

Full Length Anti-cMet HC And LC Sequences.

| Protein Region | Sequence Identifier | Amino Acid Sequence 12345678901234567890 |
|---|---|---|
| Anti-cMet LC | SEQ ID NO: 6 | DFMMSQSPSSLTVSVGEKVTVSCKSSQSLLYTSSQKNYL AWYQQKPGQSPKLLIYWASTRESGVPDRFTGSGSGTDFT LTITSVKADDLAVYYCQQYYAYPWTFGGGTKLELKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |

Example 1.2: Introducing Mutation Combinations to Variable Domain to Abolish Anti-cMet Antibody/antigen Binding To abolish cMet antibody/antigen binding, alanine-scanning method was used to introduce mutations to HC CDR3 region. Site-directed mutagenesis was used to introduce mutation combination to each specific position using methods well known in the art. The amino acid sequences of six HC mutants are shown in Table 4.

TABLE 4

Full Length Anti-cMet HC and LC Sequences

| Protein Region | Sequence Identifier | Amino Acid Sequence 12345678901234567890 |
|---|---|---|
| Anti-cMet-AA1 HC | SEQ ID NO: 7 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCAAYGSYVSPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| Anti-cMet-AA2 HC | SEQ ID NO: 8 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATAASYVSPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| Anti-cMet-AA3 HC | SEQ ID NO: 9 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATYGAAVSPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| Anti-cMet-AA4 HC | SEQ ID NO: 10 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATYGSYAAPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP |

TABLE 4-continued

Full Length Anti-cMet HC and LC Sequences

| Protein Region | Sequence Identifier | Amino Acid Sequence 12345678901234567890 |
|---|---|---|
| | | EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| Anti-cMet-AA5 HC | SEQ ID NO: 11 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATYGSYVSPLDYWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| Anti-cMet-AA6 HC | SEQ ID NO: 12 | QVQLQQSGPELVRPGASVKMSCRASGYTFTSYWLHWVKQ RPGQGLEWIGMIDPSNSDTRFNPNFKDKATLNVDRSSNT AYMLLSSLTSADSAVYYCATYGSYVSPLAAWGQGTSVTV SSASTKGPSVFPLAPSSKSTSGGTAALGCLVKDYFPEPV TVSWNSGALTSGVHTFPAVLQSSGLYSLSSVVTVPSSSL GTQTYICNVNHEPSNTKVDEKVEPESCDETHTCPPCPAP ELLGGPSVFLFPPEPEDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |

Example 1.3: Characterization of Antigen-binding Capability of Anti-cMet Antibodies with $V_H$ Mutations by ELISA Each cMet HC plasmids with $V_H$ mutations was paired with the common cMet LC plasmid for transfection of human embryonic kidney 293-6E cells (American Type Culture Collection, Manassas, Va.) with polyethylenimine (Sigma, St. Louis, Mo.). The cell culture media was harvested six to seven days-post transfection and the antibodies were purified using protein G chromatography (Invitrogen, Carlsbad, Calif.) according to the manufacturer's instructions.

cMet binding ELISA was performed to characterize the antigen binding property of cMet antibodies. 96-well ELISA plates were coated with 100 μl/well 5 μg/ml anti-mouse IgG Fc in PBS at 4° C. overnight. After 3 washes with PBS/0.05% Tween®20, the plates were blocked with 5% milk in PBS for 1 hour at room temperature. After another 3 washes with PBS/0.05% Tween®20, 100 μl cMet antibody was added to each well followed by an incubation of 1 hour at room temperature. Binding biotin-labeled cMet was detected by Streptavidin-horseradish peroxidase (KPL, Gaithersburg, Md.) and tetramethylbenzidine (Thermo Scientific, Rockford, Ill.). Final absorbances were acquired at 450 nm after stopping the reactions with 2 mol/L $H_2SO_4$. The data showed that cMet antibodies with AA2, AA3 and AA6 VH mutations almost completely lost their capability to bind cMet antigen (See Table 5 and FIG. 1). The $EC_{50}$ of CMet AA6 Ig is not listed in Table 5, but judging from FIG. 1, the $EC_{50}$ for CMet AA6 Ig should be similar to those obtained for AA2 and AA3. The terms $EC_{50}$ and $IC_{50}$ may be used interchangeably in this Example to reflect the concentration of the antibody which induces a response halfway between the baseline and the maximum after a specified exposure time.

TABLE 5

ELISA Binding Analysis of cMet Antibodies With $V_H$ Mutations

| Antibody | $EC_{50}$ (nM) |
|---|---|
| cMet Ig | 0.30 |
| cMet AA1 Ig | 7.25 |
| cMet AA2 Ig | 252.8 |
| cMet AA3 Ig | 104.8 |
| cMet AA4 Ig | 1.24 |
| cMet AA5 Ig | 1.81 |
| cMet AA6 Ig | N/A |

Example 1.4: Molecular Cloning of Anti-cMet MBody Molecules

MBody technology aims to inactivate or remove one binding arm of an antibody or antibody-like molecule. In one aspect, instead of binding target antigen(s) bivalently, an MBody binds to antigen monovalently. This concept applies to all immunoglobulin-like molecules which normally have 2 binding arms that are involved in antigen binding. Such molecules include, but are not limit to, immunoglobulins, dual variable domain immunoglobulin (DVD-Ig™), proteins, triple variable domain immunoglobulin (TVD-Ig™) proteins, and receptor antibodies (RAB), (Fab)2.

An MBody molecule contains only one functional antigen binding arm. As demonstrated herein, with this feature, an anti-cMet MBody molecule may function as an antagonist because its monovalent binding to cMet does not induce cMet dimerization and downstream signaling.

To generate cMet Mbodies, knobs-into-holes mutations (Atwell et al. J. Mol. Biol. 1997, 270: 26-35) were introduced into HC construct cMetAA2 HC, cMetAA3 HC and cMetAA6 HC to achieve heterodimerization of HCs. In total, 6 HCs were generated, see Table 6.

TABLE 6

Full Length cMet HC Sequences with VH and Knobs-into-holes Mutations

| Protein Region | Sequence Identifier | Amino Acid Sequence 12345678901234567890 |
|---|---|---|
| Anti-cMet-AA2-Knob HC | SEQ ID NO: 13 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATAASYVSPLDYWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLWCL VKGFYPSDIAVEWESNGQPENNYKTTPPVLDSDGSFF LYSKLTVDKSRWQQGNVFSCSVMHEALHNHYTQKSLS LSPGK |
| Anti-cMet-AA2-Hole HC | SEQ ID NO: 14 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATAASYVSPLDYWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLSCA VKGFYPSDIAVEWESNGQPENNYKTTPPVLDSDGSFF LVSKLTVDKSRWQQGNVFSCSVMHEALHNHYTQKSLS LSPGK |
| Anti-cMet-AA3-knob HC | SEQ ID NO: 15 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATYGAAVSPLDYWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLWCL VKGFYPSDIAVEWESNGQPENNYKTTPPVLDSDGSFF LYSKLTVDKSRWQQGNVFSCSVMHEALHNHYTQKSLS LSPGK |
| Anti-cMet-AA3-hole HC | SEQ ID NO: 16 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATYGAAVSPLDYWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLSCA VKGFYPSDIAVEWESNGQPENNYKTTPPVLDSDGSFF LVSKLTVDKSRWQQGNVFSCSVMHEALHNHYTQKSLS LSPGK |
| Anti-cMet-AA6-knob HC | SEQ ID NO: 17 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATYGSYVSPLAAWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP |

TABLE 6-continued

Full Length cMet HC Sequences with VH and Knobs-into-holes Mutations

| Protein Region | Sequence Identifier | Amino Acid Sequence 12345678901234567890 |
|---|---|---|
| | | EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLWCL VKGFYPSDIAVEWESNGQPENNYKTTPPVLDSDGSFF LYSKLTVDKSRWQQGNVFSCSVMHEALHNHYTQKSLS LSPGK |
| Anti-cMet-AA6-hole HC | SEQ ID NO: 18 | QVQLQQSGPELVRPGASVKMSCRASGYTFTSYWLHWV KQRPGQGLEWIGMIDPSNSDTRFNPNFKDKATLNVDR SSNTAYMLLSSLTSADSAVYYCATYGSYVSPLAAWGQ GTSVTVSSASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLSCA VKGFYPSDIAVEWESNGQPENNYKTTPPVLDSDGSFF LVSKLTVDKSRWQQGNVFSCSVMHEALHNHYTQKSLS LSPGK |

Example 1.5: Transient Expression of Anti-cMet MBody Molecules in 293 Cells

Each cMet HC plasmids with $V_H$ mutations and knob/hole mutations was paired with proper cMet HC plasmid with hole/knob mutation and the common cMet LC plasmid for transfection of human embryonic kidney 293-6E cells (American Type Culture Collection, Manassas, Va.) with polyethylenimine (Sigma, St. Louis, Mo.). See Table 7 for plasmid combination information. The cell culture media was harvested six to seven days-post transfection and the antibodies were purified using protein G chromatography (Invitrogen, Carlsbad, Calif.) according to the manufacturer's instructions. Most cMet MBodies were expressed well in 293 cells (See Table 8) as compared to the expression level of regular antibodies, indicating that these antibodies can be expressed efficiently in mammalian cells. Expression of two MBodies was in single-digit range, which might be due to the sub-optimal expression conditions.

TABLE 7

Plasmid Combination for Transient Transfection of HEK293 Cells to Express cMet MBodies

| MBody | HC plasmid 1 | HC plasmid 2 | LC plasmid |
|---|---|---|---|
| cMet AA2 KH MBody | cMet-AA2-knob HC | cMet-hole HC | cMet LC |
| cMet AA2 HK MBody | cMet-AA2-hole HC | cMet-knob HC | cMet LC |
| cMet AA3 KH MBody | cMet-AA2-knob HC | cMet-hole HC | cMet LC |
| cMet AA3 HK MBody | cMet-AA2-hole HC | cMet-knob HC | cMet LC |
| cMet AA6 KH MBody | cMet-AA2-knob HC | cMet-hole HC | cMet LC |
| cMet AA6 HK MBody | cMet-AA2-hole HC | cMet-knob HC | cMet LC |

TABLE 8

Expression of cMet MBodies in 293 Cells

| MBody | Expression Level (µg/ml) |
|---|---|
| cMet AA2 KH MBody | 4.6 |
| cMet AA2 HK MBody | 81.7 |
| cMet AA3 KH MBody | 62.0 |
| cMet AA3 HK MBody | 69.6 |
| cMet AA6 KH MBody | 76.8 |
| cMet AA6 HK MBody | 4.9 |

Example 1.6: Characterization of cMet MBody Molecules with SDS-PAGE and Size Exclusion Chromatography (SEC)

The cMet MBodies were analyzed by SDS-PAGE under both non-reducing and reducing conditions. Under non-reducing conditions, each of the protein samples showed a single band at 150 kDa. Under reducing conditions, each of the protein samples yielded two bands, one corresponding to heavy chain and the other to light chain. The SDS-PAGE demonstrated that each MBody molecule is produced as a single species, and the heavy and light chains are efficiently paired to form an antibody-like molecule.

SEC analysis was performed to confirm the size of MBody molecules listed above. For the analysis, purified parental cMet MBodies, in phosphate buffered saline (PBS), were applied to a Superdex 200, 300×10 mm column (GE Healthcare, Piscataway, N.J.). An HPLC instrument, Model 10A (Shimadzu, Columbia, Md.) was used for SEC. All proteins were detected using UV light at 280 nm and 214 nm. The elution was isocratic at a flow rate of 0.5 mL/min The SEC data demonstrated that, with VH and knobs-into-holes mutations, cMet MBody molecules are generally stable as monomers (see Table 9). If necessary, purification can be applied to separate MBody aggregates from monomer. The purified monomer is stable under proper storage condition.

TABLE 9

Half-Ig Percent as Determined by SEC

| Construct | Monomer % |
|---|---|
| cMet mAb | 100 |
| cMet mAb-KH | 100 |
| cMet AA2 KH MBody | 73.8 |
| cMet AA2 HK MBody | 98.9 |
| cMet AA3 KH MBody | 94.1 |
| cMet AA3 HK MBody | 98.5 |
| cMet AA6 KH MBody | 96.3 |
| cMet AA6 HK MBody | 99.6 |

Example 1.7: Mass Spectrometry Analysis of cMet MBody Molecules

To measure the intact molecular weight of cMet MBody molecules, 2 μL of MBody (0.8 μg/μL) was injected onto a Poroshell 300 SB-C3 column (1.0×75 mm, 5 μm, Agilent Technologies Inc., Pala Alto, Calif.). The LC/MS analysis was performed on an Agilent HP1200 Capillary HPLC connected to a mass spectrometer Agilent 6224 TOF LC/MS system (Agilent Technologies Inc., Pala Alto, Calif.). Buffer A was 0.1% formic acid in water, and buffer B was 0.1% formic acid in acetonitrile. The flow rate was 50 μL/min. The separation gradient was held at 5% B for the first 5 minutes, increased to 95% B in 0.5 minute and was held at 95% B for the next 9.5 minutes before changed to 5% B in 0.5 minute and was held at 5% B for another 4.5 minutes. The mass spectrometer was operated at 5 k volts spray voltage and scan range was from 600 to 3200 mass to charge ratio.

To measure the molecular weight (MW) of light and heavy chains of a protein sample, 10 μl of protein sample (0.8 μg/μl) was reduced by 0.2 μL 1 M DTT solution at 37° C. for 30 minutes. A Poroshell 300SB-C3 column, 1.0×75 mm, 5 μm (Agilent Technologies Inc., Pala Alto, Calif.) was used to separate the light chain and heavy chain. The LC/MS analysis was performed on an Agilent HP1200 Capillary HPLC connected to a mass spectrometer Agilent 6224 TOF LC/MS system (Agilent Technologies Inc., Pala Alto, Calif.). Buffer A was 0.1% formic acid in water, and buffer B was 0.1% formic acid in acetonitrile. The flow rate was 50 μl/min, and the sample injection volume was 2 μL. The column temperature was set at 60° C. The separation gradient started at 5% B. Increased to 35% in 5 minutes, then increased to 65% B in 15 minutes, increased to 95% B in 1 minute and held at 95% for 4 minutes, and decreased to 5% B in 1 minute and held at 5% B for 5 minutes. The mass spectrometer was operated at 5 k volts spray voltage and scan range was from 600 to 3200 mass to charge ratio.

As shown in Table 10, the experimentally determined molecular mass of cMet MBody molecules, including the light chain, heavy chain, and the full-length protein, is in good agreement with the predicted value.

TABLE 10

Molecular Mass of cMet MBodies by Mass Spectrometry

| | | Molecular mass (Dalton) |
|---|---|---|
| cMet mAb | Light Chain | 24,284.34 (24,284) |
| | Heavy Chain | 50,576.80 (50,576) |
| | Full length | 149,715.66 (149,720) |

TABLE 10-continued

Molecular Mass of cMet MBodies by Mass Spectrometry

| | | Molecular mass (Dalton) |
|---|---|---|
| cMet AA2 HK MBody | Light Chain | 24,284.37 (24,284) |
| | Heavy Chains | 50,378.71 (50,378) and |
| | | 50,661.83 (50,662) |
| | Full length | 149,602.85 (149,602) |
| cMet AA3 KH MBody | Light Chain | 24,284.32 (24,284) |
| | Heavy Chains | 50,554.32 (50,554) and |
| | | 50,456.47 (50,456) |
| | Full length | 149,573.54 (149,573) |
| cMet AA3 HK MBody | Light Chain | 24,284.34 (24,284) |
| | Heavy Chains | 50,348.09 (50,384) and |
| | | 50,662.76 (50,662) |
| | Full length | 149,573.72 (149,571) |
| cMet AA6 KH MBody | Light Chain | 24,284.49 (24,284) |
| | Heavy Chains | 50,525.56 (50,525) and |
| | | 50,456.68 (50,456) |
| | Full length | 149,545.39 (149,545) |
| cMet AA6 HK MBody | Light Chain | 24,284.38 (24,284) |
| | Heavy Chains | 50,320.69 (50,320) and |
| | | 50,662.15 (50,662) |
| | Full length | 149,543.95 (149,543) |

* Theoretical MW was shown in ( ).

Example 1.8: Determination of Antigen Binding Affinity of cMet MBody Molecules

The kinetics of MBody binding to rhcMetECD (extracellular domain) was determined by surface plasmon resonance-based measurements with a Biacore 3000 instrument (Biacore AB, Uppsala, Sweden) using HBS-EP (10 mM HEPES, pH 7.4, 150 mM NaCl, 3 mM EDTA, and 0.005% surfactant P20) at 25° C. All chemicals were obtained from Biacore AB (Uppsala, Sweden) or otherwise from a different source as described herein. Approximately, 5000 RU of goat anti-human IgG Fcγ fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 mg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-human IgG in flow cell 1 and 3 was used as the reference surface. For kinetic analysis, rate equations derived from the 1:1 Langmuir binding model were fitted simultaneously to association and dissociation phases of all ten injections (using global fit analysis) using the Bioevaluation 4.0.1 software. Purified MBody samples were diluted in HEPES-buffered saline for capture across goat anti-human IgG Fc specific reaction surfaces and injected over reaction matrices at a flow rate of 5 ml/min. The association and dissociation rate constants, kon (M-1 s-1) and koff (s-1) were determined under a continuous flow rate of 25 ml/min Rate constants were derived by making kinetic binding measurements at ten different antigen concentrations ranging from 1.25 to 1000 nM. The equilibrium dissociation constant (M) of the reaction between MBody and rhcMetECD was then calculated from the kinetic rate constants by the following formula: KD=koff/kon. Aliquots of rhcMetECD samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 5 ml/min. The anti-Fc antibody immobilized surfaces were completely regenerated and retained their full capture capacity over twelve cycles. The apparent stoichiometry of the captured MBody-rhcMetECD complex was calculated under saturating binding conditions (steady-state equilibrium) using the following formula:

$$\text{Stoichiometry} = \frac{rhcMetECD \text{ response } (RU)}{MBody \text{ response } (RU)} \times \frac{MBody \text{ } MW}{rhcMetECD \text{ } MW}$$

The Biacore analysis indicated the MBody molecules possessed similar binding kinetics and affinities to cMet as the original parental cMet mAbs (Table 11). The overall binding parameters of the five MBody molecules to rhcMetECD were similar, with the affinities of the cMet AA6 MBodies being only one fold less than that of the parental cMet mAb and other MBodies. Both parental cMet mAb and cMet mAb with knobs-into-holes mutations, being bivalent monospecific, bound to cMet on Biocore with a stoichiometry of 1.51 and 1.53, respectively. This is common for an IgG due to the large molecular mass of the antigen when antibodies are immobilized densely on the Biacore sense chip resulting in stoichiometry being in the range from 1.5 to 2.0. The stoichiometry parameters of all cMet MBody molecules for cMetECD ranged from 0.77 to 1.03, indicating that these cMet MBody molecules possessed monovalent binding capability to cMet antigen.

TABLE 11

Functional characterization of cMet MBody molecules by Biacore

| | $k_{on}$ (M-1 s-1) | $k_{off}$ (s-1) | $K_d$ (M) | Stoichiometry |
|---|---|---|---|---|
| cMet mAb | 8.03E+04 | 2.14E−04 | 2.67E−09 | 1.51 |
| cMet mAb KH | 9.36E+04 | 1.95E−04 | 2.08E−09 | 1.53 |
| cMet AA2 HK MBody | 9.76E+04 | 1.81E−04 | 1.88E−09 | 0.77 |
| cMet AA3 KH MBody | 10.6E+04 | 1.98E−04 | 1.98E−09 | 0.91 |
| cMet AA3 HK MBody | 13.9E+04 | 2.42E−04 | 1.99E−09 | 1.03 |
| cMet AA6 KH MBody | 7.51E+06 | 2.98E−04 | 3.98E−09 | 0.96 |
| cMet AA6 HK MBody | 7.52E+05 | 2.85E−04 | 3.80E−09 | 1.01 |

Example 1.9: Binding Analysis of cMet MBody Molecules by ELISA cMet binding ELISA was performed according to the method described in Example 1.3. The data showed that the antigen binding capability of cMet MBodies was about two fold lower as compared to that of cMet mAb (See Table 12 and FIG. 2). This might be due to loss of binding capability in one Fab arm of MBodies. The maximum binding of cMet MBodies was also lower than that of the bivalent cMet parental mAb.

TABLE 12

ELISA Binding Analysis of cMet MBody Molecules

| | $EC_{50}$ (nM) |
|---|---|
| cMet mAb | 0.35 |
| cMet AA2 KH MBody | 0.76 |
| cMet AA2 HK MBody | 0.73 |
| cMet AA3 KH MBody | 1.09 |
| cMet AA3 HK MBody | 0.78 |
| cMet AA6 KH MBody | 0.86 |
| cMet AA6 HK MBody | 1.02 |

Example 1.10: Anti-cMet MBody Molecules Inhibited Cancer Cell Proliferation

IM-95 (Cat. #1075. JCRB, Japan,) was also maintained in DMEM, 10% FBS with 10 mg/L Insulin. For the proliferation assay, IM-95 cells were plated in 96-well plate (Falcon 35-3075. BD Biosciences, Franklin Lakes, N.J.) in 180 µL, growth media at 5,000 cells/well. The cells were incubated overnight at 37° C. with 5% CO2. On Day 2, antibody dilutions were added to the cell plate (20 µL/well). Untreated control wells (for 0% control) and wells treated with 10 µM staurosporin (for 100% kill) were included in each plate. The plates were incubated for five days at 37° C. with 5% CO2. On Day 7 (five days after treatment), media was removed and 1× Cell Titer Aqueous One Solution (G3581. Promega, Madison, Wis.) diluted in Opti-mem media (Cat. #31985-070. Invitrogen, Carlsbad, Calif.) was added to plates and the plates were then incubated for one hour at 37° C. The OD at 490 nm was read on a M5 Spectramax plate reader (Molecular Probes, Carlsbad, Calif.). Percent inhibition was calculated based on 100% kill and untreated control wells using the following formula:

100×(0% control−treated)/(0% control−100% kill).

The parental cMet mAb efficiently inhibited IM95 cell proliferation with an EC50 at 0.17 µg/mL (See Table 13). Most cMet MBody molecules showed slight weaker capability in inhibition of IM95 cell proliferation, partially due to the stoichiometry difference between the parental mAb and cMet MBodies. Interestingly, cMet AA2 HK MBody inhibited the cancer cell proliferation almost as strongly as the parental mAb, indicating a potential superior in vivo efficacy.

TABLE 13

Inhibition of IM95 Proliferation by cMet MBody Molecules

| | $EC_{50}$ (µg/mL) |
|---|---|
| cMet mAb | 0.17 |
| cMet AA2 HK MBody | 0.23 |
| cMet AA3 KH MBody | 2.14 |
| cMet AA3 HK MBody | 1.60 |
| cMet AA6 KH MBody | 1.86 |
| cMet AA6 HK MBody | 2.73 |

Example 1.11: FcRn Binding Analysis of cMet MBody Molecules

Neonatal Fc receptor (FcRn) is present in the small intestine and on vascular endothelial cells. Neonatal Fc receptor is localized in acidic endosomes where it binds the Fc portion an IgG that has been taken in by pinocytocis. The IgG is then released back to the cell surface via the FcRn.

This process allows the control of IgG trafficking across single-layered epithelial barriers, and protects IgG molecules from catabolism, influencing the IgG half-life (See Blumberg R S & Fencer W I. Nature Biotechnology, 2005, 23: 1232-1234, incorporated herein by reference).

CHO-FcRnGPI cells (Stable FcRn receptor expressor) and CHO-pBud11 cells (non-FcRn expressor) were aliquotted into 96-well plates at $1\times10^5$ cells/well. Cells were resuspended in 150 μl FACS buffer. Anti-c-Met Ab and half-Ig binding proteins were diluted to 100 μg/ml in FACS buffer pH 6.4 and pH 7.4. 30 μl of diluted antibody or half-Ig binding protein was added to each well and incubated on ice for 1 hour. Following 2 washes with FACS buffer, 50 μl of secondary antibody R-phycoerythrin-conjugated AfiniPure F(ab')2 Fragment goat anti-human IgG (Jackson ImmunoResearch, West Grove, Pa.) diluted in FACS buffer pH 6.4 or pH7.4 was added. The mixture was incubated for 30 min on ice. The cells were resuspended in 100 μl PBS with 1% FBS (Invitrogen, Carlsbad, Calif.) and 2 μg/ml propidium iodide (Invitrogen, Carlsbad, Calif.) of the corresponding pH. Final FACS data were acquired on a FACScan (Becton Dickinson, Franklin Lakes, N.J.).

The parental cMet antibody showed strong binding to FcRn receptors. Since knobs-into-holes mutation sites are separated from FcRn binding sites, as expected, all cMet MBody molecules kept the binding capability to FcRn receptors to a full scale (See Table 14). In certain cases, a strong FcRn-IgG interaction is preferred in a therapeutic composition, as a higher-affinity FcRn-IgG interaction prolongs the half-lives of IgG and Fc-coupled drugs in the serum. The improved pharmacokinetics would reduce the dosing frequency of monoclonal antibodies and reduce patient risk and discomfort.

TABLE 14

FcRn Binding of cMet MBody Molecules at pH 6.4

| Molecule | EC50 (μg/mL) |
| --- | --- |
| cMet mAb | 53.27 |
| cMet mAb KH | 44.36 |
| cMet AA2 HK MBody | 31.46 |
| cMet AA3 KH MBody | 38.00 |
| cMet AA3 HK MBody | 34.79 |
| cMet AA6 KH MBody | 51.11 |
| cMet AA6 HK MBody | 47.14 |

Example 1.12: Pharmacokenetics Analysis of cMet MBody

Molecules Pharmacokinetic properties of cMet Mbodies were determined in CD-1 mice. Male mice were dosed intravenously with a single dose of 5 mg/kg of test Mbody molecules. Blood samples were collected at various time points. The serum samples were analyzed on a MSD Sector Imager 6000 (Meso Scale Discovery, Gaithersburg, Md.) in a chemiluminescent MSD method using biotinylated c-Met for capture and sulfo-TAG anti-human Ig Kappa for detection. Standard curve fitting and data evaluation was performed using XLfit4 software. A calibration curve was plotted from MSD chemiluminescence units versus theoretical standard concentrations. A four-parameter logistic model was used for curve fitting. The regression equation for the calibration curve was then used to back calculate the measured concentrations. The linear range was 0.027-20 μg/mL and the lower limit of quantitation (LLOQ) was 0.027 μg/mL. Pharmacokinetic parameters were calculated with PLASMA TemplateMaker rev 2.6.12 by non-compartmental analysis and linear trapezoidal method. Compared to the parental anti-c-Met antibody, both cMet AA2 HK MBody and cMet AA3 HK MBody had a longer half-life and lower clearance (Table 15). However, although the half-life was almost the same half-life as that of the parental antibody, cMet AA6 KH MBody had a slightly higher clearance rate at 0.926 ml/hr/k

TABLE 15

Anti-c-Met MBody pharmcokenetics in mice

| Test molecule | $t_{1/2}$ (hr) | $V_{ss}$ (L/kg) | $CL_P$ (mL/hr/kg) |
| --- | --- | --- | --- |
| Parental antibody | 297 | 0.168 | 0.418 |
| cMet AA2 HK MBody | 455 | 0.0875 | 0.135 |
| cMet AA3 HK MBody | 376 | 0.137 | 0.252 |
| cMet AA6 KH MBody | 297 | 0.422 | 0.926 |

Example 2: Anti-CD3 MBody Molecules

The CD3/TCR signaling is critical for T cell activation, linage selection, survival, antigen specificity, effector function and cytokine secretion (Guy D et al. Immunol Rev. 2009, 232: 7-21). A lot of effort has been made to target CD3 by antibody approaches for immune tolerance, anti-tumor, and anti-inflammation (Chatenoud L Nat Rev Immunol. 2003, 3: 123-132. Tibben J G et al. J. Natl Cancer Inst. 1993, 85: 1003-1004. Plevy S et al. Gastroenterology 2007, 133: 1414-1422). However, cytokine-release syndrome (CRS), an exaggerated systemic immune response involving release of a variety of cytokines, chemokines, oxygen radicals and complement factors, had been observed frequently in anti-CD3 treatment (Carpenter P A et al. J Immunol. 2000, 165: 6205-6213. Zlabinger G J et al. J Clin Immunol. 1992, 12: 170-177).

Multiple hypotheses regarding the molecular mechanisms by which an antibody can activate an effector cell and cause the release of cytokines had been proposed (Bugelski P J et al. Exp Rev Clin Immunol. 2009, 5: 499-521). Among those, activation of target cells via cross-linking of cell surface target by bivalent antibody had been supported by evidence generated from independent groups (Wilde M I et al. Transplantation 1996, 51: 865-894. Onrust S V et al. Drugs 1999, 58: 79-88. Adams A et al. J Immunol. 2005 174: 542-550). Interestingly, monovalent-targeting Ig-like binding molecules did not activate target cells in vitro (Pound J et al. International Immunol. 1999, 11: 11-20) and did not induce CRS or reduced CRS symptom in vivo (Abbs I C et al. Therap. Immunol. 1: 325-331).

Example 2.1: Molecular Cloning of Anti-CD3 HC and LC

As described in Example 1, the anti-CD3 OKT3 VH and VL cDNA sequences (Table 16, US patent application 2011/0263827) were cloned into pHybE-hCg1, z, non-a vectors and pHyBE-hCk, respectively. The amino acid sequences of VH, VL and full length of HC, LC were shown in Table 17 and Table 18.

TABLE 16

Anti-CD3 Variable Domain cDNA Sequences

| Domain | Sequence Identifier | Cloned cDNA Sequences |
|---|---|---|
| Anti-CD3 $V_H$ | SEQ ID NO: 19 | CAAGTCCAGCTGCAGCAGTCCGGCGCTGAGCTGGCCC<br>GACCCGGCGCTAGCGTGAAGATGTCATGCAAGGCCAG<br>CGGTTATACATTTACCAGGTACACTATGCATTGGGTG<br>AAACAGAGACCTGGACAGGGCCTCGAGTGGATCGGGT<br>ACATAAATCCCTCACGCGGCTATACAAACTACAATCA<br>GAAGTTCAAGGACAAGGCAACACTCACTACTGACAAG<br>AGCTCATCAACCGCCTATATGCAGTTGTCTTCACTGA<br>CCTCCGAGGACTCTGCAGTGTACTACTGCGCGCGGTA<br>CTACGACGACCACTACTGCCTCGACTACTGGGGGCAG<br>GGTACCACTCTGACCGTGTCCTCC |
| Anti-CD3 $V_L$ | SEQ ID NO: 20 | CAAATTGTTCTCACCCAGTCTCCAGCAATCATGTCTG<br>CATCTCCAGGGGAGAAGGTCACCATGACCTGCAGTGC<br>CAGCTCAAGTGTAAGTTACATGAACTGGTACCAGCAG<br>AAGTCAGGCACCTCCCCCAAAAGATGGATTTATGACA<br>CATCCAAACTGGCTTCTGGAGTCCCTGCTCACTTCAG<br>GGGCAGTGGGTCTGGGACCTCTTACTCTCTCACAATC<br>AGCGGCATGGAGGCTGAAGATGCTGCCACTTATTACT<br>GCCAGCAGTGGAGTAGTAACCCATTCACGTTCGGCTC<br>GGGGACAAAGTTGGAAATAAACCGG |

TABLE 17

Anti-CD3 Variable Domain Amino Acid Sequences

| Protein Region | Sequence Identifier | Amino acid sequence |
|---|---|---|
| Anti-CD3 $V_H$ | SEQ ID NO: 21 | QVQLQQSGAELARPGASVKMSCKASGYTFTRYTMHWV<br>KQRPGQGLEWIGYINPSRGYTNYNQKFKDKATLTTDK<br>SSSTAYMQLSSLTSEDSAVYYCARYYDDHYCLDYWGQ<br>GTTLTVSS |
| Anti-CD3 $V_L$ | SEQ ID NO: 22 | QIVLTQSPAIMSASPGEKVTMTCSASSSVSYMNWYQQ<br>KSGTSPKRWIYDTSKLASGVPAHFRGSGSGTSYSLTI<br>SGMEAEDAATYYCQQWSSNPFTFGSGTKLEINR |

40

TABLE 18

Anti-CD3 HC and LC Amino Acid Sequences

| Protein Region | Sequence Identifier | Amino acid sequence |
|---|---|---|
| Anti-CD3 HC | SEQ ID NO: 23 | QVQLQQSGAELARPGASVKMSCKASGYTFTRYTMHWV<br>KQRPGQGLEWIGYINPSRGYTNYNQKFKDKATLTTDK<br>SSSTAYMQLSSLTSEDSAVYYCARYYDDHYCLDYWGQ<br>GTTLTVSSASTKGPSVFPLAPSSKSTSGGTAALGCLV<br>KDYFPEPVTVSWNSGALTSGVHTFPAVLQSSGLYSLS<br>SVVTVPSSSLGTQTYICNVNHKPSNTKVDKKVEPKSC<br>DKTHTCPPCPAPELLGGPSVFLFPPKPKDTLMISRTP<br>EVTCVVVDVSHEDPEVKFNWYVDGVEVHNAKTKPREE<br>QYNSTYRVVSVLTVLHQDWLNGKEYKCKVSNKALPAP<br>IEKTISKAKGQPREPQVYTLPPSREEMTKNQVSLTCL<br>VKGFYPSDIAVEWESNGQPENNYKTTPPVLDSDGSFF<br>LYSKLTVDKSRWQQGNVFSCSVMHEALHNHYTQKSLS<br>LSPGK |
| Anti-CD3 LC | SEQ ID NO: 24 | QIVLTQSPAIMSASPGEKVTMTCSASSSVSYMNWYQQ<br>KSGTSPKRWIYDTSKLASGVPAHFRGSGSGTSYSLTI<br>SGMEAEDAATYYCQQWSSNPFTFGSGTKLEINRTVAA<br>PSVFIFPPSDEQLKSGTASVVCLLNNFYPREAKVQWK<br>VDNALQSGNSQESVTEQDSKDSTYSLSSTLTLSKADY<br>EKHKVYACEVTHQGLSSPVTKSFNRGEC |

Example 2.2: Introducing Mutations to Variable Domain to Abolish Anti-CD3 Antibody/Antigen Binding To abolish CD3 antigen binding, alanine-scanning method was used to introduce mutations to HC CDR3 region. Site-directed mutagenesis was used to introduce mutation combination to each specific position using methods well known in the art. The amino acid sequences of five HC mutants were shown in Table 19.

TABLE 19

Full Length Anti-CD3 HC with mutations

| Protein Region | Sequence Identifier | Amino Acid Sequence 12345678901234567890 |
|---|---|---|
| Anti-CD3-AA1 HC | SEQ ID NO: 25 | QVQLQQSGAELARPGASVKMSCKASGYTFTRYTMHWVKQRPGQ GLEWIGYINPSRGYTNYNQKFKDKATLTTDKSSSTAYMQLSSL TSEDSAVYYCARAADDHYCLDYWGQGTTLTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| Anti-CD3-AA2 HC | SEQ ID NO: 26 | QVQLQQSGAELARPGASVKMSCKASGYTFTRYTMHWVKQRPGQ GLEWIGYINPSRGYTNYNQKFKDKATLTTDKSSSTAYMQLSSL TSEDSAVYYCARYYAAHYCLDYWGQGTTLTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| Anti-CD3-AA3 HC | SEQ ID NO: 27 | QVQLQQSGAELARPGASVKMSCKASGYTFTRYTMHWVKQRPGQ GLEWIGYINPSRGYTNYNQKFKDKATLTTDKSSSTAYMQLSSL TSEDSAVYYCARYYDDAACLDYWGQGTTLTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| Anti-CD3-AA4 HC | SEQ ID NO: 28 | QVQLQQSGAELARPGASVKMSCKASGYTFTRYTMHWVKQRPGQ GLEWIGYINPSRGYTNYNQKFKDKATLTTDKSSSTAYMQLSSL TSEDSAVYYCARYYDDHYAADYWGQGTTLTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| Anti-CD3-AA5 HC | SEQ ID NO: 29 | QVQLQQSGAELARPGASVKMSCKASGYTFTRYTMHWVKQRPGQ GLEWIGYINPSRGYTNYNQKFKDKATLTTDKSSSTAYMQLSSL TSEDSAVYYCARYYDDHYCLAAWGQGTTLTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |

HEK 293 cells were transiently transfected by a CD3 HC and a CD3 LC constructs. The expressed antibodies were purified by a protein A column, as described in previous examples.

Example 2.3: Characterization of Antigen-binding Capability of Anti-CD3

Antibodies with $V_H$ Mutations by FACS

The antigen-binding capability of anti-CD3 antibodies with VH CDR3 mutations was assessed by a FACS assay. A431 and Jurkat cells were harvested and resuspended in FACS buffer (0.1% BSA, 0.1% $NaN_3$ in PBS) at $1\times10^6$ cell/ml. Added $2\times10^5$ cells/well in round bottom 96-well plate, incubated with testing antibodies for 1 hour at 4 degree. Followed washing, added 50 ul Alexa 488-anti-human IgG (1:300 dilution. Jackson Immunoresearch. Cat #: 109-546-098) and incubated for 30 min at 4 degree. After washing, cells were resuspended in 100 ul PBS and analyzed by BD FACSCanto II Among the five different mutation combinations, compared to the parental antibody with an EC50 at 0.27 nM, AA3 only slightly reduced the antigen-binding capability (EC50 at 0.53), while AA4 and AA5 did not show much impact. Both AA1 and AA2 mutations significantly reduced the antigen-binding capability. The AA1 curve was completely flat, just like that of a control antibody. The FACS data showed that the AA1 mutation completely abolished CD3-binding capability. Thus the AA1 mutation was chosen for the CD3 MBody and CD3/EGFR DVD MBody construction.

TABLE 20

FACS Binding Analysis of Anti-CD3 Antibodies With $V_H$ Mutations

| Antibody | $EC_{50}$ (nM) |
| --- | --- |
| Anti-CD3 Ig | 0.27 |
| Anti-CD3-AA1 Ig | No binding |
| Anti-CD3-AA2 Ig | No binding |
| Anti-CD3-AA3 Ig | 0.53 |
| Anti-CD3-AA4 Ig | 0.33 |
| Anti-CD3-AA5 Ig | 0.33 |

Example 2.4: Construction of Anti-CD3 MBody HC

Similar to the method described in Example 1.4, anti-CD3-AA1 mutations were combined with knob or hole mutations to be used in generation anti-CD3 MBodies. The details HC information was addressed in Table 21.

TABLE 21

Full Length CD3 HC Sequences with VH and Knobs-into-holes Mutations

| Protein Region | Sequence Identifier | Amino Acid Sequence 12345678901234567890 |
| --- | --- | --- |
| Anti-CD3-AA1-Knob HC | SEQ ID NO: 30 | QVQLQQSGAELARPGASVKMSCKASGYTFTRYTMHWVKQRP GQGLEWIGYINPSRGYTNYNQKFKDKATLTTDKSSSTAYMQ LSSLTSEDSAVYYCARAADDHYCLDYWGQGTTLTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAGQPREPQVYTLPPSREEMTKNQVSLWC LVKGFYPSDIAVEWESNGQPENNYKTTPPVLDSDGSFFLYS KLTVDKSRWQQGNVFSCSVMHEALHNHYTQKSLSLSPGK |
| Anti-CD3-Hole HC | SEQ ID NO: 31 | QVQLQQSGAELARPGASVKMSCKASGYTFTRYTMHWVKQRP GQGLEWIGYINPSRGYTNYNQKFKDKATLTTDKSSSTAYMQ LSSLTSEDSAVYYCARYYDDHYCLDYWGQGTTLTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAGQPREPQVYTLPPSREEMTKNQVSLSC AVKGFYPSDIAVEWESNGQPENNYKTTPPVLDSDGSFFLVS KLTVDKSRWQQGNVFSCSVMHEALHNHYTQKSLSLSPGK |
| Anti-CD3-AA1-hole HC | SEQ ID NO: 32 | QVQLQQSGAELARPGASVKMSCKASGYTFTRYTMHWVKQRP GQGLEWIGYINPSRGYTNYNQKFKDKATLTTDKSSSTAYMQ LSSLTSEDSAVYYCARAADDHYCLDYWGQGTTLTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALPAPIEKTISKAGQPREPQVYTLPPSREEMTKNQVSLSC AVKGFYPSDIAVEWESNGQPENNYKTTPPVLDSDGSFFLVS KLTVDKSRWQQGNVFSCSVMHEALHNHYTQKSLSLSPGK |
| Anti-CD3-knob HC | SEQ ID NO: 33 | QVQLQQSGAELARPGASVKMSCKASGYTFTRYTMHWVKQRP GQGLEWIGYINPSRGYTNYNQKFKDKATLTTDKSSSTAYMQ LSSLTSEDSAVYYCARYYDDHYCLDYWGQGTTLTVSSASTK GPSVFPLAPSSKSTSGGTAALGCLVKDYFPEPVTVSWNSGA LTSGVHTFPAVLQSSGLYSLSSVVTVPSSSLGTQTYICNVN |

TABLE 21-continued

Full Length CD3 HC Sequences with VH and Knobs-into-holes Mutations

| Protein Region | Sequence Identifier | Amino Acid Sequence<br>12345678901234567890 |
|---|---|---|
| | | HKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSNK<br>ALPAPIEKTISKAKGQPREPQVYTLPPSREEMTKNQVSLWC<br>LVKGFYPSDIAVEWESNGQPENNYKTTPPVLDSDGSFFLYS<br>KLTVDKSRWQQGNVFSCSVMHEALHNHYTQKSLSLSPGK |

Example 2.5: Transient Expression of Anti-CD3 MBody Molecules in 293 Cells

As described in Example 1.5, HEK 293 cells were co-transfected with three different HC and LC plasmid combination for transient expression of each anti-CD3 MBody molecule (Table 22).

TABLE 22

Plasmid Combination for Transient Transfection of HEK293 Cells to Express Anti-CD3 MBodies

| MBody | HC plasmid 1 | HC plasmid 2 | LC plasmid |
|---|---|---|---|
| CD3 AA1 HK MBody | Anti-CD3-AA1-hole HC | Anti-CD3-knob HC | Anti-CD3 LC |
| CD3 AA1 KH MBody | Anti-CD3-AA1-Knob HC | Anti-CD3-Hole HC | Anti-CD3 LC |

The transient expression level of both MBodies in 293 cells was high, with CD3 AA1 HK Mbody at 211.7 mg/L and CD3 AA1 KH Mbody at 54.9 mg/L (Table 23). SEC analysis showed both molecules with over 95% of monomer.

TABLE 23

Expression of CD3 MBodies in 293 Cells

| MBody | Expression Level (µg/ml) |
|---|---|
| CD3 AA1 HK MBody | 211.7 |
| CD3 AA1 KH MBody | 54.9 |

Example 2.6: Pharmacokinetics of Anti-CD3 MBodies

Pharmacokinetic properties CD3 Mbodies were determined in CD-1 mice. Male mice were dosed intravenously with a single dose of 5 mg/kg of test Mbody molecules. Blood samples were collected at various time points. The serum samples were analyzed on a MSD Sector Imager 6000 (Meso Scale Discovery, Gaithersburg, Md.) in a chemiluminescent MSD method using anti-human IgG Fc for capture and sulfo-TAG anti-human antibody for detection. Standard curve fitting and data evaluation was performed using XLfit4 software. A calibration curve was plotted from MSD chemiluminescence units versus theoretical standard concentrations. A four-parameter logistic model was used for curve fitting. The regression equation was then used to back calculate the measured concentrations. The linear range was 0.005-20 µg/mL and the lower limit of quantitation (LLOQ) was 0.005 µg/mL.

Pharmacokinetic parameters were calculated with PLASMA TemplateMaker rev 2.6.12 by non-compartmental analysis and linear trapezoidal method.

Both CD3 MBodies tested in CD-1 mice had decent half-life and clearance comparable to those of other regular antibodies. Interestingly, CD3 AA1 MBody, which is different from CD3 AA1 KH MBody only at CH3 interface region with a switch of knob and hole mutations between the 2 HCs, had a relatively shorter half-life of 231 hrs and a larger CLp at 0.420 mL/hr/kg (Table 24).

TABLE 24

Anti-CD3 MBody pharmcokenetics in mice

| Test molecule | $t_{1/2}$ (hr) | $V_{ss}$ (L/kg) | $CL_P$ (mL/hr/kg) |
|---|---|---|---|
| CD3 AA1 HK MBody | 231 | 0.145 | 0.420 |
| CD3 AA1 KH MBody | 344 | 0.110 | 0.229 |

Example 3: Anti-CD3/EGFR MBody Molecules

In development of strategies for immunotherapy of cancer, the approach of redirected cytotoxicity has gained more and more attention (Beun G et al Immunol Today 1994, 15: 11-15). Development of bispecific anti-T cell surface target X anti-tumor-idiotype antibodies greatly propelled the studies in redirected cytotoxicity. The idea is to recruit and activate cytotoxic T lymphocytes (CTL) to recognize and destroy selected target cancer cells. As early as 1985, Perez et al. demonstrated that a bispecific anti-CD3 X anti-tumor-idiotype antibody complex enabled CTLs to kill tumor cells in vitro (Perez P et al. Nature 1985, 316: 354-356). Demanet and colleagues presented that up to 80% of mice challenged with a lethal intraperitoneal injection of B cell lymphoma was cured by treatment of a single intravenous injection of bispecific anti-CD3 X anti-tumor-idiotype antibodies through redirected cytotoxicity (Demanet et al. J Immunol. 1991, 147:1091-1097). Recently, clinical trials with MT-103, a recombinant bispecific T-cell engager (BiTE) anti-CD3 X anti-CD19 antibody developed by Micromet AG and MedImmune Inc., demonstrated efficacy of this bispecific molecule in B-cell non-hodgkin's lymphoma (Bargou R et al. Science 2008, 321: 974-977) and B-precursor acute lymphocytic leukemia (Top M S et al ASH Abstract #174, 2010).

The epidermal growth factor receptor (EGFR) signal pathway is critical in tumor cell proliferation, local invasion, angiogenesis and metastasis (Rusch V et al. Clin Cancer Res. 1997, 3: 515-522). Anti-EGFR was demonstrated to be efficacious in different clinical trials (Pirker R et al. Lancet 2009, 373: 1525-1531 Khambata-Ford S et al. J Clin Oncol. 2010, 28: 918-927). An anti-CD3 X anti-EGFR MBody may kill cancer cells through redirect cytotoxicity. To generate anti-CD3 X anti-EGFR MBody molecules, alanine scanning mutations are introduced to one binding arm of H24 antibody (Abbott Laboratories) and knobs-into-holes mutations are introduced to its Fc region. The CD3 X anti-EGFR MBodies are characterized by SDS-PAGE, SEC and mass spectrometry to confirm it sequence, molecular weight and monomer status. A FACS assay is applied to determine the antigen-binding capability of these MBodies. A T cell activation assay or cytokine release assay is applied to determine the agonistic activity of these MBodies.

Example 3.1: Molecular Cloning of Anti-CD3/EGFR DVD HC and LC

As described in Example 1, the anti-CD3/EGFR VH and VL cDNA sequences (Table 25) were cloned into pHybE-hCg1, z, non-a vectors and pHyBE-hCk, respectively. The amino acid sequences of VH, VL and full length of HC, LC are shown in Table 26 and Table 27, respectively

TABLE 26

Anti-CD3/EGFR DVD-Ig Variable Domain cDNA Sequences

| Domain | Sequence Identifier | Cloned cDNA Sequences 12345678901234567890 |
|---|---|---|
| Anti-CD3/EGFR $V_H$ | SEQ ID NO: 34 | CAGGTTCAGCTCAAACAGAGCGGGCCCGGGCTGGTACAG CCCTCCCAGTCTCTTAGTATCACATGCACAGTCAGCGGG TTCAGCCTCACCAACTATGGGGTTCACTGGGTGCGCCAG TCACCTGGAAAGGGCTTGGAGTGGCTGGGCGTCATTTGG TCCGGAGGCAACACCGACTACAACACACCCTTCACTAGC CGGCTGAGCATTAACAAAGACAATAGCAAGTCCCAAGTG TTCTTTAAGATGAATAGCCTCCAATCTAACGACACAGCG ATTTACTATTGCGCCCGGGCCCTGACCTACTATGACTAT GAATTTGCCTACTGGGGCAAGGAACTCTGGTAACTGTA TCCGCTGCAAGCACGAAGGGGCCTAGCGTTTTCCCACTG GCTCCCCAAGTCCAGCTGCAGCAGTCCGGCGCTGAGCTG GCCCGACCCGGCGCTAGCGTGAAGATGTCATGCAAGGCC AGCGGTTATACATTTACCAGGTACACTATGCATTGGGTG AAACAGAGACCTGGACAGGGCCTCGAGTGGATCGGGTAC ATAAATCCCTCACGCGGCTATACAAACTACAATCAGAAG TTCAAGGACAAGGCGACACTCACTACTGACAAGAGCTCA TCAACCGCCTATATGCAGTTGTCTTCACTGACCTCCGAG GACTCTGCAGTGTACTACTGCGCGCGGTACTACGACGAC CACTACTGCCTCGACTACTGGGGCAGGGTACCACTCTG ACCGTGTCCTCC |
| Anti-CD3/EGFR $V_L$ | SEQ ID NO: 35 | GATATCCTTCTGACACAAAGTCCTGTAATCCTTTCCGTT AGCCCGGGTGAGAGGGTCTCTTTCAGCTGTAGAGCGTCC CAGTCCATCGGTACCAACATCCACTGGTATCAGCAGCGG ACCAATGGTAGCCCACGACTTCTCATCAAGTACGCAAGT GAATCAATTAGTGGAATCCCTTCCCGGTTTTCTGGATCA GGCTCTGGTACGGACTTCACGCTGAGCATCAACTCTGTC GAATCCGAGGATATCGCTGACTACTACTGCCAGCAAAAT AATAATTGGCCAACGACATTTGGCGCCGGGACTAAGCTT GAACTGAAACGGACCGTGGCAGCCCCTAGTGTGTTCATC TTTCCACCCCAGATTGTTCTGACCCAGAGCCCGGCTATA ATGAGTGCCTCTCCAGGTGAGAAGGTCACCATGACATGT CGAGCCTCTTCCTCCGTTTCTTACATGAACTGGTATCAA CAGAAGTCCGGAACTTCCCCTAAACGGTGGATTTATGAT ACTAGCAAAGTTGCCAGCGGTGTGCCATATCGCTTTAGC GGGAGCGGTAGCGGGACCAGTTATAGTTTGACCATCAGC AGCATGGAAGCAGAGGATGCGGCCACTTATTATTGCCAA CAATGGTCCAGCAACCCTTTGACTTTCGGTAGTGGCACT AAGCTTGAGATCAATCGC |

TABLE 27

Anti-CD3/EGFR DVD-Ig Variable Domain Amino Acid Sequences

| Protein Region | Sequence Identifier | Amino acid sequence 12345678901234567890 |
|---|---|---|
| Anti-CD3/EGFR $V_H$ | SEQ ID NO: 36 | QVQLKQSGPGLVQPSQSLSITCTVSGFSLTNYGVHWVRQ SPGKGLEWLGVIWSGGNTDYNTPFTSRLSINKDNSKSQV FFKMNSLQSNDTAIYYCARALTYYDYEFAYWGQGTLVTV SAASTKGPSVFPLAPQVQLQQSGAELARPGASVKMSCKA SGYTFTRYTMHWVKQRPGQGLEWIGYINPSRGYTNYNQK FKDKATLTTDKSSSTAYMQLSSLTSEDSAVYYCARYYDD HYCLDYWGQGTTLTVSS |

TABLE 27-continued

Anti-CD3/EGFR DVD-Ig Variable Domain Amino Acid Sequences

| Protein Region | Sequence Identifier | Amino acid sequence 12345678901234567890 |
|---|---|---|
| Anti-CD3/EGFR V$_L$ | SEQ ID NO: 37 | DILLTQSPVILSVSPGERVSFSCRASQSIGTNIHWYQQR TNGSPRLLIKYASESISGIPSRFSGSGSGTDFTLSINSV ESEDIADYYCQQNNNWPTTFGAGTKLELKR<u>TVAAPSVFI FPP</u>QIVLTQSPAIMSASPGEKVTMTCRASSSVSYMNWYQ QKSGTSPKRWIYDTSKVASGVPYRFSGSGSGTSYSLTIS SMEAEDAATYYCQQWSSNPLTFGSGTKLEINR |

TABLE 28

Anti-CD3/EGFR DVD-Ig HC and LC Amino Acid Sequences

| Protein Region | Sequence Identifier | Amino acid sequence 12345678901234567890 |
|---|---|---|
| Anti-CD3/EGFR HC | SEQ ID NO: 38 | QVQLKQSGPGLVQPSQSLSITCTVSGFSLTNYGVHWVRQ SPGKGLEWLGVIWSGGNTDYNTPFTSRLSINKDNSKSQV FFKMNSLQSNDTAIYYCARALTYYDYEFAYWGQGTLVTV SA<u>ASTKGPSVFPLAP</u>QVQLQQSGAELARPGASVKMSCKA SGYTFTRYTMHWVKQRPGQGLEWIGYINPSRGYTNYNQK FKDKATLTTDKSSSTAYMQLSSLTSEDSAVYYCARYYDD HYCLDYWGQGTTLTVSSASTKGPSVFPLAPSSKSTSGGT AALGCLVKDYFPEPVTVSWNSGALTSGVHTFPAVLQSSG LYSLSSVVTVPSSSLGTQTYICNVNHKPSNTKVDKKVEP KSCDKTHTCPPCPAPELLGGPSVFLFPPKPKDTLMISRT PEVTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSREEMTKNQVSLTCLVKGFY PSDIAVEWESNGQPENNYKTTPPVLDSDGSFFLYSKLTV DKSRWQQGNVFSCSVMHEALHNHYTQKSLSLSPGK |
| Anti-CD3/EGFR LC | SEQ ID NO: 39 | DILLTQSPVILSVSPGERVSFSCRASQSIGTNIHWYQQR TNGSPRLLIKYASESISGIPSRFSGSGSGTDFTLSINSV ESEDIADYYCQQNNNWPTTFGAGTKLELKR<u>TVAAPSVFI FPP</u>QIVLTQSPAIMSASPGEKVTMTCRASSSVSYMNWYQ QKSGTSPKRWIYDTSKVASGVPYRFSGSGSGTSYSLTIS SMEAEDAATYYCQQWSSNPLTFGSGTKLEINRTVAAPSV FIFPPSDEQLKSGTASVVCLLNNFYPREAKVQWKVDNAL QSGNSQESVTEQDSKDSTYSLSSTLTLSKADYEKHKVYA CEVTHQGLSSPVTKSFNRGEC |

Example 3.2: Construction of Anti-CD3/EGFR DVD MBody HC

Similar to the method described in Example 1.4, anti-CD3-AA1 mutations were combined with knob or hole mutations to be used in generation of anti-CD3/EGFR DVD MBodies. The details HC information was addressed in Table 29.

TABLE 29

Full Length CD3/EGFR HC Sequences with VH and Knobs-into-holes Mutations

| Protein Region | Sequence Identifier | Amino Acid Sequence 12345678901234567890 |
|---|---|---|
| Anti-CD3 AA1/EGFR-Knob HC | SEQ ID NO: 40 | QVQLKQSGPGLVQPSQSLSITCTVSGFSLTNYGVHWVRQ SPGKGLEWLGVIWSGGNTDYNTPFTSRLSINKDNSKSQV FFKMNSLQSNDTAIYYCARALTYYDYEFAYWGQGTLVTV SA<u>ASTKGPSVFPLAP</u>QVQLQQSGAELARPGASVKMSCKA SGYTFTRYTMHWVKQRPGQGLEWIGYINPSRGYTNYNQK FKDKATLTTDKSSSTAYMQLSSLTSEDSAVYYCARAADD HYCLDYWGQGTTLTVSSASTKGPSVFPLAPSSKSTSGGT AALGCLVKDYFPEPVTVSWNSGALTSGVHTFPAVLQSSG LYSLSSVVTVPSSSLGTQTYICNVNHKPSNTKVDKKVEP KSCDKTHTCPPCPAPELLGGPSVFLFPPKPKDTLMISRT PEVTCVVVDVSHEDPEVKFNWYVDGVEVHNAKTKPREEQ YNSTYRVVSVLTVLHQDWLNGKEYKCKVSNKALPAPIEK |

TABLE 29-continued

Full Length CD3/EGFR HC Sequences with VH and Knobs-into-holes Mutations

| Protein Region | Sequence Identifier | Amino Acid Sequence 12345678901234567890 |
|---|---|---|
| | | TISKAKGQPREPQVYTLPPSREEMTKNQVSLWCLVKGFY<br>PSDIAVEWESNGQPENNYKTTPPVLDSDGSFFLYSKLTV<br>DKSRWQQGNVFSCSVMHEALHNHYTQKSLSLSPGK |
| Anti-CD3/EGFR-Hole HC | SEQ ID NO: 41 | QVQLKQSGPGLVQPSQSLSITCTVSGFSLTNYGVHWVRQ<br>SPGKGLEWLGVIWSGGNTDYNTPFTSRLSINKDNSKSQV<br>FFKMNSLQSNDTAIYYCARALTYYDEFAYWGQGTLVTV<br>SA<u>ASTKGPSVFPLAP</u>QVQLQQSGAELARPGASVKMSCKA<br>SGYTFTRYTMHWVKQRPGQGLEWIGYINPSRGYTNYNQK<br>FKDKATLTTDKSSSTAYMQLSSLTSEDSAVYYCARYYDD<br>HYCLDYWGQGTTLTVSSASTKGPSVFPLAPSSKSTSGGT<br>AALGCLVKDYFPEPVTVSWNSGALTSGVHTFPAVLQSSG<br>LYSLSSVVTVPSSSLGTQTYICNVNHKPSNTKVDKKVEP<br>KSCDKTHTCPPCPAPELLGGPSVFLFPPKPKDTLMISRT<br>PEVTCVVVDVSHEDPEVKFNWYVDGVEVHNAKTKPREEQ<br>YNSTYRVVSVLTVLHQDWLNGKEYKCKVSNKALPAPIEK<br>TISKAKGQPREPQVYTLPPSREEMTKNQVSLSCAVKGFY<br>PSDIAVEWESNGQPENNYKTTPPVLDSDGSFFLVSKLTV<br>DKSRWQQGNVFSCSVMHEALHNHYTQKSLSLSPGK |
| Anti-CD3 AA1/EGFR-hole HC | SEQ ID NO: 42 | QVQLKQSGPGLVQPSQSLSITCTVSGFSLTNYGVHWVRQ<br>SPGKGLEWLGVIWSGGNTDYNTPFTSRLSINKDNSKSQV<br>FFKMNSLQSNDTAIYYCARALTYYDEFAYWGQGTLVTV<br>SA<u>ASTKGPSVFPLAP</u>QVQLQQSGAELARPGASVKMSCKA<br>SGYTFTRYTMHWVKQRPGQGLEWIGYINPSRGYTNYNQK<br>FKDKATLTTDKSSSTAYMQLSSLTSEDSAVYYCARAADD<br>HYCLDYWGQGTTLTVSSASTKGPSVFPLAPSSKSTSGGT<br>AALGCLVKDYFPEPVTVSWNSGALTSGVHTFPAVLQSSG<br>LYSLSSVVTVPSSSLGTQTYICNVNHKPSNTKVDKKVEP<br>KSCDKTHTCPPCPAPELLGGPSVFLFPPKPKDTLMISRT<br>PEVTCVVVDVSHEDPEVKFNWYVDGVEVHNAKTKPREEQ<br>YNSTYRVVSVLTVLHQDWLNGKEYKCKVSNKALPAPIEK<br>TISKAKGQPREPQVYTLPPSREEMTKNQVSLSCAVKGFY<br>PSDIAVEWESNGQPENNYKTTPPVLDSDGSFFLVSKLTV<br>DKSRWQQGNVFSCSVMHEALHNHYTQKSLSLSPGK |
| Anti-CD3/EGFR-knob HC | SEQ ID NO: 43 | QVQLKQSGPGLVQPSQSLSITCTVSGFSLTNYGVHWVRQ<br>SPGKGLEWLGVIWSGGNTDYNTPFTSRLSINKDNSKSQV<br>FFKMNSLQSNDTAIYYCARALTYYDEFAYWGQGTLVTV<br>SA<u>ASTKGPSVFPLAP</u>QVQLQQSGAELARPGASVKMSCKA<br>SGYTFTRYTMHWVKQRPGQGLEWIGYINPSRGYTNYNQK<br>FKDKATLTTDKSSSTAYMQLSSLTSEDSAVYYCARYYDD<br>HYCLDYWGQGTTLTVSSASTKGPSVFPLAPSSKSTSGGT<br>AALGCLVKDYFPEPVTVSWNSGALTSGVHTFPAVLQSSG<br>LYSLSSVVTVPSSSLGTQTYICNVNHKPSNTKVDKKVEP<br>KSCDKTHTCPPCPAPELLGGPSVFLFPPKPKDTLMISRT<br>PEVTCVVVDVSHEDPEVKFNWYVDGVEVHNAKTKPREEQ<br>YNSTYRVVSVLTVLHQDWLNGKEYKCKVSNKALPAPIEK<br>TISKAKGQPREPQVYTLPPSREEMTKNQVSLWCLVKGFY<br>PSDIAVEWESNGQPENNYKTTPPVLDSDGSFFLYSKLTV<br>DKSRWQQGNVFSCSVMHEALHNHYTQKSLSLSPGK |

Example 3.3: Transient Expression of Anti-CD3/EGFR DVD MBody Molecules in 293 Cells As described in Example 1.5, HEK 293 cells were co-transfected with three different HC and LC plasmid combination for transient expression of each anti-CD3/EGFR DVD MBody molecule (Table 30).

TABLE 30

Plasmid Combination for Transient Transfection of HEK293 Cells to Express Anti-CD3/EGFR DVD MBodies

| MBody | HC plasmid 1 | HC plasmid 2 | LC plasmid |
|---|---|---|---|
| CD3 AA1/EGFR HK DVD MBody | Anti-CD3 AA1/EGFR-hole HC | Anti-CD3/EGFR-knob HC | Anti-CD3/EGFR LC |
| CD3 AA1/EGFR KH DVD MBody | Anti-CD3 AA1/EGFR-Knob HC | Anti-CD3/EGFR-Hole HC | Anti-CD3/EGFR LC |

The transient expression level of both MBodies in 293 cells was reasonable for DVD-Ig molecules, with CD3 AA1/EGFR HK DVD MBody at 15.4 mg/L and CD3 AA1/EGFR KH DVD MBody at 26.2 mg/L (Table 31). SEC analysis showed both molecules with over 95% of monomer.

TABLE 31

Expression of MBody DVD-Ig molecules in 293 Cells

| MBody | Expression Level (μg/ml) |
|---|---|
| CD3 AA1/EGFR HK DVD MBody | 15.4 |
| CD3 AA1/EGFR KH DVD MBody | 26.2 |

Example 3.4: Antigen Binding of Anti-CD3/EGFR MBody Molecules

The binding of anti-CD3/EGFR Mbody to CD3 was characterized as described in Example 2.3. While the EC50 of binding of the parental DVD-Ig was at 1942 μM, the EC50 s of CD3 AA1/EGFR HK DVD MBody and CD3 AA1/EGFR KH DVD MBody were maintained well at 1231 and 1797 μM, respectively (Table 32).

TABLE 32

FACS analysis of anti-CD3/EGFR Mbody molecules binding in A431 cells

| MBody | EC50 (pM) |
|---|---|
| CD3 AA1/EGFR HK DVD MBody | 1231 |
| CD3 AA1/EGFR KH DVD MBody | 1797 |
| CD3/EGFR DVD-Ig | 1942 |

Example 3.5: Characterization of rCTL Anti-CD3/EGFR MBody Molecules

Redirected Cytotoxicity Assays were performed as Impedence-based assays (Zhu, J., et al. 2006. J Immunological Methods 309:25-33). T cells were prepared as above. EGFR-expressing target cells were allowed to adhere to ACEA RT-CES 96-well plates (ACEA Bio, San Diego) overnight. Effector T cells (E) and targets (T) were then plated at $2\times10^5$ and $2\times10^4$ cells/well to give an E:T ratio of 10:1. DVD-Ig and Mbody DVD-Ig molecules were appropriately diluted to obtain concentration-dependent titration curves. The cell indexes of targets in the Mbody DVD-Ig binding protein treated samples were divided by the cell indexes of control targets (no treatment) to calculate percent specific lysis. The data was graphed and IC50 s are calculated in Prism (Graphpad). The result of impedance assay showed that, compared to the parental anti-C3/EGFR DVD-Ig molecule with an EC50 at 87.9 μM, both CD3 AA1/EGFR HK DVD MBody and CD3 AA1/EGFR KH DVD MBody maintained the rCTL with a relatively larger EC50 at 703.0 μM and 336.9 μM, respectively (Table 33).

TABLE 33 rCTL analysis of anti-CD3/EGFR Mbody molecules in impedance assay

| MBody | EC50 (pM) |
|---|---|
| CD3 AA1/EGFR HK DVD MBody | 703.0 |
| CD3 AA1/EGFR KH DVD MBody | 336.9 |
| CD3/EGFR DVD-Ig | 87.9 |

Example 3.6: Cytokine Releasing Activity of Anti-CD3/EGFR MBody Molecules

Test antibodies were coated onto a 96-well polypropylene plate at 1 μg/well in PBS for 90 minutes at room temperature. The plate was rinsed and human PBMC were added at $10^5$ cells/well. After 48 hours of culture, supernatants were harvested and assayed for cytokines using commercially available kits (Meso Scale Discovery, Rockville, Md.)

Compared with the parental DVD molecule which potently stimulated non-specific cytokine releasing (40661 pg/mL, averaged number from three donors), the CD3 AA1/EGFR HK DVD MBody induced less IFNg production in the assay by 68% (Table 34).

TABLE 34

Characterization of anti-CD3/EGFR Mbody molecules in IFNg releasing assay

| MBody | Average of IFNg (pg/mL) |
|---|---|
| CD3 AA1/EGFR HK DVD MBody | 13072 |
| CD3/EGFR DVD-Ig | 40661 |

Example 3.7: Pharmacokinetics of Anti-CD3/EGFR DVD MBody Molecules

The method for determination of PK of the anti-CD3/EGFR DVD MBodies is the same as what in Example 2.4.

The parental anti-CD3/EGFR DVD-Ig, with a relatively high CLp at 1.39 mL/hr/kg, displayed a half-life of 211 hrs. With slightly higher CLp, CD3 AA1/EGFR HK DVD MBody had a half-life of 217 hrs. However, CD3 AA1/EGFR KH DVD MBody, with a CLp at 1.62 mL/hr/kg, had the relatively short half-life at 146 hrs (Table 35).

TABLE 35

Anti-CD3/EGFR DVD MBody pharmcokenetics in mice

| Test molecule | $t_{1/2}$ (hr) | $V_{ss}$ (L/kg) | $CL_P$ (mL/hr/kg) |
|---|---|---|---|
| Parental DVD-Ig | 211 | 0.297 | 1.390 |
| CD3 AA1/EGFR HK DVD MBody | 217 | 0.348 | 1.560 |
| CD3 AA1/EGFR KH DVD MBody | 146 | 0.248 | 1.620 |

Example 4: Anti-CD40 MBody Molecules

Example 4.1: Molecular Cloning of Anti-CD40 HC and LC

As described in Example 1, the anti-CD40 21.4.1 VH and VL cDNA sequences (Table 28, US patent application 2005/063289) were cloned into pHybE-hCg1, z, non-a vectors and pHyBE-hCk, respectively. The amino acid sequences of VH, VL and full length of HC, LC were shown in Table 36 and Table 37.

TABLE 36

Anti-CD40 Variable Domain cDNA Sequences

| Domain | Sequence Identifier | Cloned cDNA Sequences |
|---|---|---|
| Anti-CD40 $V_H$ | SEQ ID NO: 44 | CAAGTCCAGCTGGTGCAGAGCGGGGCGGAGGTCAAAA<br>AGCCGGGGGCAAGCGTCAAGGTGAGCTGTAAAGCTAG<br>TGGTTACACCTTTACCGGGTATTACATGCATTGGGTG<br>CGGCAGGCGCCCGGCCAAGGGCTCGAATGGATGGGTT<br>GGATAAACCCAGATTCCGGCGGAACAAACTATGCGCA<br>GAAATTCCAGGGCAGAGTCACCATGACCAGGGATACC<br>TCTATCTCTACGGCTTACATGGAGTTGAACCGCCTGC<br>GCAGCGATGACACAGCTGTCTACTATTGCGCGAGGGA<br>TCAGCCACTGGGCTACTGCACCAATGGCGTGTGCAGC<br>TATTTCGACTACTGGGGTCAGGGAACCCTCGTGACCG<br>TTTCCTCC |
| Anti-CD40 $V_L$ | SEQ ID NO: 45 | GATATCCAGATGACCCAGTCACCCAGCAGCGTCTCTG<br>CCTCCGTTGGCGACCGCGTCACGATTACGTGCAGGGC<br>TAGTCAGGGGATTTATTCCTGGCTCGCCTGGTACCAA<br>CAGAAACCTGGCAAAGCTCCTAACTTGCTCATATATA<br>CTGCTAGCACTCTGCAATCAGGTGTGCCGAGTCGATT<br>TTCCGGGAGCGGTTCCGGCACCGATTTTACCCTGACA<br>ATCTCATCCCTTCAGCCCGAAGATTTTGCCACCTACT<br>ACTGCCAGCAGGCTAACATCTTCCCTCTCACCTTCGG<br>TGGGGGAACCAAAGTAGAAATCAAGAGG |

TABLE 37

Anti-CD40 Variable Domain Amino Acid Sequences

| Protein Region | Sequence Identifier | Amino acid sequence |
|---|---|---|
| Anti-CD40 $V_H$ | SEQ ID NO: 46 | QVQLVQSGAEVKKPGASVKVSCKASGYTFTGYYMHWV<br>RQAPGQGLEWMGWINPDSGGTNYAQKFQGRVTMTRDT<br>SISTAYMELNRLRSDDTAVYYCARDQPLGYCTNGVCS<br>YFDYWGQGTLVTVSS |
| Anti-CD40 $V_L$ | SEQ ID NO: 47 | DIQMTQSPSSVSASVGDRVTITCRASQGIYSWLAWYQ<br>QKPGKAPNLLIYTASTLQSGVPSRFSGSGSGTDFTLT<br>ISSLQPEDFATYYCQQANIFPLTFGGGTKVEIKR |

TABLE 38

Anti-CD40 HC and LC Amino Acid Sequences

| Protein Region | Sequence Identifier | Amino acid sequence |
|---|---|---|
| Anti-CD40 HC | SEQ ID NO: 48 | QVQLVQSGAEVKKPGASVKVSCKASGYTFTGYYMHWVRQ<br>APGQGLEWMGWINPDSGGTNYAQKFQGRVTMTRDTSIST<br>AYMELNRLRSDDTAVYYCARDQPLGYCTNGVCSYFDYWG<br>QGTLVTVSSASTKGPSVFPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKKVEPKSCDKTHT<br>CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQG<br>NVFSCSVMHEALHNHYTQKSLSLSPGK |
| Anti-CD40 LC | SEQ ID NO: 49 | DIQMTQSPSSVSASVGDRVTITCRASQGIYSWLAWYQQK<br>PGKAPNLLIYTASTLQSGVPSRFSGSGSGTDFTLTISSL<br>QPEDFATYYCQQANIFPLTFGGGTKVEIKRTVAAPSVFI<br>FPPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC |

Example 4.2: Introducing Mutations to Variable Domain to Abolish Anti-CD40 Antibody/Antigen Binding To abolish the antigen binding, specific mutations at HC CDR3 region were designed based on antibody structure analysis. Site-directed mutagenesis was used to introduce mutation combination to each specific position using methods well known in the art. The amino acid sequences of five HC mutants were shown in Table 39.

TABLE 39

Full Length Anti-CD40 HC with mutations

| Protein Region | Sequence Identifier | Amino Acid Sequence 12345678901234567890 |
|---|---|---|
| Anti-CD40-LYNV HC | SEQ ID NO: 50 | QVQLVQSGAEVKKPGASVKVSCKASGYTFTGYYMHWVRQA PGQGLEWMGWINPDSGGTNYAQKFQGRVTMTRDTSISTAY MELNRLRSDDTAVYYCARDQPAGACTAGACSYFDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTL PPSREEMTKNQVSLTCLVKGFYPSDIAVEWESNGQPENNY KTTPPVLDSDGSFFLYSKLTVDKSRWQQGNVFSCSVMHEA LHNHYTQKSLSLSPGK |
| Anti-CD40-YNV HC | SEQ ID NO: 51 | QVQLVQSGAEVKKPGASVKVSCKASGYTFTGYYMHWVRQA PGQGLEWMGWINPDSGGTNYAQKFQGRVTMTRDTSISTAY MELNRLRSDDTAVYYCARDQPLGACTAGACSYFDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTL PPSREEMTKNQVSLTCLVKGFYPSDIAVEWESNGQPENNY KTTPPVLDSDGSFFLYSKLTVDKSRWQQGNVFSCSVMHEA LHNHYTQKSLSLSPGK |
| Anti-CD40-VA HC | SEQ ID NO: 52 | QVQLVQSGAEVKKPGASVKVSCKASGYTFTGYYMHWVRQA PGQGLEWMGWINPDSGGTNYAQKFQGRVTMTRDTSISTAY MELNRLRSDDTAVYYCARDQPLGYCTNGACSYFDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTL PPSREEMTKNQVSLTCLVKGFYPSDIAVEWESNGQPENNY KTTPPVLDSDGSFFLYSKLTVDKSRWQQGNVFSCSVMHEA LHNHYTQKSLSLSPGK |
| Anti-CD40-LA HC | SEQ ID NO: 53 | QVQLVQSGAEVKKPGASVKVSCKASGYTFTGYYMHWVRQA PGQGLEWMGWINPDSGGTNYAQKFQGRVTMTRDTSISTAY MELNRLRSDDTAVYYCARDQPAGYCTNGVCSYFDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTL PPSREEMTKNQVSLTCLVKGFYPSDIAVEWESNGQPENNY KTTPPVLDSDGSFFLYSKLTVDKSRWQQGNVFSCSVMHEA LHNHYTQKSLSLSPGK |
| Anti-CD40-NA HC | SEQ ID NO: 54 | QVQLVQSGAEVKKPGASVKVSCKASGYTFTGYYMHWVRQA PGQGLEWMGWINPDSGGTNYAQKFQGRVTMTRDTSISTAY MELNRLRSDDTAVYYCARDQPLGYCTAGVCSYFDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVLHQ |

TABLE 39-continued

Full Length Anti-CD40 HC with mutations

| Protein Region | Sequence Identifier | Amino Acid Sequence 12345678901234567890 |
|---|---|---|
| | | DWLNGKEYKCKVSNKALPAPIEKTISKAKGQPREPQVYTL<br>PPSREEMTKNQVSLTCLVKGFYPSDIAVEWESNGQPENNY<br>KTTPPVLDSDGSFFLYSKLTVDKSRWQQGNVFSCSVMHEA<br>LHNHYTQKSLSLSPGK |
| Anti-CD40-<br>YA HC | SEQ ID<br>NO: 55 | QVQLVQSGAEVKKPGASVKVSCKASGYTFTGYYMHWVRQA<br>PGQGLEWMGWINPDSGGTNYAQKFQGRVTMTRDTSISTAY<br>MELNRLRSDDTAVYYCARDQPLGACTNGVCSYFDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCPA<br>PELLGGPSVFLFPPKPKDTLMISRTPEVTCVVVDVSHEDP<br>EVKFNWYVDGVEVHNAKTKPREEQYNSTYRVVSVLTVLHQ<br>DWLNGKEYKCKVSNKALPAPIEKTISKAKGQPREPQVYTL<br>PPSREEMTKNQVSLTCLVKGFYPSDIAVEWESNGQPENNY<br>KTTPPVLDSDGSFFLYSKLTVDKSRWQQGNVFSCSVMHEA<br>LHNHYTQKSLSLSPGK |

Example 4.3: Transient Expression of Anti-CD40 MBody Molecules in 293 Cells

HEK 293 cells were transiently transfected by a CD40 HC and a CD40 LC constructs. The expressed antibodies were purified by a protein A column, as described in previous examples.

Example 4.4: Antigen Binding Capability of Anti-CD40 Antibodies with HC CDR3 Mutations The binding capability of 21.4.1 antibodies with HC CDR3 mutations was measured by FACS. First, the CD40-overexpressing HEK 293 cells were stained with hIgG1 or testing material at a range of 0.01 µg/ml to 10 µg/ml. Followed by 30 min incubation on ice with an APC-conjugated anti-human Fc antibody. Cells then are washed twice and resuspended in PBS/FBS. Fluorescence was measured using a Becton Dickinson FACSCalibur (Becton Dickinson, San Jose, Calif.).

The binding of proteins were examined by FACS. 21.4.1 anti-CD40 antibody CD40 at an EC50 of 0.084 µg/mL. VA, LA NA and YA mutations had only partially impacted the binding. LYNV and YNV mutations both reduced binding significantly (Table 40). LYNV mutation was selected for anti-CD40 MBody construction.

TABLE 40

FACS Binding Analysis of Anti-CD40 Antibodies With HC CDR3 Mutations

| Antibody | EC$_{50}$ (µg/mL) |
|---|---|
| Anti-CD40 Ig | 0.084 |
| Anti-CD40 LYNV | No binding |
| Anti-CD40 YNV | No binding |
| Anti-CD40 VA | 0.125 |
| Anti-CD40 LA | 0.189 |
| Anti-CD40 NA | 2.124 |
| Anti-CD40 YA | 0.095 |

Example 4.5: Generation of Anti-CD40 HC with Knob and Hole Mutations

Anti-CD40 WT HC and LYNV HC were coupled with knob or hole mutations for the final CD40 MBody generation (Table 41).

TABLE 41

Full Length Anti-CD40 HC with Knob and Hole Mutations

| Protein Region | Sequence Identifier | Amino Acid Sequence 12345678901234567890 |
|---|---|---|
| Anti-CD40-<br>LYNV knob<br>HC | SEQ ID<br>NO: 56 | QVQLVQSGAEVKKPGASVKVSCKASGYTFTGYYMHWVRQ<br>APGQGLEWMGWINPDSGGTNYAQKFQGRVTMTRDTSIST<br>AYMELNRLRSDDTAVYYCARDQPAGACTAGACSYFDYWG<br>QGTLVTVSSASTKGPSVFPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKKVEPKSCDKTHT<br>CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLWCLVKGFYPSDIAVEW<br>ESNGQPENNYKTTPPVLDSDGSFFLYSKLTVDKSRWQQG<br>NVFSCSVMHEALHNHYTQKSLSLSPGK |
| Anti-CD40-<br>hole HC | SEQ ID<br>NO: 57 | QVQLVQSGAEVKKPGASVKVSCKASGYTFTGYYMHWVRQ<br>APGQGLEWMGWINPDSGGTNYAQKFQGRVTMTRDTSIST<br>AYMELNRLRSDDTAVYYCARDQPLGYCTNGVCSYFDYWG<br>QGTLVTVSSASTKGPSVFPLAPSSKSTSGGTAALGCLVK<br>DYFPEPVTVSWNSGALTSGVHTFPAVLQSSGLYSLSSVV |

TABLE 41-continued

Full Length Anti-CD40 HC with Knob and Hole Mutations

| Protein Region | Sequence Identifier | Amino Acid Sequence<br>12345678901234567890 |
|---|---|---|
|  |  | TVPSSSLGTQTYICNVNHKPSNTKVDKKVEPKSCDKTHT<br>CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLSCAVKGFYPSDIAVEW<br>ESNGQPENNYKTTPPVLDSDGSFFLVSKLTVDKSRWQQG<br>NVFSCSVMHEALHNHYTQKSLSLSPGK |
| Anti-CD40-LYNV hole HC | SEQ ID NO: 58 | QVQLVQSGAEVKKPGASVKVSCKASGYTFTGYYMHWVRQ<br>APGQGLEWMGWINPDSGGTNYAQKFQGRVTMTRDTSIST<br>AYMELNRLRSDDTAVYYCARDQPAGACTAGACSYFDYWG<br>QGTLVTVSSASTKGPSVFPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKKVEPKSCDKTHT<br>CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLSCAVKGFYPSDIAVEW<br>ESNGQPENNYKTTPPVLDSDGSFFLVSKLTVDKSRWQQG<br>NVFSCSVMHEALHNHYTQKSLSLSPGK |
| Anti-CD40 knob HC | SEQ ID NO: 59 | QVQLVQSGAEVKKPGASVKVSCKASGYTFTGYYMHWVRQ<br>APGQGLEWMGWINPDSGGTNYAQKFQGRVTMTRDTSIST<br>AYMELNRLRSDDTAVYYCARDQPLGYCTNGVCSYFDYWG<br>QGTLVTVSSASTKGPSVFPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKKVEPKSCDKTHT<br>CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLWCLVKGFYPSDIAVEW<br>ESNGQPENNYKTTPPVLDSDGSFFLYSKLTVDKSRWQQG<br>NVFSCSVMHEALHNHYTQKSLSLSPGK |

Example 4.6: Transient Expression of Anti-CD40 MBody Molecules in 293 Cells

As described in Example 1.5, HEK 293 cells were co-transfected with three different HC and LC plasmid combination for transient expression of each anti-CD40 MBody molecule (Table 42).

TABLE 42

Plasmid Combination for Transient Transfection of HEK293 Cells to Express Anti-CD40 MBodies

| MBody | HC plasmid 1 | HC plasmid 2 | LC plasmid |
|---|---|---|---|
| CD40 LYNV HK MBody | Anti-CD40-LYNV hole HC | Anti-CD40 knob HC | Anti-CD40 LC |
| CD40 LYNV KH MBody | Anti-CD40-LYNV knob HC | Anti-CD40-hole HC | Anti-CD40 LC |

The transient expression level of both MBodies in 293 cells was relatively low, with CD40 LYNV HK MBody at 6.3 mg/L and CD40 LYNV KH MBody at 5.0 mg/L (Table 43).

TABLE 43

Expression of CD40 MBodies in 293 Cells

| MBody | Expression Level (µg/ml) |
|---|---|
| CD40 LYNV HK MBody | 6.3 |
| CD40 LYNV KH MBody | 5.0 |

Example 4.6: Antigen Binding of Anti-CD40 MBodies

The binding capability of 21.4.1 MBody was measured by FACS. First, the CD40-overexpressing HEK 293 cells were stained with hIgG1, 2141 or 2141 Mbody at a range of 0.01 µg/ml to 10 µg/ml. Followed by 30 min incubation on ice with an APC-conjugated anti-human Fc antibody. Cells then are washed twice and resuspended in PBS/FBS. Fluorescence was measured using a Becton Dickinson FACSCalibur (Becton Dickinson, San Jose, Calif.).

The binding of proteins were examined by FACS. 2141 antibody and 2141 MBody bind to CD40 at a comparable affinity with an EC50 of 0.24 and 1.0 µg/ml respectively.

Example 4.7: Agonistic Activity of Anti-CD40 MBody Molecule

The agonistic activity of test antibodies was measured by a HEK 293 cell line with engineered NFκB-SEAP reporter gene driven by overexpressed CD40 at cell surface. The cells were stimulated overnight with hIgG1 control, 2141 antibody or 2141 MBody at a range of 0.01 µg/ml to 10 µg/ml. Then add 200 ul of Quanti-blue to detect NFκB-SEAP activity.

2141 antibody had shown strong agonist activity with an EC50 of 0.12 µg/ml, whereas agonist activity with 2141 Mbody had been mostly abolished (no agonist activity seen up to 1 µg/ml). This suggested that monovalent CD40-binding did not induce the CD40 agonistic activity.

Example 5: Generation of Fab-Body Capable of Monolvalently Binding cMet

Cell surface receptor c-Met is a well validated oncology target (Danilkovitch-Miagkova A et al. J Clin Invest. 2002, 109:863-867. Birchmeier C B W et al. Nat Rev Mol Cell Biol. 2003, 4:915-925. Oyewale A et al. Reviews on Recent Clinical Trials. 2007 2: 143-147. Liu X et al. Expert Opin Invest Drugs 2008.17: 997-1011), it is activated upon dimerization induced by hepatocyte growth factor (HGF) binding. Antibodies developed against c-Met, such as 5D5 reported by Genentech, often result in agonistic effect rather than the desired antagonistic effect, probably because of the bivalent property of the normal form of antibodies (Prat M et al. J Cell Sci. 1998, 111: 237-247. Ohashi K et al. Nature Med. 2000, 6: 327-331). Because of the monovalent binding properties of Fab-body, anti-cMet Fab-body is used to inhibit the proliferation of c-Met expressing tumor cell lines.

Example 5.1: Cloning and Construction of Anti-cMet h5D5 Fab-Body Expression Plasmids The amino acid sequences of variable domains of the parent humanized cMet antibody, designated as h5D5, were extracted from literature (US2007/0092520) (Table 44). An open reading frame (ORF) encoding a polypeptide comprising a signal peptide (Seq ID No. 60), h5D5 light chain (VL+CL) (Seq ID No 61.+Seq ID No. 62), a short linker (Seq ID No. 63) and Fc region (Fcknob, Seq ID No. 64), designated as LFc chain, was cloned into expression vector pHybE (Abbott). Similarly, another ORF encoding a polypeptide comprising a signal peptide (Seq ID No. 65), h5D5 heavy chain Fab region (VH+CH1) (Seq ID No. 66+Seq ID No. 67), a short linker (Seq ID No. 68) and Fc region (Hchole, Seq ID No. 69), designated as HFc chain, was cloned into the expression vector pHybE.

TABLE 44

Amino acid sequences of h5D5 Fab-body

| Protein Region | Sequence Identifier | Amino Acid Sequence 12345678901234567890 |
|---|---|---|
| SIGNAL PEPTIDE | SEQ ID NO.: 60 | MDMRVPAQLLGLLLLWFPGSRC |
| H5D5.VL | SEQ ID NO.: 61 | DIQMTQSPSSLSASVGDRVTITCKSSQSLLYTSSQKN YLAWYQQKPGKAPKLLIYWASTRESGVPSRFSGSGSG TDFTLTISSLQPEDFATYYCQQYYAYPWTFGQGTKVE IKR |
| CL | SEQ ID NO.: 62 | TVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC |
| LINKER | SEQ ID NO.: 63 | GGSGG |
| FCknob | SEQ ID NO.: 64 | CPPCPAPELLGGPSVFLFPPKPKDTLMISRTPEVTCV VVDVSHEDPEVKFNWYVDGVEVHNAKTKPREEQYNST YRVVSVLTVLHQDWLNGKEYKCKVSNKALPAPIEKTI SKAKGQPREPQVYTLPPSREEMTKNQVSLWCLVKGFY PSDIAVEWESNGQPENNYKTTPPVLDSDGSFFLYSKL TVDKSRWQQGNVFSCSVMHEALHNHYTQKSLSLSPGK |
| SIGNAL PEPTIDE | SEQ ID NO.: 65 | MEFGLSWLFLVAILKGVQC |
| H5D5.VH | SEQ ID NO.: 66 | EVQLVESGGGLVQPGGSLRLSCAASGYTFTSYWLHWV RQAPGKGLEWVGMIDPSNSDTRFNPNFKDRFTISADT SKNTAYLQMNSLRAEDTAVYYCATYRSYVTPLDYWGQ GTLVTVSS |
| CH1 | SEQ ID NO.: 67 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| LINKER | SEQ ID NO.: 68 | DKTHT |
| FChole | SEQ ID NO.: 69 | CPPCPAPELLGGPSVFLFPPKPKDTLMISRTPEVTCV VVDVSHEDPEVKFNWYVDGVEVHNAKTKPREEQYNST YRVVSVLTVLHQDWLNGKEYKCKVSNKALPAPIEKTI SKAKGQPREPQVYTLPPSREEMTKNQVSLSCAVKGFY PSDIAVEWESNGQPENNYKTTPPVLDSDGSFFLVSKL TVDKSRWQQGNVFSCSVMHEALHNHYTQKSLSLSPGK |

Example 5.2: Expression of Anti-cMet 115D5 Fab-Body

The anti-cMet h5D5 Fab-body was expressed by transiently transfecting HEK293-6E (human embryonic kidney) cells simultaneously with expression plasmids encoding LFc and HFc chains. Briefly, HEK293-6E cells were cultured at $0.75 \times 10^5$ cells/mL in Freestyle 293 expression medium (Invitrogen) and grown at 5% CO2 and 37° C. The next day the cell density was adjusted at $1.2 \times 10^6$ cells/mL before transfection. For transfection, 1 mg of DNA was diluted into 35 mL of Opti-MEM (Invitrogen) in a flask and 2 ml of PEI (Polysciences, cat #23966) at a concentration of 1 mg/ml into 35 ml of Opti-MEM in another flask. After 5 min incubation at room temperature, DNA and PEI were mixed together and incubated at room temperature for 15 minutes. DNA:PEI complex was then added into the 1 L culture. Next day, Tryptone N1 (cat#19554, Oraganotechnie) was added to final concentration of 0.5%. Cell culture supernatants were harvested 7 days post transfection.

Example 5.3: Purification of Anti-cMet h5D5 Fab-Body

The cell culture supernatants were filtered through a 0.2 mm filter. The filter supernatants were applied to HiTRAP rProtein A FF column (Amersham). The protein was eluted with buffer containing 100 mM Glycine pH 2.7 and 150 mM NaCl, and neutralized with 1 M Tris pH 8.0 buffer. The protein was dialysised against PBS, and further purified with Superdex 5200 size exclusion chromatography (Amersham). In the protein A affinity purification step, a gentle elution method with gentle Ag/Ab binding buffer and gentle Ag/Ab elution buffer (Thermo Scientific, cat#21012 and 21013) was used to increase the final monomer yield.

Example 5.4: Generation of Reference Molecules

Anti-human c-Met antibody 5D5 and antibody fragment 5D5 Fab were produced from hybridoma cell line 5D5 (ATCC). Control human IgG were purchased from Sigma (14506).

A monovalent c-Met antibody, designated as MetMAb1, with identical c-Met binding variable domains (US2007/0092520) was expressed in HEK393-6E cells and purified similarly with the method for anti-cMet h5D5 Fab-body.

Example 5.5: Binding Analysis of Anti-cMet H5D5 Fab-Body by ELISA cMet binding ELISA was performed according to the method described in Example 1.3. The data showed that the antigen binding capability of h5D5 Fab-body was comparable to c-Met monovalent binding molecule MetMAb1 and cMet antibody MAb X (Abbott), and with less than half capacity compared with bivalent antibody 5D5.

Example 5.6: Biochemical Characterization of Anti-cMet H5D5 Fab-Body

The purified anti-cMet h5D5 Fab-body was analyzed with SDS-PAGE under non-reducing and reducing conditions. The protein showed one band around 50 kDa under reducing condition and around 98 kDa under non-reducing condition. Because the molecular weight of the two polypeptide chains of the Fab-body is very close to each other, it cannot be distinguished with SDS-PAGE under reducing condition. The result of non-reducing gel indicates that the two polypeptide chains are efficiently paired.

Mass spectrometry analyses were performed on anti-cMet h5D5 Fab-body under both non-reducing and reducing conditions using method described in Example 1.7. The experimentally determined molecular mass of anti-cMet h5D5 Fab-body and its polypeptide chains was 101,516 (0G0K, non-reducing), 51,029 (0G0K, reducing) and 50,488 Da (0G0K, reducing), which agrees with the theoretical molecular weight of h5D5 Fab-body and its LFc and HFc chains respectively.

SEC analysis on anti-cMet h5D5 Fab-body was performed with the method described in Example 1.6. Anti-cMet h5D5 Fab-body has an apparent molecular weight ~100 KDa with 97% monomer, which agrees with its theoretical molecular weight.

Example 5.7: Phospho-cMet (p-CMet) and Cell Proliferation Assay

The tumor cell line A549 (ATCC #CCL-185) was maintained in DMEM (Gibco-Invitrogen cat. No. 11995) supplemented with 10% fetal bovine serum (FBS) (HyClone SH30070.03). IM-95 (JCRB #1075) was also maintained in DMEM, 10% FBS with 10 mg/L Insulin. SNU-5 (ATCC #CRL-5973) and SNU-620 (KCLB #00620) were cultured in RPMI-1640 (Gibco-Invitrogen, cat. No. 11875) supplemented with 10% FBS.

A549 cells were plated at 40,000 per well in 96-well plate in growth media. Twenty four hours later, cells were pretreated with antibodies for one hour at 37° C., and then stimulated with HGF for 10 minutes at 37° C. Media were then removed and cells lysed with 100 µL/well of Cell Lysis Buffer (Cell Signaling Technology #9803) supplemented with protease inhibitor tablet (Roche #11714900). ELISA capture plates were generated by pre-coating wells with 100 µL of an anti c Met antibody (R&D systems, #MAB3581) at 2 µg/mL) at 4° C. overnight, followed by blocking with 200 µL/well PBS/1% BSA treatment for one hour at room temperature, and washed three times in PBST. Cell lysates (80 µL/well) were added to capture plates and incubated at 4° C. overnight. Plates were washed three times in PBST, and incubated with anti-phospho-tyrosine 4G10-HRP conjugate (Millipore #16-105; 1:1000 diluted in PBST+1% BSA) for two hours at room temperature. Plates were washed three times in PBST and 100 µL of TMB was added to each well and incubated at room temperature until color developed. Reactions were stopped by addition of 100 µL/well 2N sulfuric acid, and the OD was read at 450 nm. The cells were cultured at 37° C. with 5% CO2. The purified anti-cMet h5D5 Fab-body was analyzed with SDS-PAGE under non-reducing and reducing conditions. The protein showed one band around 50 kDa under reducing condition and around 98 kDa under non-reducing condition.

IM-95 cells were plated in 96-well plate (Falcon 35-3075) in 180 µL growth media at 5,000 cells/well. The cells were incubated overnight at 37° C. with 5% CO2. On Day 2, antibody dilutions were added to the cell plate (20 µL/well). Untreated control wells (for 0% control) and wells treated with 10 µM staurosporin (for 100% kill) were included in each plate. The plates were incubated for five days at 37° C. with 5% CO2. On Day 7 (five days after treatment), media was removed and 1× Cell Titer Aqueous One Solution (Promega, G3581) diluted in Opti-mem media (Invitrogen #31985-070) was added to plates and the plates were then incubated for one hour at 37° C. The OD at 490 nm was read on a M5 Spectramax plate reader (Molecular Probes). Percent inhibition was calculated based on 100% kill and untreated control wells using the following formula:

100×(0% control−treated)/(0% control−100% kill).

SNU-5 or SNU-620 cells were plated in 96-well plate in 180 μL serum-free medium (RPMI1640+0.1% BSA) at 10,000 cells/well and incubated overnight at 37° C. with 5% CO2. The same protocol as above was used for treatment and data processing except cells were incubated with treatment for three days, and on Day 5, 40 μL of Cell Titer Aqueous One Solution (Promega, G3581) was added to each well and the plates were then incubated for one hour at 37° C.

Anti-cMet h5D5 Fab-body showed an inhibition potency comparable to anti-cMet monovalent binding molecules 5D5 Fab, MetMAb1 in A549, IM95, and less than half potency to anti-cMet bivalent binding molecules 5D5 and MAb X. Only h5D5 Fab-body and MAb-X inhibited cell proliferation in SNU-5 cells. Bivalent antibody 5D5 stimulated SNU-620 growth while h5D5 Fab-body did not (Table 45). In some cases, the unique antagonist property of h5D5 Fab-body is preferred in therapeutic composition, such as inhibiting a variety cancer cell line without agonistic effect.

TABLE 45

Summary of assays results of anti-cMet h5D5 Fab-body and related molecules

| Proteins | c-Met binding ELISA EC50 (nM) | Inhibition of HGF-induced phospho-c-Met IC50 (nM) | Inhibition of IM-95 proliferation (HGF-dependent) IC50 (nM) | Inhibition of SNU-5 proliferation (constitutively active c-Met) IC50 (nM) | Inhibition/induction of SNU-620 proliferation (constitutively active c-Met but still HGF-inducible) IC50 (nM) |
|---|---|---|---|---|---|
| 5D5 | 0.08 | 1.4 | 5.8 | >600 | stimulatory |
| 5D5Fab | N.D. | 5.9 | 55.7 | >600 | >600 |
| MetMAb1 | 0.27 | 3.8 | 17.4 | >600 | >600 |
| h5D5 Fab-body | 0.24 | 2.6 | 12.8 | 4.1 (max 40%) | >600 |
| MAb X | 0.27 | 0.6 | 0.7 | 0.35 (max 90%) | 0.23 |

Example 5.8: FcRn Binding Analysis

The FcRn binding analysis was performed with anti-cMet h5D5 Fab-body along with a human IgG1 antibody against cMET (Abbott). Anti-cMet h5D5 Fab-body has binding affinity to FcRn that is comparable to that of the Abbott antibody, with EC50 value at 58, 19 and 169 nM respectively, which suggests that their FcRn mediated clearance is comparable.

Example 5.9: Pharmacokinetics

Pharmacokinetic properties of anti-cMet h5D5 Fab-body was determined in CD-1 mice. Male mice were dosed intravenously with a single dose of 5 mg/kg of test Fab-body molecule. Blood samples were collected at various time points. The serum samples were analyzed on a MSD Sector Imager 6000 (Meso Scale Discovery, Gaithersburg, Md.) in a chemiluminescent MSD method using biotinylated c-Met for capture and sulfo-TAG anti-human Ig Kappa for detection. Standard curve fitting and data evaluation was performed using XLfit4 software. A calibration curve was plotted from MSD chemiluminescence units versus theoretical standard concentrations. A four-parameter logistic model was used for curve fitting. The regression equation for the calibration curve was then used to back calculate the measured concentrations. The linear range was 0.005-20 μg/mL and the lower limit of quantitation (LLOQ) was 0.005 μg/mL. Pharmacokinetic parameters were calculated with PLASMA TemplateMaker rev 2.6.12 by non-compartmental analysis and linear trapezoidal method. Anti-cMet h5D5 Fab-body had an average half life 266 hours and clearance rate at 0.46 mg/hr/kg.

Example 6: Generation of Fab-Body Capable of Monovalently Binding CD40

CD40 is a member of the tumor necrosis factor receptor (TNFR) superfamily. CD40 is expressed on the surface of antigen presenting cells, including dendritic cells, B cells and macrophages, humoral and immune mediated responses require the interaction of the CD40 with its ligand, CD40L (CD154) (Grewal is et al. Ann Rev. Immunol., 1996, 16: 111-135). The CD40L-CD40 signaling seems to be involved in the experimentally induced autoimmune diseases such as collagen-induced arthritis, lupus nephritis, acute or chronic graft-versus-host disease, multiple sclerosis and thyroiditis (Mach F et al. Nature 1998, 394: 200-203. Biancone L. Int J Mol Med. 1999, 3:343-353). CD40 is also expressed in a wide range of tumor cells and CD40 antibodies has been implicated to treat cancers (Turner J G et al. J of Immun 2001, 166: 89-94. 57. Luqman M et al. Blood. 2008, 112:711-720. Beatty G L et al. Science 2011, 331:1612-1616). Some of the antibodies are agonists because the cross-linking properties of traditional bivalent antibodies. Fab-body binding to CD40 monovalently can be used to treat cancers and autoimmune diseases by minimizing activation of CD40 signaling.

The amino acid sequences of the CD40 antibody variable domains were extracted from literature (WO2005063289) (Table 46). An open reading frame (ORF) encoding a polypeptide comprising a signal peptide (Seq ID No. 60), anti-CD40 light chain (VL+CL) (Seq ID No. 70+Seq ID No. 62), a short linker (Seq ID No. 63) and Fc region (Fcknob, Seq ID No. 64), designated as LFc chain, is cloned into the expression vector pHybE (Abbott). Similarly, another ORF encoding a polypeptide comprising a signal peptide (Seq ID No. 65), anti-CD40 heavy chain Fab region (VH+CH1) (Seq ID No. 71+Seq ID No. 67), a short linker (Seq ID No. 68) and Fc region (Hchole, Seq ID No. 69), designated as HFc chain, is cloned into the expression vector pHybE. The anti-CD40 Fab-body was expressed and purified in the same process as anti-cMet h5D5 Fab-body in Example 5.

The purified anti-CD40 Fab-body was analyzed with SDS-PAGE under non-reducing and reducing conditions. The protein showed one band around 50 kDa under reducing condition and around 98 kDa under non-reducing condition. Because the molecular weight of the two polypeptide chains of the Fab-body is very close to each other, it cannot be distinguished with SDS-PAGE under reducing condition. The result of non-reducing gel indicates that the two polypeptide chains are efficiently paired.

Mass spectrometry analyses were performed on anti-CD40 Fab-body under both non-reducing and reducing conditions using method described in Example 1.7. The experimentally determined molecular mass of anti-CD40 Fab-body and its polypeptide chains was 101,227 (0G0K, non-reducing), 51,289 (0G0K, reducing) and 49,945 Da (0G0K, reducing), which agrees with the theoretical molecular weight of anti-CD40 Fab-body and its LFc and HFc chains respectively.

SEC analysis on anti-CD40 Fab-body was performed with the method described in Example 1.6. Anti-CD40 Fab-body has an apparent molecular weight ~100 KDa with 98% monomer, which agrees with its theoretical molecular weight.

The antigen binding capacity and agonist activity of anti-CD40 Fab-body were measured in the same way as ant-CD40 Mbody described in Example 4. Parent CD40 antibody and Fab-body bind to CD40 at a comparable affinity with an EC50 of 0.24 and 0.47 µg/ml respectively.

The agonistic activity of test antibodies was measured by a HEK 293 cell line with engineered NFκB-SEAP reporter gene driven by overexpressed CD40 at cell surface as described in Example 4.7. The parental CD40 antibody had shown strong agonist activity with an EC50 of 0.12 µg/ml, whereas agonist activity with Fab-body had been greatly reduced and there was no agonist activity seen up to 0.1 µg/ml.

TABLE 46

Amino acid sequences of anti-CD40 Fab-body

| Protein Region | Sequence Identifier | Amino Acid Sequence 12345678901234567890 |
|---|---|---|
| SIGNAL PEPTIDE | SEQ ID NO.: 60 | MDMRVPAQLLGLLLLWFPGSRC |
| Anti-CD40.VL | SEQ ID NO.: 70 | DIQMTQSPSSVSASVGDRVTITCRASQGIYSWLAWYQQK PGKAPNLLIYTASTLQSGVPSRFSGSGSGTDFTLTISSL QPEDFATYYCQQANIFPLTFGGGTKVEIKR |
| CL | SEQ ID NO.: 62 | TVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC |
| LINKER | SEQ ID NO.: 63 | GGSGG |
| FCknob | SEQ ID NO.: 64 | CPPCPAPELLGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLWCLVKGFYPSDIAVEW ESNGQPENNYKTTPPVLDSDGSFFLYSKLTVDKSRWQQG NVFSCSVMHEALHNHYTQKSLSLSPGK |
| SIGNAL PEPTIDE | SEQ ID NO.: 65 | MEFGLSWLFLVAILKGVQC |
| Anti-CD40.VH | SEQ ID NO.: 71 | QVQLVQSGAEVKKPGASVKVSCKASGYTFTGYYMHWVRQ APGQGLEWMGWINPDSGGTNYAQKFQGRVTMTRDTSIST AYMELNRLRSDDTAVYYCARDQPLGYCTNGVCSYFDYWG QGTLVTVSS |
| CH1 | SEQ ID NO.: 67 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| LINKER | SEQ ID NO.: 68 | DKTHT |
| FChole | SEQ ID NO.: 69 | CPPCPAPELLGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLSCAVKGFYPSDIAVEW ESNGQPENNYKTTPPVLDSDGSFFLVSKLTVDKSRWQQG NVFSCSVMHEALHNHYTQKSLSLSPGK |

Example 7: Generation of Fab-Body Capable of Monolvalently Binding CD3 and HER2Respectively and Simultaneously Similar to the rationale stated in Example 3, Fab-body binding CD3 and HER2 has application in killing HER2 positive cancer cells and tumor treatment.

The amino acid sequences of DVD-Ig molecule variable domains binding CD3 and HER2 were extracted from molecule DVD012 (Abbott) (Table 47). An open reading frame (ORF) encoding a polypeptide comprising a signal peptide (Seq ID No. 60), DVD-Ig light chain (VL+CL) (Seq ID No. 72+Seq ID No. 62), a short linker (Seq ID No. 63) and Fc region (Fcknob, Seq ID No. 64), designated as LFc chain, is cloned into expression vector pHybE (Abbott). Similarly, another ORF encoding a polypeptide comprising a signal peptide (Seq ID No. 65), DVD-Ig heavy chain Fab region (VH+CH1) (Seq ID No. 73+Seq ID No. 67), a short linker (Seq ID No. 68) and Fc region (Hchole, Seq ID No. 69), designated as HFc chain, is cloned into the expression vector pHybE. The Fab-body monovalently binding CD3 and HER2 is expressed, purified and biochemically in the same process as anti-cMet h5D5 Fab-body in Example 5.

The purified DVD012 Fab-body was analyzed with SDS-PAGE under non-reducing and reducing conditions. The protein showed one band around 60 kDa under reducing condition and around 120 kDa under non-reducing condition. Because the molecular weight of the two polypeptide chains of the Fab-body is very close to each other, it cannot be distinguished with SDS-PAGE under reducing condition. The result of non-reducing gel indicates that the two polypeptide chains are efficiently paired.

Mass spectrometry analyses were performed on DVD012 Fab-body under both non-reducing and reducing conditions using method described in Example 1.7. The experimentally determined molecular mass of The mass spectrometry of DVD012 Fab-body at reducing condition clearly indicated two polypeptides with one chain molecular weights 64,485 and 64,647 Da, which agrees with the theoretical molecular weight of HFc G0K0 and G1K0 glycosylation stage, and the second chain at with molecular weight clustered around 63,861 and 64,023 Da, which may reflect that LFc is heavily glycosylated. The non-reducing condition gave molecular weights 128,338, 128,503 and 128,664 Da, which reflects the sum of the LFc and HFc chains.

SEC analysis on DVD012 Fab-body was performed with the method described in Example 1.6. DVD012 Fab-body has an apparent molecular weight ~160 KDa, which is common to a lot of Fc fusion proteins with molecular weight smaller than 150 KDa. The purified DVD012 Fab-body has more than 98% monomer.

TABLE 47

Amino acid sequences of DVD012 Fab-body

| Protein Region | Sequence Identifier | Amino Acid Sequence 12345678901234567890 |
|---|---|---|
| SIGNAL PEPTIDE | SEQ ID NO.: 60 | MDMRVPAQLLGLLLLWFPGSRC |
| DVD012.VL | SEQ ID NO.: 72 | DIQMTQSPSSLSASVGDRVTITCRASQDVNTAVAWYQ QKPGKAPKLLIYSASFLYSGVPSRFSGSRSGTDFTLT ISSLQPEDFATYYCQQHYTTPPTFGQGTKVEIKRTVA APQIVLTQSPAIMSASPGEKVTMTCRASSSVSYMNWY QQKSGTSPKRWIYDTSKVASGVPYRFSGSGSGTSYSL TISSMEAEDAATYYCQQWSSNPLTFGSGTKLEINR |
| CL | SEQ ID NO.: 62 | TVAAPSVFIFPPSDEQLKSGTASVVCLLNNFYPREAK VQWKVDNALQSGNSQESVTEQDSKDSTYSLSSTLTLS KADYEKHKVYACEVTHQGLSSPVTKSFNRGEC |
| LINKER | SEQ ID NO.: 63 | GGSGG |
| FCknob | SEQ ID NO.: 64 | CPPCPAPELLGGPSVFLFPPKPKDTLMISRTPEVTCV VVDVSHEDPEVKFNWYVDGVEVHNAKTKPREEQYNST YRVVSVLTVLHQDWLNGKEYKCKVSNKALPAPIEKTI SKAKGQPREPQVYTLPPSREEMTKNQVSLWCLVKGFY PSDIAVEWESNGQPENNYKTTPPVLDSDGSFFLYSKL TVDKSRWQQGNVFSCSVMHEALHNHYTQKSLSLSPGK |
| SIGNAL PEPTIDE | SEQ ID NO.: 65 | MEFGLSWLFLVAILKGVQC |
| DVD012.VH | SEQ ID NO.: 73 | EVQLVESGGGLVQPGGSLRLSCAASGFNIKDTYIHWV RQAPGKGLEWVARIYPTNGYTRYADSVKGRFTISADT SKNTAYLQMNSLRAEDTAVYYCSRWGGDGFYAMDYWG QGTLVTVSSASTKGPQVQLQQSGAELARPGASVKMSC KASGYTFTRYTMHWVKQRPGQGLEWIGYINPSRGYTN YNQKFKDKATLTTDKSSTAYMQLSSLTSEDSAVYYC ARYYDDHYCLDYWGQGTTLTVSS |
| CH1 | SEQ ID NO.: 67 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC |
| LINKER | SEQ ID NO.: 68 | DKTHT |

TABLE 47-continued

Amino acid sequences of DVD012 Fab-body

| Protein Region | Sequence Identifier | Amino Acid Sequence 12345678901234567890 |
|---|---|---|
| FChole | SEQ ID NO.: 69 | CPPCPAPELLGGPSVFLFPPKPKDTLMISRTPEVTCV VVDVSHEDPEVKFNWYVDGVEVHNAKTKPREEQYNST YRVVSVLTVLHQDWLNGKEYKCKVSNKALPAPIEKTI SKAKGQPREPQVYTLPPSREEMTKNQVSLSCAVKGFY PSDIAVEWESNGQPENNYKTTPPVLDSDGSFFLVSKL TVDKSRWQQGNVFSCSVMHEALHNHYTQKSLSLSPGK |

The antigen-binding capability of DVD012 Fab-body was assessed by a FACS assays. $0.5 \times 10^6$ of Jurkat or NCI-N87 cells were washed with FACS buffer (1% BSA/PBS) and resuspended in 50 ul of FACS buffer. mAbs or Fab-bodies were prepared in 50 ul of FACS buffer and mixed with cells and incubated at 4° C. for 1 hr. Cells were washed with FACS buffer and resuspended in 50 ul of FACS buffer containing Alexa Fluo 488-F(ab')2 fragment goat anti-human IgG, Fcgamma (Jackson Labs) and incubated at 4° C. for 1 hr. and then cells were washed with FACS buffer and analyzed in FACS canto II instrument (BD Biosciences). The EC50 for CD3 binding was 89 and 95 nM respectively for parental DVD-Ig and Fab-body respectively. The EC50 for HER2 binding was 7 and 12 nM respectively.

Redirected Cytotoxicity (rCTL) Assays were performed with DVD012 Fab-body against HER2 expression tumor cell line. NCI-N87 cells (T) were plated at $2 \times 10^4$ cells/well and allowed to adhere to ACEA RT-CES 96-well plates (ACEA Bio, San Diego) overnight. Effector PBMC cells (E) were then plated at $1 \times 10^6$ cells/well to give an E:T ratio of 50:1. DVD-Ig or FabBody molecules were appropriately diluted to obtain concentration-dependent titration curves. The cell indexes of targets in the DVD-Ig treated samples were divided by the cell indexes of control targets (no treatment) to calculate percent specific lysis. The data was graphed and IC50 s were calculated in Prism (Graphpad).

Both the parental DVD-Ig and Fab-body induced effective killing with EC50 at 0.51 and 0.29 nM respectively.

Example 8: Generation of Fab-Body Capable of Monolvalently Binding CD3 and EGFR Respectively and Simultaneously As stated in Example 3, Fab-body binding CD3 and EGFR has application in killing cancer cells and in tumor treatment.

The amino acid sequences of DVD-Ig molecule variable domains binding CD3 and EGFR were extracted from molecule DB001 (Abbott) (Table 48). An open reading frame (ORF) encoding a polypeptide comprising a signal peptide (Seq ID No. 60), DVD-Ig light chain (VL+CL) (Seq ID No. 74+Seq ID No. 62), a short linker (Seq ID No. 63) and Fc region (Fcknob, Seq ID No. 64), designated as LFc chain, is cloned into expression vector pHybE (Abbott). Similarly, another ORF encoding a polypeptide comprising a signal peptide (Seq ID No. 65), DVD-Ig heavy chain Fab region (VH+CH1) (Seq ID No. 75+Seq ID No. 67), a short linker (Seq ID No. 68) and Fc region (Hchole, Seq ID No. 69), designated as HFc chain, is cloned into the expression vector pHybE. The Fab-body monolvalently binding to CD3 and EGFR was expressed, purified and biochemically characterized in the same process as anti-cMet 5D5 Fab-body in Example 5.

TABLE 48

Amino acid sequences of DB001 Fab-body

| Protein Region | Sequence Identifier | Amino Acid Sequence 12345678901234567890 |
|---|---|---|
| SIGNAL PEPTIDE | SEQ ID NO.: 60 | MDMRVPAQLLGLLLLWFPGSRC |
| DB001.VL | SEQ ID NO.: 74 | DIQMTQSPSSMSVSVGDRVTITCHSSQDINSNIGWLQQK PGKSFKGLIYHGTNLDDGVPSRFSGSGSGTDYTLTISSL QPEDFATYYCVQYAQFPWTFGGGTKLEIKTVAAPSVFIF PPDAQVTQSPSSLSASVGDRVTITCRSSTGAVTTSNYAN WVQEKPGKLFKGLIGGTNKRAPGVPSRFSGSGSGTDATL TISSLQPEDFATYFCALWYSNLWVFGGGTKVEIKR |
| CL | SEQ ID NO.: 62 | TVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC |
| LINKER | SEQ ID NO.: 63 | GGSGG |
| FCknob | SEQ ID NO.: 64 | CPPCPAPELLGGPSVFLFPPKPKDTLMISRTPEVTCVVV DVSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLWCLVKGFYPSDIAVEW ESNGQPENNYKTTPPVLDSDGSFFLYSKLTVDKSRWQQG NVFSCSVMHEALHNHYTQKSLSLSPGK |

TABLE 48-continued

Amino acid sequences of DB001 Fab-body

| Protein Region | Sequence Identifier | Amino Acid Sequence<br>12345678901234567890 |
|---|---|---|
| SIGNAL PEPTIDE | SEQ ID NO.: 65 | MEFGLSWLFLVAILKGVQC |
| DB001.VH | SEQ ID NO.: 75 | QVQLQESGPGLVKPSQTLSLTCTVSGYSISSDFAWNWIR<br>QPPGKGLEWMGYISYSGNTRYQPSLKSRITISRDTSKNQ<br>FFLKLNSVTAADTATYYCVTAGRGFPYWGQGTLVTVSSA<br>STKGPEVQLVESGGGLVQPGGSLRLSCAASGFTFSTYAM<br>NWVRQAPGKGLEWVGRIRSKYNNYATYYADSVKDRFTIS<br>RDDSKNTAYLQMNSLRAEDTAVYYCTRHGNFGNSYVSWF<br>AYWGQGTLVTVSS |
| CH1 | SEQ ID NO.: 67 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSC |
| LINKER | SEQ ID NO.: 68 | DKTHT |
| FChole | SEQ ID NO.: 69 | CPPCPAPELLGGPSVFLFPPKPKDTLMISRTPEVTCVVV<br>DVSHEDPEVKFNWYVDGVEVHNAKTKPREEQYNSTYRVV<br>SVLTVLHQDWLNGKEYKCKVSNKALPAPIEKTISKAKGQ<br>PREPQVYTLPPSREEMTKNQVSLSCAVKGFYPSDIAVEW<br>ESNGQPENNYKTTPPVLDSDGSFFLVSKLTVDKSRWQQG<br>NVFSCSVMHEALHNHYTQKSLSLSPGK |

The purified DB001 Fab-body was analyzed with SDS-PAGE under non-reducing and reducing conditions. The protein showed one band around 60 kDa under reducing condition and around 120 kDa under non-reducing condition. Because the molecular weight of the two polypeptide chains of the Fab-body is very close to each other, it cannot be distinguished with SDS-PAGE under reducing condition. The result of non-reducing gel indicates that the two polypeptide chains are efficiently paired.

Mass spectrometry analyses were performed on DB001 Fab-body under both non-reducing and reducing conditions using method described in Example 1.7. The experimentally determined molecular mass of The mass spectrometry of DB001 Fab-body at reducing condition clearly indicated two polypeptides with one chain molecular weights 64,530 and 64,692 Da, which agrees with the theoretical molecular weight of HFc G0K0 and G1K0 glycosylation stages, and the second chain at with molecular weight clustered around 62,881 and 63,043 Da, which agrees with the theoretical molecular weight of LFc G0K0 and G1K0 glycosylation stages. The non-reducing condition gave molecular weights 127,405, 127,567 and 127,729 Da, which reflects the sum of the LFc and HFc chains.

Similarly to DVD012 Fab-body described in Example 7. SEC analysis on DB001 Fab-body was performed with the method described in Example 1.6. DB001 Fab-body also has an apparent molecular weight ~160 KDa, which is common to a lot of Fc fusion proteins with their molecular weight smaller than 150 KDa. The purified DB001 Fab-body has more than 98% monomer.

The antigen-binding capability of DB001 Fab-body was assessed by a FACS assays. 0.5×106 of Jurkat or U87MG.de2-7 cells were washed with FACS buffer (1% BSA/PBS) and resuspended in 50 ul of FACS buffer. mAbs or Fab-bodies were prepared in 50 ul of FACS buffer and mixed with cells and incubated at 4° C. for 1 hr. Cells were washed with FACS buffer and resuspended in 50 ul of FACS buffer containing Alexa Fluo 488-F(ab')2 fragment goat anti-human IgG, Fcgamma (Jackson Labs) and incubated at 4° C. for 1 hr. and then cells were washed with FACS buffer and analyzed in FACS canto II instrument (BD Biosciences). The EC50 for CD3 binding was 74 and 80 nM respectively for parental DVD-Ig and Fab-body respectively. The EC50 for EGFR binding was 9 and 15 nM respectively.

Redirected Cytotoxicity (rCTL) Assays were performed with DB001Fab-body against EGFR expression tumor cell line as described in Example 3.5. Compared to the parental anti-CD3/EGFR DVD-Ig molecule DB021 with an EC50 at 1.5 nM, DB001 Fab-body maintained the rCTL with a relatively larger EC50 at 5.8 nM.

Example 9: Construction and Characterization of Various Half-Igs and their Parental Antibodies FIG. 3 provides a schematic representation of various formats of antibodies and immunoglobulin based divalent molecules (top row) that can be used as the basis to design half-Ig binding proteins (bottom row). As shown in the various half-Ig binding protein formats, the heavy chain antigen binding domain containing peptide is paired with a light chain antigen binding domain containing peptide. In the schematic of the half-Ig binding protein, half-DVD binding protein, and half-TVD binding protein, the light and heavy chain variable domains are shown as a complementary pair forming a single antigen binding domain. In the half-RAb-Ig binding protein, the variable domains adjacent to the constant regions are shown as a complementary pair, and the receptors in each of the light chain antigen binding domain containing peptide and the heavy chain antigen binding domain containing peptide do not interact and form independent binding sites. These half-Ig (also termed Half-Body or half-body) are described in details in U.S. patent application Ser. No. 13/333,545, which is hereby incorporated by reference into the present application.

Anti-cMet 1/21 g (half-Ig) was generated according to U.S. patent application Ser. No. 13/333,545. Diagram of the anti-cMet half-Ig is as shown in the left panel of FIG. 4. HGF induced C-Met phosphorylation was measured as described in Example 4 above. As shown in the chart in FIG. 4, anti-cMet half-Ig functions as an antagonist to HGF induced cMet phosphorylation, whereas the regular c-Met mAb functions as a agonist to HGF induced cMet phosphorylation.

The antibodies shown in FIG. 3 may have drastically different properties as compared to the parental antibodies. For instance, the orientation or order of the variable domains and the valency of the antibody both play a significant role in determining the functionality of the modified antibodies. FIG. 5 shows a number of DVD Igs having variable domains from the anti-HER2 antibodies Trastuzumab and Pertuzumab, respectively. As shown in the left panel, reversing the order of the variable domains of the DVD Ig changes the functionality of the DVD-Igs from a HER2 agonist to a HER2 antagonist. The valency of the antibody also affects its functionality. As shown in FIG. 5 right panel, a half-Ig (Half DVD687) created based on the DVD-Ig 687 does not show the agonistic effect exhibited by the parental antibody DVD-Ig 687.

Example 10: Other Antibody Formats Generated by Adjusting Valency and/or Specificity FIG. 6 shows various modified antibody formats that are generated by the various techniques described herein. These techniques include, for example, inactivation of a binding domain by point mutations or deletion mutations, addition of binding domains by addition of extra variable domains or receptor domains. The Fc engineering described in Example 1 may also be used.

The following items are also disclosed as additional embodiments of the inventions:

1. An immunoglobulin wherein complementarity determining region (CDR) 3 of one heavy chain variable domain comprises at least one mutation to inhibit the binding between antigen and the mutant binding arm.

2. The immunoglobulin of Item 1, wherein CDR of one heavy chain variable domain comprises at least one mutation to inhibit the binding between antigen and the mutant binding arm.

3. The immunoglobulin of Item 1, wherein one heavy chain variable domain comprises at least one mutation to inhibit the binding between antigen and the mutant binding arm.

4. The immunoglobulin of Item 1, wherein one variable domain or one binding arm comprises at least one mutation to inhibit the binding between antigen and the mutant binding arm.

5. A dual-variable-domain immunoglobulin (DVD-Ig) or multi-variable-domain Ig wherein CDR3 of at least one heavy chain variable domain comprises at least one mutation to inhibit the targeted binding between the specific antigen and the mutant binding domain.

6. The DVD-Ig or multi-variable-domain Ig of Item 5, wherein CDR of at least one heavy chain variable domain comprises at least one mutation to inhibit the targeted binding between the specific antigen and the mutant binding domain.

7. The DVD-Ig or multi-variable-domain Ig of Item 5, wherein at least one heavy chain variable domain comprises at least one mutation to inhibit the targeted binding between the specific antigen and the mutant binding domain.

8. The DVD-Ig or multi-variable-domain Ig of Item 5, wherein at least one variable domain comprises at least one mutation to inhibit the targeted binding between the specific antigen and the mutant binding domain.

9. A binding protein wherein the protein comprises a polypeptide $(VD)_N$-X-Y and a companion polypeptide $(VD')_N$-X', wherein:

VD comprises a variable domain;

VD' comprises a variable domain, paring to VD;

X comprises a $C_{kappa}$ or $C_{lambda}$ or CH1.

X' comprises a CH1 or $C_{kappa}$ or $C_{lambda}$, pairing to X

Y comprises a CH2-CH3 or CH3 or part of CH3.

N is an positive integer; and wherein complementarity determining region (CDR) 3 of at least one VD and/or VD' comprises at least one mutation to inhibit the binding between antigen and the mutant binding domain.

10. The binding protein of Item 9, wherein CDR of at least one VD and/or VD' comprises at least one mutation to inhibit the binding between antigen and the mutant binding domain.

11. The binding protein of Item 9, wherein at least one VD and/or VD' comprises at least one mutation to inhibit the binding between antigen and the mutant binding domain.

12. The binding protein of any one of Item 1, 5, 9, wherein the mutation combination in antigen binding domain can be acquired by random-mutagenesis library approach and screened by a functional assay, or can be acquired by crystallization or molecular modeling-guided approach.

13. A form of therapeutic molecule Fab-body comprises a single antigen binding arm and a Fc region, which increases the stability of Fab-body compared with its Fab fragment and bind to antigen in the similar way as Fab fragment.

14. The Fab-body molecule in Item 13 is designed such that one peptide chain comprise the light chain (VL+CL) from the parent antibody linked directly or via a linker to Fc or Fc region with mutation. Similarly, another chain comprises the heavy chain variable domain (VH) and constant domain (CH1) from the parent antibody linked directly or via a linker to Fc or Fc region with mutation. The two chains form a heterodimeric molecule which comprises one antigen binding arm of the parent antibody and a functional Fc.

15. The antibody in Item 14 is a monoclonal antibody, a DVD-Ig or a TVD-Ig.

16. The Fab-body in Item 14, the heterodimeric polypeptides interact through a dimerization domain.

17. In Item 16, the dimerization domain is located in the CH3 domain of Fc region or in the heavy chain constant domain (CH1) and light chain constant domain (CL) of the parent antibody.

18. In Item 17, the CH3 domain of Fc region is wild type or is mutated to enhance the heterodimeric formation.

19. In Item 14, the amino acid sequence of linkers are either same as naturally occurring or are theoretically designed.

20. In Item 14, the linker between the light chain and Fc region is same or different from the linker between the heavy chain constant domain (CH1) and Fc region. They are designed in such a way not to abolish antigen binding.

21. In Item 14, 19 and 20, the length of the linker is varied from 0 to 1,000 amino acids.

22. In Item 15, the antibody is a traditionally monoclonal antibody for single epitope binding, or a DVD-Ig for two-epitope binding, or a TVD-Ig for three-epitope binding.

23. A Fab-body conjugate comprising a Fab-body described in any one of Items 13-22 and an agent selected from the group consisting of; an immunoadhesion molecule, an imaging agent, a therapeutic agent, and a cytotoxic agent.

24. The Fab-body conjugate of Item 23, wherein the agent is a therapeutic or cytotoxic agent selected from the group consisting of; an anti-metabolite, an alkylating agent, an antibiotic, a growth factor, a cytokine, an anti-agiogenic agent, an anti-mitotic agent, an anthracycline, toxin, and an apoptotic agent.

25. A pharmaceutical composition comprising a Fab-body of any one of the preceding Items, and a pharmaceutically acceptable carrier.

26. The pharmaceutical composition of Item 25, further comprising at least one additional agent.

27. The pharmaceutical composition of Item 26, wherein the additional agent is selected from the group consisting of a therapeutic agent, an imaging agent, a cytotoxic agent, an angiogenesis inhibitor; a kinase inhibitor; a co-stimulation molecule blocker; an adhesion molecule blocker; an anti-cytokine antibody or functional fragment thereof; methotrexate; cyclosporin; rapamycin; FK506; a detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, 3H, 14C, 35S, 90Y, 99Tc, 111In, 125I, 131I, 177Lu, 166Ho, 153Sm, a fluorescent label, a luminescent label, a bioluminescent label, a magnetic label, biotin, an antidepressant, an antipsychotic, a stimulant, an asthma medication, a beta agonist, an inhaled steroid, an epinephrine or analog, a cytokine, and a cytokine antagonist.

28. A pharmaceutical composition comprising a Fab-body conjugate of Item 25, and a pharmaceutically acceptable carrier.

29. A nucleic acid encoding a polypeptide of any of Items 13 to 22.

30. An expression construct comprising the nucleic acid of Item 29.

31. A host cell transformed or transfected with the expression construct according Items 29 and 30.

32. The host cell according to Item 31, wherein said host cell is a prokaryotic cell.

33. The host cell according to Item 31, wherein said host cell is *E. Coli.*

34. The host cell according to Item 31, wherein said host cell is a eukaryotic cell.

35. The host cell according to Item 34, wherein said eukaryotic cell is selected from the group consisting of protist cell, animal cell, plant cell and fungal cell.

36. The host cell according to Item 34, wherein said eukaryotic cell is an animal cell selected from the group consisting of; a mammalian cell, an avian cell, and an insect cell.

37. The host cell according to Item 34, wherein said host cell is a CHO cell.

38. The host cell according to Item 34, wherein said host cell is a COS cell.

39. The host cell according to Item 34, wherein said host cell is a HEK293 cell.

40. The host cell according to Item 34, wherein said host cell is an NS0 cell.

41. The host cell according to Item 34, wherein said host cell is a yeast cells.

42. The host cell according to Item 35, wherein said yeast cell is *Saccharomyces cerevisiae.*

43. The host cell according to Item 34, wherein said host cell is an insect Sf9 cell.

44. The host cell according to Item 34, wherein said host cell is an insect Sf21 cell.

45. The host cell according to Item 34, wherein said host cell is an insect High-5 cell.

46. The host cell according to Item 34, wherein said host cell is an insect S2 cell.

47. A method of producing an Fab-body, comprising culturing a host cell described in any one of Items 34-34 in culture medium under conditions sufficient to produce the Fab-body.

48. The binding protein of any one of Items 1, 5, 9, 13-22, wherein the conformation-change mutations or charge mutations are introduced for heterodimerization; and the conformation-change and charge mutation combinations include but not limited to:
  v1. Heavy chain 1 (D399C), heavy chain 2 (K392C)
  v2. Heavy chain 1 (T366W), heavy chain 2 (T366S: L368A:Y407V)
  v3. Heavy chain 1 (T366W:D399C), heavy chain 2 (T366S:L368A:K392C:Y407V)
  v4. Heavy chain 1 (T366W:K392C), heavy chain 2 (T366S:L368A:D399C:Y407V)
  v5. Heavy chain 1 (S354C:T366W), heavy chain 2 (Y349C:T366S:L368A:Y407V)
  v6. Heavy chain 1 (Y349C:T366W), heavy chain 2 (S354C:T366S:L368A:Y407V)
  v7. Heavy chain 1 (E356C:T366W), heavy chain 2 (Y349C:T366S:L368A:Y407V)
  v8. Heavy chain 1 (Y349C:T366W), heavy chain 2 (E356C:T366S:L368A:Y407V)
  v9. Heavy chain 1 (E357C:T366W), heavy chain 2 (Y349C:T366S:L368A:Y407V)
  v10. Heavy chain 1 (Y349C:T366W), heavy chain 2 (E357C:T366S:L368A:Y407V)
  v11. Heavy chain 1 (K409D), heavy chain 2 (D339K)
  v12. Heavy chain 1 (K:392D:K409D), heavy chain 2 (D339K:E356K)
  v13. Heavy chain 1 (K:392D:K409D), heavy chain 2 (D399K:D357K)
  v14. Heavy chain 1 (K:370D:K409D), heavy chain 2 (D399K:D357K)
Wherein all numberings are according to kabat scheme.

49. The binding protein of any one of Items 1, 5, 9, 13-22, wherein mutations are introduced to manipulate CH3/CH3 heterodimerization.

50. The binding protein of any one of Items 1 to 22, 48-49, wherein the binding protein forms a functional antigen binding site for an antigen selected from the group consisting of a cell surface-bound molecule, a soluble molecule, a cytokine, a chemokine, an enzyme, a hapten, a lipid, and a receptor.

51. The binding protein of any one of Items 1 to 22, 48-50, wherein the binding protein forms a functional antigen binding site for an antigen selected from the group consisting of c-Met, Muc-1, CD28, CD40, CD19, CD3, TWEAK, TNFR, TREM-1,ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p161NK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10(IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB21P; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); F1112584; F1125530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GF11; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICE-BERG; ICOSL; ID2; IFN-a; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDL-1; MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; SI00A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase ha); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

52. The binding protein of any one of the preceding Items, wherein the binding protein is capable of binding one or more targets.

53. The binding protein of Item 51, wherein the one or more targets is selected from the group consisting of c-Met, CD-28, CD-3, CD-19, ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC- 4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL2? (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10(IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; F1125530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; ID2; IFN-α; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MDL-1; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; SI00A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STATE; STEAP; STEAP2; TB4R2; TBX21; TCP10; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

54. The binding protein of any one of Items 1 to 22, 48-52 wherein the binding protein is capable of binding two targets, wherein the two targets are selected from the group consisting of c-Met and CD-28; c-Met and CD-3; c-Met and CD-19; CD-28 and CD-3; CD-28 and CD-19; CD-3 and CD-19; CD138 and CD20; CD138 and CD40; CD20 and CD3; CD38 & CD138; CD38 and CD20; CD38 and CD40; CD40 and CD20; CD19 and CD20; CD-8 and IL-6; PDL-1 and CTLA-4; CTLA-4 and BTNO2; CSPGs and RGM A; IGF1 and IGF2; IGF1/2 and Erb2B; IL-12 and IL-18; IL-12 and TWEAK; IL-13 and ADAMS; IL-13 and CL25; IL-13 and IL-1beta; IL-13 and IL-25; IL-13 and IL-4; IL-13 and IL-5; IL-13 and IL-9; IL-13 and LHR agonist; IL-13 and MDC; IL-13 and MIF; IL-13 and PED2; IL-13 and SPRR2a; IL-13 and SPRR2b; IL-13 and TARC; IL-13 and TGF-.beta.;

IL-1-α and IL-1β.; MAG and RGM A; NgR and RGM A; NogoA and RGM A; OMGp and RGM A; RGM A and RGM B; Te38 and TNF-α; TNF-α and IL-12; TNF-α and IL-12p40; TNF-α. and IL-13; TNF-α and IL-15; TNF-α. and IL-17; TNF-a and IL-18; TNF-α and IL-1beta; TNF-α and IL-23; TNF-α and MIF; TNF-α and PEG2; TNF-α and PGE4; TNF-α, and VEGF; and VEGFR and EGFR; TNF-α and RANK ligand; TNF-α and Blys; TNF-α, and GP130; TNF-α, and CD-22; and TNFα and CTLA-4.

55. The binding protein of Item 54, wherein the binding protein is capable of modulating a biological function of one or more targets.

56. The binding protein of Item 54, wherein the binding protein is capable of neutralizing one or more targets.

57. The binding protein of any one of Items 1 to 22, 48-56, wherein the linker is selected from the group consisting of ASTKGPSVFPLAP (SEQ ID NO: 76), ASTKGP (SEQ ID NO: 77); TVAAPSVFIFPP (SEQ ID NO: 78); TVAAP (SEQ ID NO: 79); AKTTPKLEEGEFSEAR (SEQ ID NO: U641180); AKTTPKLEEGEFSEARV (SEQ ID NO: 81); AKTTPKLGG (SEQ ID NO: 82); SAKTTPKLGG (SEQ ID NO: 83); SAKTTP (SEQ ID NO: 84); RADAAP (SEQ ID NO: 85); RADAAPTVS (SEQ ID NO: 86); RADAAAGGPGS (SEQ ID NO: 87); RADAAAA (G4S]])4 (SEQ ID NO: 88); SAKTTPKLEEGEFSEARV (SEQ ID NO: 89); ADAAP (SEQ ID NO: 90); ADAAPTVSIFPP (SEQ ID NO: 91); QPKAAP (SEQ ID NO: 92); QPKAAPSVTLFPP (SEQ ID NO: 93); AKTTPP (SEQ ID NO: 94); AKTTPPSVT-PLAP (SEQ ID NO: 95); AKTTAP (SEQ ID NO: 96); AKTTAPSVYPLAP (SEQ ID NO: U811197); GGGGSGGGGSGGGGS (SEQ ID NO: 98); GENKVEYAPALMALS (SEQ ID NO: 99); GPAKELTPLKEAKVS (SEQ ID NO: U8411100); GHEAAAVMQVQYPAS (SEQ ID NO: 101); and TVAAPSVFIFPPTVAAPSVFIFPP (SEQ ID NO: U8611102);

58. The binding protein of any one of Items 1 to 22, 48-57, wherein the binding protein has an on rate constant($K_{on}$) to the one or more targets selected from the group consisting of: at least about $10^2 M^{-1}s^{-1}$; at least about $10^3 M^{-1}s^{-1}$, at least about $10^4 M^{-1}s^{-1}$; at least about $10^5 M^{-1}s^{1}$; and at least about $10^6 M^{-1}s^{-1}$, as measured by surface plasmon resonance.

59. The binding protein of any one of Items 1 to 22, 48-58, wherein the binding protein has an off rate constant($K_{off}$) to the one or more targets selected from the group consisting of: at most about $10^3 M^{-1}s^{-1}$; at most about $10^4 M^{-1}s^{-1}$; at most about $10^5 M^{-1}s^{-1}$; and at most about $10^6 M^{-1}s^{-1}$, as measured by surface plasmon resonance.

60. The binding protein of any one of Items 1 to 22, 48-59, wherein the binding protein has a dissociation constant ($K_D$) to the one or more targets selected from the group consisting of: at most about $10^{-6}$ M; at most about $10^{-7}$ M; at most about $10^{-8}$ M; at most about $10^{-9}$ M; at most about $10^{-10}$ M; at most about $10^{-11}$ M; and at most $10^{-12}$ M.

61. A binding protein conjugate comprising a binding protein described in any one of Items 1 to 22, 48-60, further comprising an agent selected from the group consisting of; an immunoadhesion molecule, an imaging agent, a therapeutic agent, and a cytotoxic agent.

62. The binding protein conjugate of Item 60, wherein the agent is a therapeutic or cytotoxic agent selected from the group consisting of; an anti-metabolite, an alkylating agent, an antibiotic, a growth factor, a cytokine, an anti-angiogenic agent, an anti-mitotic agent, an anthracycline, toxin, and an apoptotic agent.

63. The binding protein of any one of Items 1 to 22, 48-61, wherein the protein is produced according to a method comprising culturing a host cell in culture medium under conditions sufficient to produce the binding protein, wherein the host cell comprises a vector, the vector comprising a nucleic acid encoding the binding protein.

64. A pharmaceutical composition comprising a binding protein of any one of the preceding Items, and a pharmaceutically acceptable carrier.

65. The pharmaceutical composition of Item 64, further comprising at least one additional agent.

66. The pharmaceutical composition of Item 65, wherein the additional agent is selected from the group consisting of a therapeutic agent, an imaging agent, a cytotoxic agent, an angiogenesis inhibitor; a kinase inhibitor; a co-stimulation molecule blocker; an adhesion molecule blocker; an anti-cytokine antibody or functional fragment thereof; methotrexate; cyclosporin; rapamycin; FK506; a detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, $^3$H, $^{14}$C, $^{35}$S, $^{90}$Y, $^{99}$Tc, $^{111}$In, $^{125}$I, $^{131}$I, $^{177}$Lu, $^{166}$Ho, $^{153}$Sm, a fluorescent label, a luminescent label, a bioluminescent label, a magnetic label, biotin, an antidepressant, an antipsychotic, a stimulant, an asthma medication, a beta agonist, an inhaled steroid, an epinephrine or analog, a cytokine, and a cytokine antagonist.

67. A pharmaceutical composition comprising a binding protein conjugate of Item 64, and a pharmaceutically acceptable carrier.

68. A nucleic acid encoding a polypeptide of any of Items 1 to 22, 48-63.

69. An expression construct comprising the nucleic acid of Item 68.

70. A cell comprising the expression construct of Item 69.

71. Use of a binding protein of any of Items 1 to 22, 48-63 for preparation of a medicament for the treatment of a disease or condition selected from the group consisting of arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic diseases, migraine headache, mitochondrial multi. system disorder, mixed connective tissue disease, monoclonal gammopathy, multiple myeloma, multiple systems degenerations (Mencel Dejerine-Thomas Shi-Drager and Machado-Joseph), myasthenia gravis, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/ hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, or xenograft rejection of any organ or tissue.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;
Ausubel et al. (eds.), CURRENT PROTOCOLS IN MOLECULAR BIOLOGY, John Wiley & Sons, NY (1993);
Ausubel, F. M. et al. eds., SHORT PROTOCOLS IN MOLECULAR BIOLOGY (4th Ed. 1999) John Wiley & Sons, NY. (ISBN 0-471-32938-X);
CONTROLLED DRUG BIOAVAILABILITY, DRUG PRODUCT DESIGN AND PERFORMANCE, Smolen and Ball (eds.), Wiley, New York (1984);
Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, N.Y., (1999);
Goodson, in MEDICAL APPLICATIONS OF CONTROLLED RELEASE, vol. 2, pp. 115-138 (1984);
Hammerling, et al., in: MONOCLONAL ANTIBODIES AND T-CELL HYBRIDOMAS 563-681 (Elsevier, N.Y., 1981;
Harlow et al., ANTIBODIES: A LABORATORY MANUAL, (Cold Spring Harbor Laboratory Press, 2nd ed. 1988);
Kabat et al., SEQUENCES OF PROTEINS OF IMMUNOLOGICAL INTEREST (National Institutes of Health, Bethesda, Md. (1987) and (1991);
Kabat, E. A., et al. (1991) SEQUENCES OF PROTEINS OF IMMUNOLOGICAL INTEREST, Fifth Edition, U.S. Department of Health and Human Services, NIH Publication No. 91-3242;
Kontermann and Dubel eds., ANTIBODY ENGINEERING (2001) Springer-Verlag. New York. 790 pp. (ISBN 3-540-41354-5).
Kriegler, Gene Transfer and Expression, A Laboratory Manual, Stockton Press, NY (1990);
Lu and Weiner eds., CLONING AND EXPRESSION VECTORS FOR GENE FUNCTION ANALYSIS (2001) BioTechniques Press. Westborough, Mass. 298 pp. (ISBN 1-881299-21-X).
MEDICAL APPLICATIONS OF CONTROLLED RELEASE, Langer and Wise (eds.), CRC Pres., Boca Raton, Fla. (1974);
Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).
Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).
SUSTAINED AND CONTROLLED RELEASE DRUG DELIVERY SYSTEMS, J. R. Robinson, ed., Marcel Dekker, Inc., New York, 1978
Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

We claim:

1. A monovalent, monospecific binding protein comprising at least two variable heavy domains, at least two variable light domains, and four polypeptide chains, wherein two of said four polypeptide chains comprise VDH-(X1)n-C—(X2)n, wherein VDH is a heavy chain variable domain, X1 is a linker with the proviso that it is not CH1, C is a heavy chain constant domain, X2 is an Fc region, n is 0 or 1;

and wherein two of said four polypeptide chains comprise VDL-(X3)n-C—(X4)n, wherein VDL is a light chain variable domain, X3 is a linker with the proviso that it is not CH1, C is a light chain constant domain, X4 does not comprise an Fc region;

n is 0 or 1;

wherein one of said at least two heavy chain variable domains and/or one of said at least two light chain variable domains comprises a non-naturally occurring mutation, wherein said mutation inhibits targeted binding between a specific antigen and—a mutant binding domain formed by the variable domain comprising the mutation.

2. The binding protein of claim 1, wherein the Fc region of the two polypeptide chains having a formula of VDH-(X1)n-C—(X2)n each comprises a mutation, wherein said mutations on the two Fc regions enhance heterodimerization of the two polypeptide chains.

3. The binding protein of claim 1, wherein one of the four polypeptide chains has a sequence identical to a polypeptide chain selected from the group consisting of SEQ ID Nos. 13-18.

4. The binding protein of claim 1 wherein the mutation combination in antigen binding domain can be acquired by a random-mutagenesis library approach and screened by a functional assay, or can be acquired by a crystallization or molecular modeling-guided approach.

5. A binding protein conjugate comprising a binding protein of claim 1, wherein the binding protein conjugate further comprises an agent selected from the group consisting of an immunoadhesion molecule, an imaging agent, a therapeutic agent, and a cytotoxic agent.

6. A pharmaceutical composition comprising the binding protein of claim 1, and a pharmaceutically acceptable carrier.

7. The pharmaceutical composition of claim 6, further comprising at least one additional agent for treating a disorder, wherein the at least one additional agent is selected from the group consisting of a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof, methotrexate, cyclosporin, rapamycin, FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

* * * * *